(12) United States Patent
Harris et al.

(10) Patent No.: US 7,833,721 B2
(45) Date of Patent: Nov. 16, 2010

(54) BIOMARKERS FOR INFLAMMATORY BOWEL DISEASE AND IRRITABLE BOWEL SYNDROME

(75) Inventors: Cole Harris, Houston, TX (US); John Alsobrook, Corrales, NM (US)

(73) Assignee: Exagen Diagnostics, Inc., Albuquerque, NM (US)

( * ) Notice: Subject to any disclaimer, the term of this patent is extended or adjusted under 35 U.S.C. 154(b) by 0 days.

(21) Appl. No.: 12/403,759

(22) Filed: Mar. 13, 2009

(65) Prior Publication Data

US 2009/0233305 A1 Sep. 17, 2009

Related U.S. Application Data

(60) Provisional application No. 61/036,632, filed on Mar. 14, 2008, provisional application No. 61/097,109, filed on Sep. 15, 2008.

(51) Int. Cl.
*C12Q 1/68* (2006.01)
(52) U.S. Cl. .......................................... 435/6
(58) Field of Classification Search ........................ None
See application file for complete search history.

(56) References Cited

U.S. PATENT DOCUMENTS

| | | | |
|---|---|---|---|
| 6,159,702 A | 12/2000 | Traish | |
| 6,166,190 A | 12/2000 | Fujiwara et al. | |
| 6,562,947 B2 | 5/2003 | Fuliwara et al. | |
| 7,171,311 B2 | 1/2007 | Dai et al. | |
| 2003/0999774 | 5/2003 | Lillie James | |
| 2004/0197777 A1 | 10/2004 | Peltekova | |
| 2007/0010469 A1 | 1/2007 | Chan et al. | |

FOREIGN PATENT DOCUMENTS

| | | |
|---|---|---|
| WO | WO0055173 | 9/2000 |
| WO | WO0129269 | 4/2001 |
| WO | WO0153312 | 7/2001 |
| WO | WO02068579 | 9/2002 |
| WO | WO2004065545 | 8/2004 |
| WO | WO2005016962 | 2/2005 |
| WO | WO2007143752 | 12/2007 |

OTHER PUBLICATIONS

Burczynski et al., Molecular Classification of Crohn's Disease and Ulcerative Colitis Patients Using Transcriptional Profiles in Peripheral Blood Mononuclear Cells, Journal of Molecular Diagnostics 8(1):51-61, Feb. 2006.
GENEBANK Accession No. NM_198976; Jun. 7, 2009.
GENEBANK Accession No. NM_080593; Feb. 11, 2008.
GENEBANK Accession No. NM_003342.4; Oct. 22, 2008.
GENEBANK Accession No. NM_007363; Aug. 2, 2009.
GENEBANK Accession No. NM_001010935.1; Jul. 12, 2009.
GENEBANK Accession No. NM_002884.2; Jul. 12, 2009.
GENEBANK Accession No. NM_006243; Aug. 23, 2009.
GENEBANK Accession No. NM_006698; Feb. 1, 2009.
GENEBANK Accession No. NM_000581.2; Aug. 23, 2009.
GENEBANK Accession No. NM_201397.1; Aug. 23, 2009.
GENEBANK Accession No. NM_005184; May 24, 2009.
Hansen,R.D., et al. Mutat. Res. 664 (1-2), 13-19 (2009).

*Primary Examiner*—Christopher M. Babic
(74) *Attorney, Agent, or Firm*—McDonnell Boehnen Hulbert & Berghoff LLP

(57) ABSTRACT

The present invention provides compositions and their use in diagnosing and/or distinguishing inflammatory bowel disease and irritable bowel syndrome.

8 Claims, 5 Drawing Sheets

BIOMARKERS FOR INFLAMMATORY BOWEL DISEASE AND IRRITABLE BOWEL SYNDROME

CROSS REFERENCE

This application claims priority to U.S. Provisional Patent Application Ser. Nos. 61/036,632 filed Mar. 14, 2008 and 61/097,109 filed Sep. 15, 2008, both references incorporated by reference herein in their entirety.

FIELD OF THE INVENTION

The invention relates generally to the fields of nucleic acids, nucleic acid detection, and intestinal disorders

BACKGROUND

Irritable Bowel Syndrome (IBS) is a chronic condition characterized by abdominal pain, constipation and/or diarrhea. It is fairly common and responsible for 20-50% of visits to gastroenterologists. IBS does not result in damage to the gastrointestinal tract and is not associated with nor develops into more serious gastrointestinal conditions such as colon cancer or colitis, and it can often be controlled with drugs aimed at symptom relief, diet changes, and stress management techniques. However, more serious conditions must be ruled out before making a definitive diagnosis of IBS, and thus setting an appropriate course of treatment.

Inflammatory Bowel Disease (IBD) refers to at least two distinct diseases that cause inflammation of the intestinal tract: Ulcerative Colitis affects the colon, while Crohn's Disease most often affects the last part of the small intestine, but can attack any part of the digestive tract. IBD is rare by comparison to IBS, and IBD patients may experience many of the same symptoms as IBS patients, complicating the diagnosis of IBD. Furthermore, patients with IBD are at greater risk of developing colon cancer. Currently, IBD can only be definitively diagnosed by colonoscopy, a rather invasive procedure; even this invasive procedure is incapable of diagnosing approximately 10% of patients undergoing colonoscopy (Burczynski, J. Mol. Diag. 8(1): 51 (2006)). IBD may be treated with anti-inflammatory drugs, immunosuppressive agents, and/or surgery to remove damaged tissues.

Thus, there is a need in the art for better and more specific diagnostic tests capable of distinguishing between IBD and IBS.

SUMMARY OF THE INVENTION

In a first aspect, the present invention provides biomarkers consisting of between 2 and 35 different nucleic acid probe sets, wherein:

(a) a first probe set that selectively hybridizes under high stringency conditions to a nucleic acid selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3); and (b) a second probe set that selectively hybridizes under high stringency conditions to a nucleic acid selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3), wherein the first probe set and the second probe set do not selectively hybridize to the same nucleic acid.

In a second aspect, the present invention provides biomarker, comprising:

(a) a first primer pair capable of selectively amplifying a detectable portion of a nucleic acid selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3); and (b) a second primer pair capable of selectively amplifying a detectable portion of a nucleic acid selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3), wherein the first primer pair and the second primer pair do not selectively amplify the same nucleic acid.

In a third aspect, the present invention provides methods for diagnosing IBD and/or IBS comprising:

(a) contacting a mRNA-derived nucleic acid sample obtained from a subject suspected of having IBD or IBS under hybridizing conditions with 2 or more probes sets, wherein at least a first probe set and a second probe set selectively hybridize under high stringency conditions to a nucleic acid target selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3); wherein the first probe set and the second probe set do not selectively hybridize to the same nucleic acid;

(b) detecting formation of hybridization complexes between the 2 or more probe sets and nucleic acid targets in the nucleic acid sample, wherein a number of such hybridization complexes provides a measure of gene expression of the nucleic acid targets; and (c) diagnosing whether the subject is likely to have IBD, IBS, or neither based on the gene expression of the nucleic acid targets.

In one embodiment of the third aspect of the invention, diagnosing whether the subject is likely to have IBD, IBS, or neither comprises analyzing gene expression of the nucleic acid targets by applying a weight to the number of hybridization complexes formed for each nucleic acid target.

In a fourth aspect, the present invention provides methods for diagnosing IBD and/or IBS comprising:

(a) contacting a mRNA-derived nucleic acid sample obtained from a subject suspected of having IBD or IBS under amplifying conditions with 2 or more primer pairs, wherein at least a first primer pair and a second primer pair are capable of selectively amplifying a detectable portion of a nucleic acid target selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3); wherein the first primer pair and the second primer pair do not selectively amplify the same nucleic acid;

(b) detecting amplification products generated by amplification of nucleic acid targets in the nucleic acid sample by the two or more primer pairs, wherein the amplification products provide a measure of gene expression of the nucleic acid targets; and (c) diagnosing whether the subject is likely to have IBD, IBS, or neither based on the amplification of the nucleic acid targets.

In one embodiment of the fourth aspect of the invention, diagnosing whether the subject is likely to have IBD, IBS, or neither based on the amplification of the nucleic acid targets comprises analyzing the amplification products by applying a weight to the number of amplification products formed for each nucleic acid target.

DETAILED DESCRIPTION OF THE INVENTION

Figure 1:
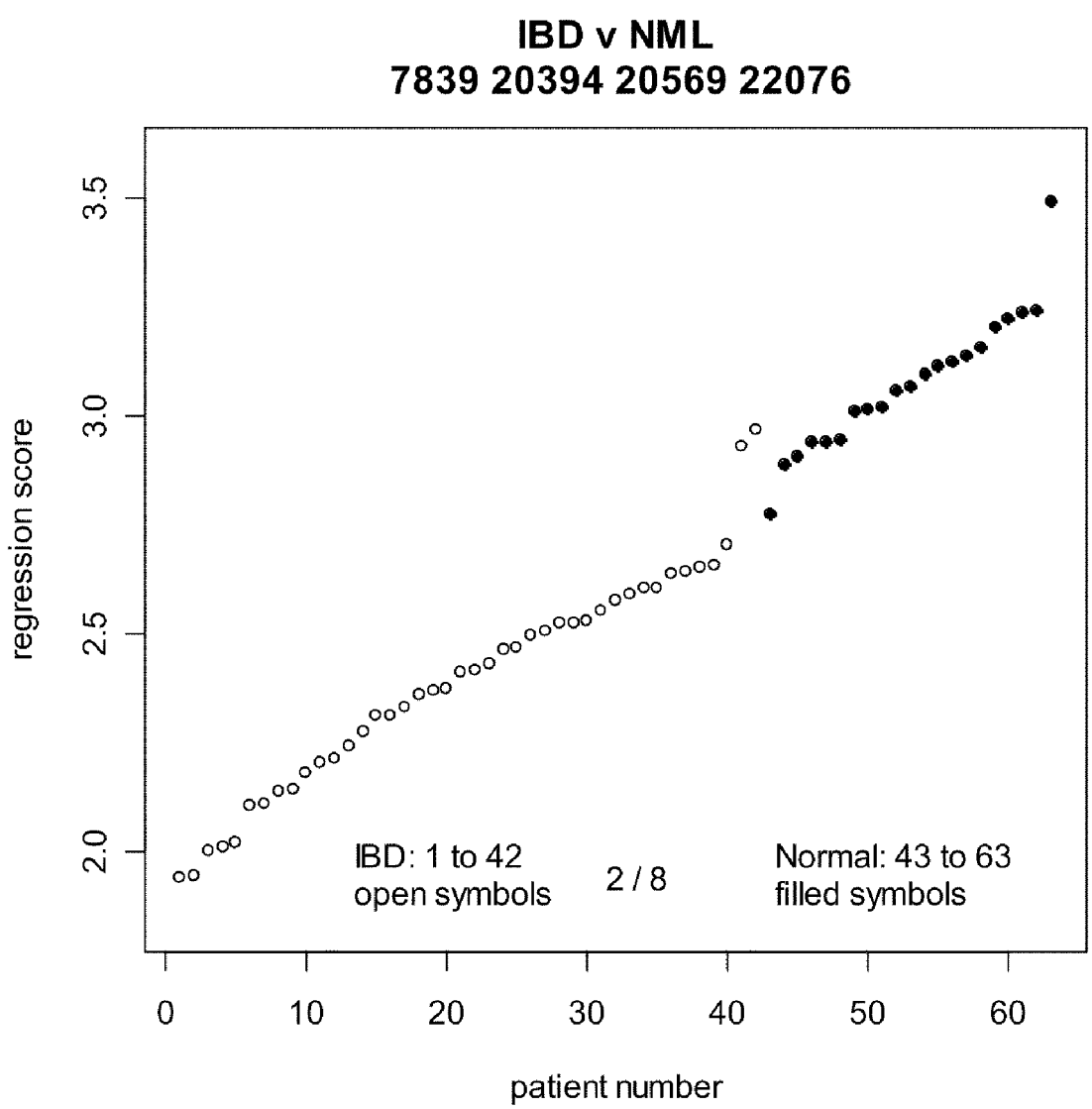
FIG. 1 is a graph of the weighted-sum regression score for each training set patient in an IBD vs. Normal analysis.

All references cited are herein incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

In a first aspect, the invention provides biomarkers consisting of between 2 and 35 different nucleic acid probe sets, wherein:

(a) a first probe set that selectively hybridizes under high stringency conditions to a nucleic acid selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3); and (b) a second probe set that selectively hybridizes under high stringency conditions to a nucleic acid selected from the group consisting of SEQ ID NO:4 (TH1L), SEQ ID NO:11 (HIST1H2AC), SEQ ID NO:12 (TFE3), SEQ ID NO:9 (HIST1H2BK), SEQ ID NO:5 (UBE2G1), SEQ ID NO:13 (NONO), SEQ ID NO:14 (PCBP1), SEQ ID NO:1 and/or 2 (RAP1A), SEQ ID NO:10 (PPP2R5A), SEQ ID NO:15 (PGRMC1), SEQ ID NO:3 (BLCAP), SEQ ID NO:7 and/or 8 (GPX1), SEQ ID NO:16 (HMGB1), and SEQ ID NO:6 (CALM3), wherein the first probe set and the second probe set do not selectively hybridize to the same nucleic acid.

The recited nucleic acids are human nucleic acids recited by SEQ ID NO and gene name; as will be understood by those of skill in the art, such human nucleic acid sequences also include the mRNA counterpart to the sequences disclosed herein. For ease of reference, the nucleic acids will be referred to by gene name throughout the rest of the specification; it will be understood that as used herein the gene name means the recited SEQ. ID. NO(S). for each gene listed in Table 1, complements thereof, and RNA counterparts thereof.

In one non-limiting example, the first probe set selectively hybridizes under high stringency conditions to TH1L, and thus selectively hybridizes under high stringency conditions to the nucleic acid of SEQ ID NO:4 (NM_198978) a mRNA version thereof, or complements thereof, and the second probe set selectively hybridizes under high stringency conditions to RAP1A, thus selectively hybridizing under high stringency conditions to one or both of the nucleic acid of SEQ ID NOS: 1-2, a mRNA version thereof, or complements thereof. Further embodiments will be readily apparent to those of skill in the art based on the teachings herein and Table 1 below.

TABLE 1

| Nucleic acid sequences | | | | |
|---|---|---|---|---|
| Gene name | NCBI accession # | SEQ ID # | Hs.ID | gene description |
| TH1L | NM_198976 | 4 | Hs.517148 | TH1-like (*Drosophila*) |
| HIST1H2AC | NM_003512 | 11 | Hs.484950 | histone 1, H2ac |

TABLE 1-continued

Nucleic acid sequences

| Gene name | NCBI accession # | SEQ ID # | Hs.ID | gene description |
|---|---|---|---|---|
| TFE3 | NM_006521 | 12 | Hs.274184 | Transcription factor binding to IGHM enhancer 3 |
| HIST1H2BK | NM_080593 | 9 | Hs.437275 | Histone 1, H2bk |
| UBE2G1 | NM_003342.4 | 5 | Hs.462035 | Ubiquitin-conjugating enzyme E2G 1 (UBC7 homolog, C. elegans) |
| NONO | NM_007363 | 13 | Hs.533282 | Non-POU domain containing, octamer-binding |
| PCBP1 | NM_006196 | 14 | Hs.2853 | Poly(rC) binding protein 1 |
| RAP1A (1) | NM_001010935.1 | 1 | Hs.190334 | RAP1A, member of RAS oncogene family |
| RAP1A (2) | NM_002884.2 | 2 | | |
| PPP2R5A | NM_006243 | 10 | Hs.497684 | Protein phosphatase 2, regulatory subunit B (B56), alpha isoform |
| PGRMC1 | NM_006667 | 15 | Hs.90061 | Progesterone receptor membrane component 1 |
| BLCAP | NM_006698 | 3 | Hs.472651 | Bladder cancer associated protein |
| GPX1 (1) | NM_000581.2 | 7 | Hs.76686 | Glutathione peroxidase 1 |
| GPX1 (2) | NM_201397.1 | 8 | | |
| HMGB1 | NM_002128 | 16 | Hs.434102 | High-mobility group box 1 |
| CALM3 | NM_005184 | 6 | Hs.515487 | Calmodulin 3 (phosphorylase kinase, delta) |

As is described in more detail below, the inventors have discovered that the biomarkers of the invention can be used, for example, as probes for diagnosing IBD and IBS. The biomarkers can be used, for example, to determine the expression levels in tissue mRNA for the recited genes. The biomarkers of this first aspect of the invention are especially preferred for use in RNA expression analysis from the genes in a tissue of interest, such as blood samples (for example, peripheral blood mononuclear cells (PBMCs) or RBC-depleted whole blood).

As used herein with respect to all aspects and embodiments of the invention, a "probe set" is one or more isolated polynucleotides that each selectively hybridize under high stringency conditions to the same target nucleic acid (for example, a single specific mRNA). Thus, a single "probe set" may comprise any number of different isolated polynucleotides that selectively hybridize under high stringency conditions to the same target nucleic acid, such as a mRNA expression product. For example, a probe set that selectively hybridizes to a BLCAP mRNA may consist of a single polynucleotide of 100 nucleotides that selectively hybridizes under high stringency conditions to BLCAP mRNA, may consist of two separate polynucleotides 100 nucleotides in length that each selectively hybridize under high stringency conditions to BLCAP mRNA, or may consist of twenty separate polynucleotides 25 nucleotides in length that each selectively hybridize under high stringency conditions to BLCAP mRNA (such as, for example, fragmenting a larger probe into many individual shorter polynucleotides). Those of skill in the art will understand that many such permutations are possible.

The biomarkers of the invention consist of between 2 and 35 probe sets. In various embodiments, the biomarker can include 3, 4, 5, 6, 7, 8, 9, 10, 11, 12, 13, or 14 probe sets that selectively hybridize under high stringency conditions to a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3, wherein each of the 3-14 different probe sets selectively hybridize under high stringency conditions to a different nucleic acid target. Thus, as will be clear to those of skill in the art, the biomarkers may include further probe sets that, for example, (a) are additional probe sets that also selectively hybridize under high stringency conditions to the recited human nucleic acid (e.g. RAP1A expresses alternative products that share much overlap; thus, one probe set could selectively hybridize to one transcript (or a cDNA derived therefrom) and another probe set could selectively hybridize to the other alternative transcript (or a cDNA derived therefrom; GPX is a similar example with alternative transcripts); or (b) do not selectively hybridize under high stringency conditions to any of the recited human nucleic acids. Such further probe sets of type (b) may include those consisting of polynucleotides that selectively hybridize to other nucleic acids of interest, and may further include, for example, probe sets consisting of control sequences, such as competitor nucleic acids, sequences to provide a standard of hybridization for comparison, etc.

In various embodiments of this first aspect, the biomarker consists of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 probe sets. In various further embodiments, at least 10%, 15%, 20%, 25%, 30%, 35%, 40%, 45%, 50%, 55%, 60%, 65%, 70%, 75%, 80%, 85%, 90%, 95%, or more of the different probe sets selectively hybridize under high stringency conditions to a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3. As will be apparent to those of skill in the art, as the percentage of probe sets that selectively hybridize under high stringency conditions to a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB 1, and CALM3 increases, the maximum number of probe sets in the biomarker will decrease accordingly. Thus, for example, where at least 50% of the probe sets selectively hybridize under high stringency conditions to a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3, or their complements, the biomarker will consist of between 2 and 28 probe sets. Those of skill in the art will recognize the various other permutations encompassed by the compositions according to the various embodiments of this aspect of the invention.

As used herein with respect to each aspect and embodiment of the invention, the term "selectively hybridizes" means that the isolated polynucleotides are fully complementary to at least a portion of their nucleic acid target so as to form a detectable hybridization complex under the recited hybridization conditions, where the resulting hybridization complex is distinguishable from any hybridization that might occur with other nucleic acids. The specific hybridization conditions used will depend on the length of the polynucleotide probes employed, their GC content, as well as various other factors as is well known to those of skill in the art. (See, for example, Tijssen (1993) Laboratory Techniques in Biochemistry and Molecular Biology—Hybridization with Nucleic Acid Probes part I, chapter 2, "Overview of principles of hybridization and the strategy of nucleic acid probe assays," Elsevier, N.Y. ("Tijssen")). As used herein, "stringent hybridization conditions" are selected to be nor more than 5° C. lower than the thermal melting point (Tm) for the specific polynucleotide at a defined ionic strength and pH. The Tm is the temperature (under defined ionic strength and pH) at which 50% of the target sequence hybridizes to a perfectly matched probe. High stringency conditions are selected to be equal to the Tm for a particular polynucleotide probe. An example of stringent conditions are those that permit selective hybridization of the isolated polynucleotides to the genomic or other target nucleic acid to form hybridization complexes in 0.2×SSC at 65° C. for a desired period of time, and wash conditions of 0.2×SSC at 65° C. for 15 minutes. It is understood that these conditions may be duplicated using a variety of buffers and temperatures. SSC (see, e.g., Sambrook, Fritsch, and Maniatis, in: Molecular Cloning, A Laboratory Manual, Cold Spring Harbor Laboratory Press, 1989) is well known to those of skill in the art, as are other suitable hybridization buffers.

The polynucleotides in the probe sets can be of any length that permits selective hybridization under high stringency conditions to the nucleic acid of interest. In various preferred embodiments of this aspect of the invention and related aspects and embodiments disclosed below, the isolated polynucleotides are at least 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or more contiguous nucleotides in length of one of the recited SEQ ID NOS., full complements thereof, or corresponding RNA sequences.

The term "polynucleotide" as used herein refers to DNA or RNA, preferably DNA, in either single- or double-stranded form. In a preferred embodiment, the polynucleotides are single stranded nucleic acids that are "anti-sense" to the recited nucleic acid (or its corresponding RNA sequence). The term "polynucleotide" encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press).

An "isolated" polynucleotide as used herein for all of the aspects and embodiments of the invention is one which is free of sequences which naturally flank the polynucleotide in the genomic DNA of the organism from which the nucleic acid is derived, and preferably free from linker sequences found in nucleic acid libraries, such as cDNA libraries. Moreover, an "isolated" polynucleotide is substantially free of other cellular material, gel materials, and culture medium when produced by recombinant techniques, or substantially free of chemical precursors or other chemicals when chemically synthesized. The polynucleotides of the invention may be isolated from a variety of sources, such as by PCR amplification from genomic DNA, mRNA, or cDNA libraries derived from mRNA, using standard techniques; or they may be synthesized in vitro, by methods well known to those of skill in the art, as discussed in U.S. Pat. No. 6,664,057 and references disclosed therein. Synthetic polynucleotides can be prepared by a variety of solution or solid phase methods. Detailed descriptions of the procedures for solid phase synthesis of polynucleotide by phosphite-triester, phosphotriester, and H-phosphonate chemistries are widely available. (See, for example, U.S. Pat. No. 6,664,057 and references disclosed therein). Methods to purify polynucleotides include native acrylamide gel electrophoresis, and anion-exchange HPLC, as described in Pearson (1983) J. Chrom. 255:137-149. The sequence of the synthetic polynucleotides can be verified using standard methods.

In one embodiment, the polynucleotides are double or single stranded nucleic acids that include a strand that is "anti-sense" to all or a portion of the SEQ ID NOS shown above for each gene of interest or its corresponding RNA sequence (ie: it is fully complementary to the recited SEQ ID NOs). In one non-limiting example, the first probe set selectively hybridizes under high stringency conditions to TH1L, and is fully complementary to all or a portion of the nucleic acid of SEQ ID NO:4 (NM_198978) or a mRNA version thereof, and the second probe set selectively hybridizes under high stringency conditions to RAP1A and is fully complementary to one or both of the nucleic acid of SEQ ID NOS: 1-2 or a mRNA version thereof.

In one preferred embodiment of the first aspect of the invention, the biomarker comprises or consists of at least 3, 4, or 5 probe sets that selectively hybridize under high stringency conditions to a nucleic acid selected from the group consisting of TH1L, HIST1H2BK, UBE2G1, BLCAP, and CALM3. As disclosed in more detail below, such probe sets can be used in preferred embodiments of the methods of the invention for distinguishing normal subjects from those subjects suffering from IBS. Examples of such preferred probe sets are provided in Table 17. Thus, in a preferred embodiment, the invention provides a biomarker consisting of between 3 and 35 different nucleic acid probe sets, wherein:

(a) a first probe set consisting of one or more nucleotide probes consisting of 15 or more contiguous nucleotides of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), or a full complement thereof;

(b) a second probe set consisting of one or more nucleotide probes consisting of 15 or more contiguous nucleotides of a nucleic acid selected from the group consisting of SEQ ID NO:4 (TH1L), SEQ ID NO:9 (HIST1H2BK), SEQ ID NO:5

(UBE2G1), SEQ ID NO:3 (BLCAP), and SEQ ID NO:6 (CALM3), or a full complement thereof; and (c) a third probe set consisting of one or more nucleotide probes consisting of 15 or more contiguous nucleotides of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), or a full complement thereof;

wherein each of the between 3 and 35 different probe sets consists of one or more probes of 15 or more contiguous nucleotides, or full complements thereof, of a single mRNA different from that of the other probe sets, and wherein each of the different probe sets is optionally detectably labeled. In a further preferred version of this embodiment, the first probe set consists of one or more nucleotide probes of 15 or more contiguous nucleotides of BLCAP, or a full complement thereof; the second probe set consists of one or more nucleotide probes of 15 or more contiguous nucleotides of TH1L, or a full complement thereof; the third probe set consists of one or more nucleotide probes of 15 or more contiguous nucleotides of UBE2G 1, or a full complement thereof; and a fourth probe set consists of one or more nucleotide probes of 15 or more contiguous nucleotides of HIST1H2BK, or a full complement thereof.

In another preferred embodiment of the first aspect of the invention, the biomarker comprises or consists of at least 5 or 6 probe sets that probe sets selectively hybridize under high stringency conditions to a nucleic acid selected from the group consisting of RAP1A, BLCAP, UBE2G1, GPX1, CALM3, and NONO. As disclosed in more detail below, such probe sets can be used in preferred embodiments of the methods of the invention for distinguishing normal subjects from those subjects suffering from IBD. Examples of such preferred probe sets are provided in Table 18. In one preferred version of this embodiment, the biomarker consists of between 5 and 35 different nucleic acid probe sets, wherein:

(a) a first probe set consisting of one or more nucleotide probes consisting of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

(b) a second probe set consisting of one or more nucleotide probes consisting of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

(c) a third probe set consisting of one or more nucleotide probes consisting of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

(d) a fourth probe set consisting of one or more nucleotide probes consisting of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof; and (e) a fifth probe set consisting of one or more nucleotide probes consisting of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

wherein each of the between 5 and 35 different probe sets consists of one or more probes of 15 or more contiguous nucleotides, or full complements thereof, of a single mRNA different from that of the other probe sets, and wherein each of the different probe sets is optionally detectably labeled. In another version, the first probe set consists of one or more nucleotide probes of 15 or more contiguous nucleotides of RAP1A, or a full complement thereof; the second probe set consists of one or more nucleotide probes of 15 or more contiguous nucleotides of BLCAP, or a full complement thereof; the third probe set consists of one or more nucleotide probes of 15 or more contiguous nucleotides of UBE2G 1, or a full complement thereof; the fourth probe set consists of one or more nucleotide probes of 15 or more contiguous nucleotides of CALM3, or a full complement thereof; the fifth probe set consists of one or more nucleotide probes of 15 or more contiguous nucleotides of GPX1, or a full complement thereof; and a sixth probe set consists of one or more nucleotide probes of 15 or more contiguous nucleotides of NONO or a full complement thereof.

In a further preferred embodiment of the first aspect of the invention, the biomarker comprises or consists of at least 6 or 7 probe sets that selectively hybridize under high stringency conditions to a nucleic acid selected from the group consisting of RAP1A, BLCAP, UBE2G1, CALM3, GPX1, HIST1H2BK, and PPP2R5A. As disclosed in more detail below, such probe sets can be used in preferred embodiments of the methods of the invention for distinguishing those subjects suffering from IBS from those subjects suffering from IBD. Examples of such preferred probe sets are provided in Table 19. In one preferred embodiment, the biomarker consists of (a) a first probe set consisting of one or more nucleotide probes consisting of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(b) a second probe set consisting of one or more nucleotide probes consisting of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(c) a third probe set consisting of one or more nucleotide probes consisting of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(d) a fourth probe set consisting of one or more nucleotide probes consisting of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(e) a fifth probe set consisting of one or more nucleotide probes consisting of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof; and (f) a sixth probe set consisting of one or more nucleotide probes consisting of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

wherein each of the between 6 and 35 different probe sets consists of one or more probes of 15 or more contiguous nucleotides, or full complements thereof, of a single mRNA different from that of the other probe sets, and wherein each of the different probe sets is optionally detectably labeled. In a further preferred embodiment, the first probe set consists of one or more nucleotide probes of 15 or more contiguous nucleotides of RAP1A, or a full complement thereof; the second probe set consists of one or more nucleotide probes of 15 or more contiguous nucleotides of UBE2G1, or a full complement thereof; the third probe set consists of one or more nucleotide probes of 15 or more contiguous nucleotides of CALM3, or a full complement thereof; the fourth probe set consists of one or more nucleotide probes of 15 or more contiguous nucleotides of GPX1, or a full complement thereof; the fifth probe set consists of one or more nucleotide probes of 15 or more contiguous nucleotides of HIST1H2BK, or a full complement thereof; the sixth probe set consists of one or more nucleotide probes of 15 or more contiguous nucleotides of PPP2R5A, or a full complement thereof; and a seventh probe set consists of one or more nucleotide probes of 15 or more contiguous nucleotides of BLCAP, or a full complement thereof.

In one specific embodiment of this first aspect of the invention, the biomarker includes a first probe set that selectively hybridizes under high stringency conditions to BLCAP, a second probe set that selectively hybridizes under high stringency conditions to TH1L, a third probe set that selectively hybridizes under high stringency conditions to CALM3, and a fourth probe set that selectively hybridizes under high stringency conditions to HIST1H2BK. As disclosed in more detail below, the inventors have discovered that such biomarkers can be used as probes to distinguish between normal and IBS patients.

In a second specific embodiment of this first aspect of the invention, the biomarker includes a first probe set that selectively hybridizes under high stringency conditions to BLCAP, a second probe set that selectively hybridizes under high stringency conditions to TH1L, a third probe set that selectively hybridizes under high stringency conditions to UBE2G1, and a fourth probe set that selectively hybridizes under high stringency conditions to HIST1H2BK. As disclosed in more detail below, the inventors have discovered that such biomarkers can be used as probes to distinguish between normal and IBS patients.

In a third specific embodiment of this first aspect of the invention, the biomarker includes a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to GPX1. As disclosed in more detail below, the inventors have discovered that such biomarkers can be used as probes to distinguish between normal and IBD patients.

In a fourth specific embodiment of this first aspect of the invention, the biomarker includes a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to CALM3, and a fifth probe set that selectively hybridizes under high stringency conditions to GPX1. As disclosed in more detail below, the inventors have discovered that such biomarkers can be used as probes to distinguish between normal and IBD patients.

In a fifth specific embodiment of this first aspect of the invention, the biomarker includes a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to CALM3, a fifth probe set that selectively hybridizes under high stringency conditions to GPX1, and a sixth probe set that selectively hybridizes under high stringency conditions to NONO. As disclosed in more detail below, the inventors have discovered that such biomarkers can be used as probes to distinguish between normal and IBD patients.

In a sixth specific embodiment of this first aspect of the invention, the biomarker includes a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to CALM3, a fifth probe set that selectively hybridizes under high stringency conditions to GPX1, a sixth probe set that selectively hybridizes under high stringency conditions to HIST1H2BK, and a seventh probe set that selectively hybridizes under high stringency conditions to PPP2RR5A. As disclosed in more detail below, the inventors have discovered that such biomarkers can be used as probes to distinguish normal and IBS patients from IBD patients.

In a seventh specific embodiment of this first aspect of the invention, the biomarker includes a first probe set that selectively hybridizes under high stringency conditions to RAP1A, a second probe set that selectively hybridizes under high stringency conditions to UBE2G1, a third probe set that selectively hybridizes under high stringency conditions to CALM3, a fourth probe set that selectively hybridizes under high stringency conditions to GPX1, a fifth probe set that selectively hybridizes under high stringency conditions to HIST1H2BK1, and a sixth probe set that selectively hybridizes under high stringency conditions to PPP2R5A. As disclosed in more detail below, the inventors have discovered that such biomarkers can be used as probes to distinguish IBS patients from IBD patients.

In an eighth specific embodiment of this first aspect of the invention, the biomarker includes a first probe set that selectively hybridizes under high stringency conditions to RAP1A, a second probe set that selectively hybridizes under high stringency conditions to UBE2G1, a third probe set that selectively hybridizes under high stringency conditions to CALM3, a fourth probe set that selectively hybridizes under high stringency conditions to GPX1, a fifth probe set that selectively hybridizes under high stringency conditions to HIST1H2BK, a sixth probe set that selectively hybridizes under high stringency conditions to PPP2R5A, and a seventh probe set that selectively hybridizes under high stringency conditions to BLCAP. As disclosed in more detail below, the inventors have discovered that such biomarkers can be used as probes to distinguish IBS patients from IBD patients.

In a ninth specific embodiment of this first aspect of the invention, the biomarker includes a first probe set that selectively hybridizes under high stringency conditions to BLCAP, a second probe set that selectively hybridizes under high stringency conditions to CALM3, a third probe set that selectively hybridizes under high stringency conditions to GPX1, a fourth probe set that selectively hybridizes under high stringency conditions to TH1L, a fifth probe set that selectively hybridizes under high stringency conditions to RAP1A, and a sixth probe set that selectively hybridizes under high stringency conditions to NONO. As disclosed in more detail below, the inventors have discovered that such biomarkers can be used as probes to distinguish IBS and IBD patients from normal patients.

Thus, in various other embodiments of this first aspect of the invention, the biomarker comprises or consists of one or more of:

(a) a first probe set that selectively hybridizes under high stringency conditions to RAP1A and a second probe set that selectively hybridizes under high stringency conditions to GPX1 (used as a probe set pair common to biomarkers for diagnosing IBD from normal patients; IBD from normal and IBS patients; IBD from IBS patients; and IBD and IBS patients from normal patients);

(b) a first probe set that selectively hybridizes under high stringency conditions to UBE2G1 and a second probe set that selectively hybridizes under high stringency conditions to BLCAP (used as a probe set pair that can be added to probe set pair (a) to generate a 4-gene biomarker specific for diagnosing IBD from normal);

(c) a first probe set that selectively hybridizes under high stringency conditions to UBE2G1, a second probe set that selectively hybridizes under high stringency conditions to BLCAP and a third probe set that selectively hybridizes under high stringency conditions to CALM3 (used as a probe trio that can be added to probe set pair (a) to generate a 5-gene biomarker for diagnosing IBD from normal);

(d) a first probe set that selectively hybridizes under high stringency conditions to NONO and a second probe set that selectively hybridizes under high stringency conditions to CALM3 (used as a probe set pair that, can be added to probe sets (a) and (b) to generate a 6-gene biomarker for diagnosing IBD from normal);

(e) a first probe set that selectively hybridizes under high stringency conditions to PPP2R5A and a second probe set that selectively hybridizes under high stringency conditions to HIST1H2BK (used as a probe set pair common to biomarkers for diagnosing IBD from IBS patients). The probe set (e), when combined with probe sets (a), and (c) disclosed above for distinguishing IBD from normal, generates a biomarker for diagnosing normal and IBS patients from IBD patients). The probe set combination of (e), (a), and (c) can also be used as a biomarker to distinguish between IBS and IBD patients when the expression values of the individual genes are given different weights as discussed herein;

(f) a first probe set that selectively hybridizes under high stringency conditions to UBE2G1 and a second probe set that selectively hybridizes under high stringency conditions to CALM3 (used as a probe set pair that can be added to probe sets (a), and (e) described above, to generate a 6-gene biomarker that can be used to distinguish IBD from IBS patients);

(g) a first probe set that selectively hybridizes under high stringency conditions to BLCAP and a second probe set that selectively hybridizes under high stringency conditions to TH1L (used as probe set pair that when added to (a) and (d) above can be used to generate a 6-gene biomarker that can distinguish patients with IBS or IBD from normal patients);

h) a first probe set that selectively hybridizes under high stringency conditions to HIST1H2KB and a second probe set that selectively hybridizes under high stringency conditions to CALM3; (used as probe set pair that when added to (g) above can be used to generate a 4-gene biomarker that can distinguish patients with IBS from normal patients); and i) a first probe set that selectively hybridizes under high stringency conditions to HIST1H2KB and a second probe set that selectively hybridizes under high stringency conditions to UBE2G1 (used as probe set pair that when added to (g) above can be used to generate a different 4-gene biomarker that can distinguish patients with IBS from normal patients).

In a second aspect, the present invention provides biomarkers, comprising or consisting of (a) a first primer pair capable of selectively amplifying a detectable portion of a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3; and (b) a second primer pair capable of selectively amplifying a detectable portion of a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3;

wherein the first primer pair and the second primer pair do not selectively amplify the same nucleic acid.

As is described in more detail below, the inventors have discovered that the biomarkers of the invention can be used, for example, as primers for amplification assays for diagnosing IBD and IBS. The biomarkers can be used, for example, to determine the expression levels in tissue mRNA for the recited genes. The biomarkers of this second aspect of the invention are especially preferred for use in RNA expression analysis from the genes in a tissue of interest, such as blood samples (PBMCs or RBC-depleted whole blood).

The nucleic acid targets have been described in detail above, as have polynucleotides in general. As used herein, "selectively amplifying" means that the primer pairs are complementary to their targets and can be used to amplify a detectable portion of the nucleic acid target that is distinguishable from amplification products due to non-specific amplification. In a preferred embodiment, the primers are fully complementary to their target.

As is well known in the art, polynucleotide primers can be used in various assays (PCR, RT-PCR, RTQ-PCR, spPCR, qPCR, and allele-specific PCR, etc.) to amplify portions of a target to which the primers are complementary. Thus, a primer pair would include both a "forward" and a "reverse" primer, one complementary to the sense strand (ie: the strand shown in the sequences provided herein) and one complementary to an "antisense" strand (ie: a strand complementary to the strand shown in the sequences provided herein), and designed to hybridize to the target so as to be capable of generating a detectable amplification product from the target of interest when subjected to amplification conditions. The sequences of each of the target nucleic acids are provided herein, and thus, based on the teachings of the present specification, those of skill in the art can design appropriate primer pairs complementary to the target of interest (or complements thereof). In various embodiments, each member of the primer pair is a single stranded DNA polynucleotide at least 15, 16, 17, 18, 19, 20, 21, 22, 23, 24, 25, 26, 27, 28, 29, 30, or more nucleotides in length that are fully complementary to the nucleic acid target. In various further embodiments, the detectable portion of the target nucleic acid that is amplified is at least 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or more nucleotides in length.

In various embodiments, the biomarker can comprise or consist of 3, 4, 5, 6, 7, 8, 9, 10, 11, 12, 13, or 14 primer pairs that selectively hybridizes under high stringency conditions to a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3, wherein none of the 3-14 primer pairs selectively amplify the same nucleic acid. In a preferred embodiment, the primers are fully complementary to their target. Thus, as will be clear to those of skill in the art, the biomarkers may include further primer pairs that do not selectively amplify any of the recited human nucleic acids. Such further primer pairs may include those consisting of polynucleotides that selectively amplify other nucleic acids of interest, and may further include, for example, primer pairs to provide a standard of amplification for comparison, etc.

In various embodiments of this second aspect, the biomarker consists of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 primer pairs. In various further embodiments, at least 10%, 15%, 20%, 25%, 30%, 35%, 40%, 45%, 50%, 55%, 60%, 65%, 70%, 75%, 80%, 85%, 90%, 95%, or more of the different primer pairs selectively amplify a detectable portion of a nucleic acid selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3.

In one preferred embodiment of the second aspect of the invention, the biomarker comprises or consists of at least 3, 4, or 5 primer pairs that selectively amplify a detectable portion of a nucleic acid selected from the group consisting of TH1L, HIST1H2BK, UBE2G1, BLCAP, and CALM3. As disclosed in more detail below, such primer pairs can be used in preferred embodiments of the methods of the invention for distinguishing normal subjects from those subjects suffering from IBS. Examples of such preferred primer pairs are those that amplify a detectable portion of the nucleic acids provided in Table 17. Thus, in one preferred version of this embodiment, the biomarker consists of between 3 and 35 different nucleic acid primer pairs, wherein:

(a) a first primer pair capable of selectively amplifying a detectable portion of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), wherein each primer in the first primer pair consists of 15 or more contiguous nucleotides of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), or a full complement thereof;

(b) a second primer pair capable of selectively amplifying a detectable portion of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), wherein each primer in the second primer pair consists of 15 or more contiguous nucleotides of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), or a full complement thereof; and (c) a third primer pair capable of selectively amplifying a detectable portion of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), wherein each primer in the third primer pair consists of 15 or more contiguous nucleotides of a nucleic acid selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), or a full complement thereof;

wherein each of the between 3 and 35 different primer pairs consists of one or more primer pairs of 15 or more contiguous nucleotides, or full complements thereof, for a single mRNA different from that of the other primer pairs, and wherein each of the different primer pairs is optionally detectably labeled. In a further preferred version of this embodiment, each primer in the first primer pair consists of 15 or more contiguous nucleotides of BLCAP, or a full complement thereof; each primer in the second primer pair consists of 15 or more contiguous nucleotides of TH1L, or a full complement thereof; each primer in the third primer pair consists of 15 or more contiguous nucleotides of UBE2G1, or a full complement thereof; and each primer in a fourth primer pair consists of 15 or more contiguous nucleotides of HIST1H2BK, or a full complement thereof.

In another preferred embodiment of the second aspect of the invention, the biomarker comprises or consists of at least 5 or 6 primer pairs that selectively amplify a detectable portion of a nucleic acid selected from the group consisting of RAP1A, BLCAP, UBE2G1, GPX1, CALM3, and NONO. As disclosed in more detail below, such primer pairs can be used in preferred embodiments of the methods of the invention for distinguishing normal subjects from those subjects suffering from IBD. Examples of such preferred primer pairs are those that amplify a detectable portion of the nucleic acids provided in Table 18. In one preferred version of this embodiment, the biomarker consists of between 5 and 35 different nucleic acid primer pairs, wherein:

(a) a first primer pair capable of selectively amplifying a detectable portion of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), wherein each primer in the first primer pair consists of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

(b) a second primer pair capable of selectively amplifying a detectable portion of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO)), wherein each primer in the second primer pair consists of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

(c) a third primer pair capable of selectively amplifying a detectable portion of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), wherein each primer in the third primer pair consists of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

(d) a fourth primer pair capable of selectively amplifying a detectable portion of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), wherein each primer in the fourth primer pair consists of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof; and (e) a fifth primer pair capable of selectively amplifying a detectable portion of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), wherein each primer in the fifth primer pair consists of 15 or more contiguous nucleotides of a nucleic acid selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof;

wherein each of the between 5 and 35 different primer pairs consists of one or more primer pairs of 15 or more contiguous nucleotides, or full complements thereof, for a single mRNA different from that of the other primer pairs, and wherein each of the different primer pairs is optionally detectably labeled. In a further embodiment, each primer in the first primer pair consists of 15 or more contiguous nucleotides of RAP1A, or a full complement thereof; each primer in the second primer pair consists of 15 or more contiguous nucleotides of BLCAP, or a full complement thereof; each primer in the third primer pair consists of 15 or more contiguous nucleotides of UBE2G1, or a full complement thereof; each primer in the fourth primer pair consists of 15 or more contiguous nucleotides of CALM3, or a full complement thereof; each primer in the fifth primer pair consists of 15 or more contiguous nucleotides of GPX1, or a full complement thereof; and each primer in a sixth primer pair consists of 15 or more contiguous nucleotides of NONO, or a full complement thereof.

In a further preferred embodiment of the second aspect of the invention, the biomarker comprises or consists of at least 6 or 7 primer pairs that selectively amplify a detectable portion of a nucleic acid selected from the group consisting of RAP1A, BLCAP, UBE2G1, CALM3, GPX1, HIST1H2BK, and PPP2R5A. As disclosed in more detail below, such primer pairs can be used in preferred embodiments of the methods of the invention for distinguishing those subjects suffering from IBS from those subjects suffering from IBD. Examples of such preferred primer pairs are those that amplify a detectable portion of the nucleic acids provided in Table 19. In one preferred embodiment, the biomarker consists of between 6 and 35 different nucleic acid primer pairs, wherein:

(a) a first primer pair capable of selectively amplifying a detectable portion of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), wherein each primer in the first primer pair consists of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(b) a second primer pair capable of selectively amplifying a detectable portion of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), wherein each primer in the second primer pair consists of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(c) a third primer pair capable of selectively amplifying a detectable portion of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), wherein each primer in the third primer pair consists of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(d) a fourth primer pair capable of selectively amplifying a detectable portion of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), wherein each primer in the fourth primer pair consists of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

(e) a fifth primer pair capable of selectively amplifying a detectable portion of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), wherein each primer in the fifth primer pair consists of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8

(GPX1), SEQ ID NO:9 (HIST1H2BK), SEQ ID NO:10 (PPP2R5A), and SEQ ID NO:3 (BLCAP), or a full complement thereof; and (f) a sixth primer pair capable of selectively amplifying a detectable portion of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), wherein each primer in the sixth primer pair consists of 15 or more contiguous nucleotides of a nucleic acid selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof;

wherein each of the between 6 and 35 different primer pairs consists of one or more primer pairs of 15 or more contiguous nucleotides, or full complements thereof, for a single mRNA different from that of the other primer pairs, and wherein each of the different primer pairs is optionally detectably labeled. In another preferred embodiment, each primer in the first primer pair consists of 15 or more contiguous nucleotides of RAP1A, or a full complement thereof; each primer in the second primer pair consists of 15 or more contiguous nucleotides of UBE2G1, or a full complement thereof; each primer in the third primer pair consists of 15 or more contiguous nucleotides of CALM3, or a full complement thereof; each primer in the fourth primer pair consists of 15 or more contiguous nucleotides of GPX1, or a full complement thereof; each primer in the fifth primer pair consists of 15 or more contiguous nucleotides of HIST1H2BK, or a full complement thereof; each primer in the sixth primer pair consists of 15 or more contiguous nucleotides of PPP2R5A, or a full complement thereof; and wherein each primer in a seventh primer pair consists of 15 or more contiguous nucleotides of BLCAP, or a full complement thereof.

In one specific embodiment, a biomarker according to this second aspect of the invention comprises or consists of a first primer pair that selectively amplifies a detectable portion of BLCAP a second primer pair that selectively amplifies a detectable portion of TH1L, a third primer pair that selectively amplifies a detectable portion of CALM3, and a fourth primer pair that selectively amplifies a detectable portion of HIST1H2BK. As disclosed in more detail below, the inventors have discovered that such biomarkers can be used as probes to distinguish between normal and IBS patients.

In a second specific embodiment of this second aspect of the invention, a biomarker according to this second aspect of the invention comprises or consists of a first primer pair that selectively amplifies a detectable portion of BLCAP, a second primer pair that selectively amplifies a detectable portion of TH1L, a third primer pair that selectively amplifies a detectable portion of UBE2G1, and a fourth primer pair that selectively amplifies a detectable portion of HIST1H2BK. As disclosed in more detail below, the inventors have discovered that such biomarkers can be used as probes to distinguish between normal and IBS patients.

In a third specific embodiment of this second aspect of the invention, the biomarker includes a first primer pair that selectively amplifies a detectable portion of RAP1A, a second primer pair that selectively amplifies a detectable portion of BLCAP, a third primer pair that selectively amplifies a detectable portion of UBE2G1, and a fourth primer pair that selectively amplifies a detectable portion of GPX1. As disclosed in more detail below, the inventors have discovered that such biomarkers can be used as probes to distinguish between normal and IBD patients.

In a fourth specific embodiment of this second aspect of the invention, the biomarker of this second aspect comprises or consists of a first primer pair that selectively amplifies a detectable portion of RAP1A, a second primer pair that selectively amplifies a detectable portion of BLCAP, a third primer pair that selectively amplifies a detectable portion of UBE2G1, a fourth primer pair that selectively amplifies a detectable portion of CALM3, and a fifth primer pair that selectively amplifies a detectable portion of GPX1. As disclosed in more detail below, the inventors have discovered that such biomarkers can be used as probes to distinguish between normal and IBD patients In a fifth specific embodiment of this second aspect of the invention, the biomarker of this second aspect comprises or consists of a first primer pair that selectively amplifies a detectable portion of RAP1A, a second primer pair that selectively amplifies a detectable portion of BLCAP, a third primer pair that selectively amplifies a detectable portion of UBE2G1, a fourth primer pair that selectively amplifies a detectable portion of CALM3, a fifth primer pair that selectively amplifies a detectable portion of GPX1, and a sixth primer pair that selectively amplifies a detectable portion of NONO. As disclosed in more detail below, the inventors have discovered that such biomarkers can be used as probes to distinguish between normal and IBD patients.

In a sixth specific embodiment of this second aspect of the invention, the biomarker of this second aspect comprises or consists of a primer pair that selectively amplifies a detectable portion of RAP1A, a second primer pair that selectively amplifies a detectable portion of BLCAP, a third primer pair that selectively amplifies a detectable portion of UBE2G1, a fourth primer pair that selectively amplifies a detectable portion of CALM3, a fifth primer pair that selectively amplifies a detectable portion of GPX1, a sixth primer pair that selectively amplifies a detectable portion of HIST1H2BK, and a seventh primer pair that selectively amplifies a detectable portion of PPP2RR5A. As disclosed in more detail below, the inventors have discovered that such biomarkers can be used as probes to distinguish normal and IBS patients from IBD patients.

In a seventh specific embodiment of this second aspect of the invention, the biomarker of this second aspect comprises or consists of a first primer pair that selectively amplifies a detectable portion of RAP1A, a second primer pair that selectively amplifies a detectable portion of UBE2G1, a third primer pair that selectively amplifies a detectable portion of CALM3, a fourth primer pair that selectively amplifies a detectable portion of GPX1, a fifth primer pair that selectively amplifies a detectable portion of HIST1H2BK, and a sixth primer pair that selectively amplifies a detectable portion of PPP2R5A. As disclosed in more detail below, the inventors have discovered that such biomarkers can be used as probes to distinguish between IBS patients and IBD patients.

In an eighth specific embodiment of this second aspect of the invention, the biomarker of this second aspect comprises or consists of a primer pair that selectively amplifies a detectable portion of RAP1A, a second primer pair that selectively amplifies a detectable portion of UBE2G1, a third primer pair that selectively amplifies a detectable portion of CALM3, a fourth primer pair that selectively amplifies a detectable portion of GPX1, a fifth primer pair that selectively amplifies a detectable portion of HIST1H2BK, a sixth primer pair that selectively amplifies a detectable portion of PPP2R5A, and a seventh primer pair that selectively amplifies a detectable portion of BLCAP. As disclosed in more detail below, the inventors have discovered that such biomarkers can be used as probes to distinguish IBS patients from IBD patients.

In a ninth specific embodiment of this second aspect of the invention, the biomarker of this second aspect comprises or consists of a first primer pair that selectively amplifies a detectable portion of BLCAP, a second primer pair that selectively amplifies a detectable portion of CALM3, a third primer pair that selectively amplifies a detectable portion of GPX 1, a fourth primer pair that selectively amplifies a detectable portion of TH1L, a fifth primer pair that selectively amplifies a detectable portion of RAP1A, and a sixth primer pair that selectively amplifies a detectable portion of NONO. As disclosed in more detail below, the inventors have discovered that such biomarkers can be used as probes to distinguish IBS and IBD patients from normal patients.

Thus, in various other embodiments of this second aspect of the invention, the biomarker comprises or consists of:

(a) a first primer pair that selectively amplifies a detectable portion of RAP1A and a second primer pair that selectively amplifies a detectable portion of GPX1 (used as a primer pair set common to biomarkers for diagnosing IBD from normal patients; IBD from normal and IBS; IBD from IBS; and IBD and IBS from normal);

(b) a first primer pair that selectively amplifies a detectable portion of UBE2G1 and a second primer pair that selectively amplifies a detectable portion of BLCAP (used as a primer pair set that can be added to primer pair set (a) to generate a 4-gene biomarker specific for diagnosing IBD from normal);

(c) a first primer pair that selectively amplifies a detectable portion of UBE2G1, a second primer pair that selectively amplifies a detectable portion of BLCAP, and a third primer pair that selectively amplifies a detectable portion of CALM3 (used as a primer pair trio that can be added to primer pair (a) to generate a 5-gene biomarker for diagnosing IBD from normal);

(d) a first primer pair that selectively amplifies a detectable portion of NONO and a second primer pair that selectively amplifies a detectable portion of CALM3 (used as a primer pair set that, can be added to primer pair sets (a) and (b) to generate a 6-gene biomarker for diagnosing IBD from normal);

(e) a first primer pair that selectively amplifies a detectable portion of PPP2R5A and a second primer pair that selectively amplifies a detectable portion of HIST1H2BK (used as a primer pair set pair common to biomarkers for diagnosing IBD from IBS patients). The primer pair set (e), when combined with primer pair sets (a), and (c) disclosed above for distinguishing IBD from normal, generates a biomarker for diagnosing normal and IBS patients from IBD patients). The primer pair set combination of (e), (a), and (c) can also be used as a biomarker to distinguish between IBS and IBD patients when the expression values of the individual genes are given different weights as discussed herein;

(f) a first primer pair that selectively amplifies a detectable portion of UBE2G1 and a second primer pair that selectively amplifies a detectable portion of CALM3 (used as a primer pair that can be added to primer pair sets (a), and (e) described above, to generate a 6-gene biomarker that can be used to distinguish IBD from IBS patients);

(g) a first primer pair that selectively amplifies a detectable portion of BLCAP and a second primer pair that selectively amplifies a detectable portion of TH1L (used as primer pair set that when added to (a) and (d) above can be used to generate a 6-gene biomarker that can distinguish patients with IBS or IBD from normal patients;

(h) a first primer pair that selectively amplifies a detectable portion of HIST1H2KB and a second primer pair that selectively amplifies a detectable portion of CALM3 (used as primer pair set that when added to (g) above can be used to generate a 4-gene biomarker that can distinguish patients with IBS from normal patients; and (i) a first primer pair that selectively amplifies a detectable portion of HIST1H2KB and a second primer pair that selectively amplifies a detectable portion of UBE2G1 (used as primer pair set that when added to (h) above can be used to generate a different 4-gene biomarker that can distinguish patients with IBS from normal patients.

The biomarkers of the first and second aspects of the invention can be stored frozen, in lyophilized form, or as a solution containing the different probe sets or primer pairs. Such a solution can be made as such, or the composition can be prepared at the time of hybridizing the polynucleotides to target, as discussed below. Alternatively, the compositions can be placed on a solid support, such as in a microarray or microplate format.

In all of the above aspects and embodiments, the polynucleotides can be labeled with a detectable label. In a preferred embodiment, the detectable labels for polynucleotides in different probe sets are distinguishable from each other to, for example, facilitate differential determination of their signals when conducting hybridization reactions using multiple probe sets. Methods for detecting the label include, but are not limited to spectroscopic, photochemical, biochemical, immunochemical, physical or chemical techniques. For example, useful detectable labels include but are not limited to radioactive labels such as $^{32}P$, $^{3}H$, and $^{14}C$; fluorescent dyes such as fluorescein isothiocyanate (FITC), rhodamine, lanthanide phosphors, and Texas red, ALEXIS™ (Abbott Labs), CY™ dyes (Amersham); electron-dense reagents such as gold; enzymes such as horseradish peroxidase, beta-galactosidase, luciferase, and alkaline phosphatase; calorimetric labels such as colloidal gold; magnetic labels such as those sold under the mark DYNABEADS™; biotin; dioxigenin; or haptens and proteins for which antisera or monoclonal antibodies are available. The label can be directly incorporated into the polynucleotide, or it can be attached to a probe or antibody which hybridizes or binds to the polynucleotide. The labels may be coupled to the probes by any suitable means known to those of skill in the art. In various embodiments, the polynucleotides are labeled using nick translation, PCR, or random primer extension (see, e.g., Sambrook et al. supra).

In a third aspect, the present invention provides methods for diagnosing IBD and/or IBS comprising:

(a) contacting a mRNA-derived nucleic acid sample obtained from a subject suspected of having IBD or IBS under hybridizing conditions with 2 or more probes sets, wherein at least a first probe set and a second probe set selectively hybridize under high stringency conditions to a nucleic acid target selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3; wherein the first probe set and the second probe set do not selectively hybridize to the same nucleic acid;

(b) detecting formation of hybridization complexes between the 2 or more probe sets and nucleic acid targets in the nucleic acid sample, wherein a number of such hybridization complexes provides a measure of gene expression of the nucleic acid targets; and (c) diagnosing whether the subject is likely to have IBD, IBS, or neither based on the gene expression of the nucleic acid targets.

The inventors have discovered that the methods of the invention can be used, for example, in diagnosing IBD and IBS. The specific genes, probe sets, hybridizing conditions, probe types, polynucleotides, etc. are as defined above for the first and/or second aspects of the invention.

The subject is any human subject that may be suffering from IBS or IBD. As discussed above, IBS is a chronic condition characterized by abdominal pain, constipation and/or diarrhea, and/or a change in bowel habits while IBD patients may suffer from the same symptoms, as well as vomiting, hematochezia, weight loss, and/or weight gain; thus, for example, subjects with one or more of these symptoms would be candidate subjects for the methods of the invention.

As used herein, a "mRNA-derived nucleic acid sample" is a sample containing mRNA from the subject, or a cDNA (single or double stranded) generated from the mRNA obtained from the subject. The sample can be from any suitable tissue source, including but not limited to blood samples, such as PBMCs or RBC-depleted whole blood.

In one embodiment, the mRNA sample is a human mRNA sample. It will be understood by those of skill in the art that the RNA sample does not require isolation of an individual or several individual species of RNA molecules, as a complex sample mixture containing RNA to be tested can be used, such as a cell or tissue sample analyzed by in situ hybridization.

In a further embodiment, the probe sets comprise single stranded anti-sense polynucleotides of the nucleic acid compositions of the invention. For example, in mRNA fluorescence in situ hybridization (FISH) (ie. FISH to detect messenger RNA), only an anti-sense probe strand hybridizes to the single stranded mRNA in the RNA sample, and in that embodiment, the "sense" strand oligonucleotide can be used as a negative control.

Alternatively, the probe sets may comprise DNA probes. In either of these embodiments (anti-sense probes or cDNA probes), it is preferable to use controls or processes that direct hybridization to either cytoplasmic mRNA or nuclear DNA. In the absence of directed hybridization, it is preferable to distinguish between hybridization to cytoplasmic RNA and hybridization to nuclear DNA.

Any method for evaluating the presence or absence of hybridization products in the sample can be used, such as by Northern blotting methods, in situ hybridization (for example, on blood smears), polymerase chain reaction (PCR) analysis, qPCR (quantitative PCR), RT-PCR (Real Time PCR), or array based methods.

In one embodiment, detection is performed by in situ hybridization ("ISH"). In situ hybridization assays are well known to those of skill in the art. Generally, in situ hybridization comprises the following major steps (see, for example, U.S. Pat. No. 6,664,057): (1) fixation of sample or nucleic acid sample to be analyzed; (2) pre-hybridization treatment of the sample or nucleic acid sample to increase accessibility of the nucleic acid sample (within the sample in those embodiments) and to reduce nonspecific binding; (3) hybridization of the probe sets to the nucleic acid sample; (4) post-hybridization washes to remove polynucleotides not bound in the hybridization; and (5) detection of the hybridized nucleic acid fragments. The reagent used in each of these steps and their conditions for use varies depending on the particular application. In a particularly preferred embodiment, ISH is conducted according to methods disclosed in U.S. Pat. Nos. 5,750,340 and/or 6,022,689, incorporated by reference herein in their entirety.

In a typical in situ hybridization assay, cells are fixed to a solid support, typically a glass slide. The cells are typically denatured with heat or alkali and then contacted with a hybridization solution to permit annealing of labeled probes specific to the nucleic acid sequence encoding the protein. The polynucleotides of the invention are typically labeled, as discussed above. In some applications it is necessary to block the hybridization capacity of repetitive sequences. In this case, human genomic DNA or Cot-1 DNA is used to block non-specific hybridization.

When performing an in situ hybridization to cells fixed on a solid support, typically a glass slide, it is preferable to distinguish between hybridization to cytoplasmic RNA and hybridization to nuclear DNA. There are two major criteria for making this distinction: (1) copy number differences between the types of targets (hundreds to thousands of copies of RNA vs. two copies of DNA) which will normally create significant differences in signal intensities and (2) clear morphological distinction between the cytoplasm (where hybridization to RNA targets would occur) and the nucleus will make signal location unambiguous. Thus, when using double stranded DNA probes, it is preferred that the method further comprises distinguishing the cytoplasm and nucleus in cells being analyzed within the bodily fluid sample. Such distinguishing can be accomplished by any means known in the art, such as by using a nuclear stain such as Hoeschst 33342 or DAPI, which delineate the nuclear DNA in the cells being analyzed. In this embodiment, it is preferred that the nuclear stain is distinguishable from the detectable probe. It is further preferred that the nuclear membrane be maintained, i.e. that all the Hoeschst or DAPI stain be maintained in the visible structure of the nucleus.

In a further embodiment, an array-based format can be used in which the probe sets can be arrayed on a surface and the RNA sample is hybridized to the polynucleotides on the surface. In this type of format, large numbers of different hybridization reactions can be run essentially "in parallel." This embodiment is particularly useful when there are many genes whose expressions in one specimen are to be measured, or when isolated nucleic acid from the specimen, but not the intact specimen, is available. This provides rapid, essentially simultaneous, evaluation of a large number of gene expression assays. Methods of performing hybridization reactions in array based formats are also described in, for example, Pastinen (1997) Genome Res. 7:606-614; (1997) Jackson (1996) Nature Biotechnology 14:1685; Chee (1995) Science 274:610; WO 96/17958. Methods for immobilizing the polynucleotides on the surface and derivatizing the surface are known in the art; see, for example, U.S. Pat. No. 6,664,057.

In each of the above aspects and embodiments, detection of hybridization is typically accomplished through the use of a detectable label on the polynucleotides in the probe sets, such as those described above; in some alternatives, the label can be on the target nucleic acids. The label can be directly incorporated into the polynucleotide, or it can be attached to a probe or antibody which hybridizes or binds to the polynucleotide. The labels may be coupled to the probes in a variety of means known to those of skill in the art, as described above. The label can be detected by any suitable technique, including but not limited to spectroscopic, photochemical, biochemical, immunochemical, physical or chemical techniques, as discussed above.

The methods may comprise comparing gene expression of the nucleic acid targets to a control. Any suitable control known in the art can be used in the methods of the invention. For example, the expression level of a gene known to be expressed at a relatively constant level in IBS, IBD, and normal patients can be used for comparison. Alternatively, the expression level of the genes targeted by the probes can be analyzed in normal RNA samples equivalent to the test sample. Another embodiment is the use of a standard concentration curve that gives absolute copy numbers of the mRNA of the gene being assayed; this might obviate the need for a normalization control because the expression levels would be given in terms of standard concentration units. Those of skill in the art will recognize that many such controls can be used in the methods of the invention.

The methods comprise diagnosing whether the subject is likely to have IBD, IBS, or neither based on the gene expression of the nucleic acid targets. As used herein, "likely to have" means a statistically significant likelihood that the diagnosis is correct. In various embodiments, the method results in an accurate diagnosis in at least 70% of cases; more preferably of at least 75%, 80%, 85%, 90%, or more of the cases.

The methods of the present invention may apply weights, derived by various means in the art, to the number of hybridization complexes formed for each nucleic acid target. Such means can be any suitable for defining the classification rules for use of the biomarkers of the invention in diagnosing IBD or IBS. Such classification rules can be generated via any suitable means known in the art, including but not limited to supervised or unsupervised classification techniques. In a preferred embodiment, classification rules are generated by use of supervised classification techniques. As used herein, "supervised classification" is a computer-implemented process through which each measurement vector is assigned to a class according to a specified decision rule, where the possible classes have been defined on the basis of representative training samples of known identity. Examples of such supervised classification include, but are not limited to, classification trees, neural networks, k-nearest neighbor algorithms, linear discriminant analysis (LDA), quadratic discriminant analysis (QDA), and support vector machines.

In one non-limiting example, a weighted combination of the genes is arrived at by, for example, a supervised classification technique which uses the expression data from all of the genes within individual patients. The expression level of each gene in a patient is multiplied by the weighting factor for that gene, and those weighted values for each gene's expression are summed for each individual patient, and, optionally, a separate coefficient specific for that comparison is added to the sum which gives a final score. Each comparison set may result in its own specific set of gene weightings; as discussed further below, the IBD v Normal has different gene expression weightings than IBS v normal. Weightings can also have either a positive-sign or a negative-sign. Not all patients in one classification will have the same Gene 1 up, Gene 2 down, etc. (See examples below).

In various embodiments of this third aspect of the invention, the two or more probe sets comprise or consist of at least 3, 4, 5, 6, 7, 8, 9, 10, 11, 12, 13, or 14 probe sets, and wherein none of the 3-14 probe sets selectively hybridize to the same nucleic acid. These embodiments of probe sets are further discussed in the first and second aspects of the invention; all other embodiments of the probe sets and polynucleotides of the first and second aspect can be used in the methods of the invention.

In one preferred embodiment of the third aspect of the invention, at least 3, 4, or 5 of the probe sets selectively hybridize under high stringency conditions to a nucleic acid selected from the group consisting of TH1L, HIST1H2BK, UBE2G1, BLCAP, and CALM3. As disclosed in more detail below, this method can be used in preferred embodiments of the methods of the invention for distinguishing normal subjects from those subjects suffering from IBS. Examples of such preferred probe sets for use in the methods of the invention are provided in Table 17. In one preferred version of this embodiment, is a method for diagnosing irritable bowel syndrome (IBS), comprising:

(a) contacting a mRNA-derived nucleic acid sample obtained from a subject suspected of having IBS under hybridizing conditions with at least 3 nucleotide probes, wherein a first nucleotide probe, a second nucleotide probe, and a third nucleotide probe each consist of 15 or more contiguous nucleotides of a nucleic acid target selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), or a full complement thereof, wherein each of the first, second, and third nucleotide probes consist of 15 or more contiguous nucleotides of a different nucleic acid target;

(b) detecting formation of hybridization complexes between the probes and the nucleic acid targets in the nucleic acid sample, wherein a number of such hybridization complexes provides a measure of gene expression of the nucleic acid targets; and (c) diagnosing whether the subject is likely to have IBS based on the measure of gene expression of the nucleic acid targets. In a further preferred version of this embodiment, the nucleic acid targets comprise BLCAP, TH1L, UBE2G1, and HIST1H2BK. In a further preferred version of this embodiment, the subject suffers from one or more of abdominal pain, constipation, diarrhea, and a change in bowel habits. In another version of this embodiment, the mRNA-derived nucleic acid sample is obtained from peripheral blood mononuclear cells red blood cell-depleted whole blood. In a further version of this embodiment, the method further comprises analyzing gene expression of the nucleic acid targets by applying a weight to the number of hybridization complexes formed for each nucleic acid target.

In another preferred embodiment of the third aspect of the invention, at least 5 or 6 of the probe sets selectively hybridize under high stringency conditions to a nucleic acid selected from the group consisting of RAP1A, BLCAP, UBE2G1, GPX1, CALM3, and NONO. As disclosed in more detail below, such probe sets can be used in preferred embodiments of the methods of the invention for distinguishing normal subjects from those subjects suffering from IBD. Examples of such preferred probe sets for use in the methods of the invention are provided in Table 18. In one preferred version of this embodiment, the method comprises:

(a) contacting a mRNA-derived nucleic acid sample obtained from a subject suspected of having IBD under hybridizing conditions with at least 5 nucleotide probes, wherein a first nucleotide probe, a second nucleotide probe, a third nucleotide probe, a fourth nucleotide probe, and a fifth nucleotide probe each consist of 15 or more contiguous nucleotides of a nucleic acid target selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof, wherein each of the first, second, third, fourth, and fifth nucleotide probes consist of 15 or more contiguous nucleotides of a different nucleic acid target;

(b) detecting formation of hybridization complexes between the nucleotide probes and the nucleic acid targets in the nucleic acid sample, wherein a number of such hybridization complexes provides a measure of gene expression of the nucleic acid targets; and (c) diagnosing whether the subject is likely to have IBD based on the measure of gene expression of the nucleic acid targets. In a further preferred embodiment, the nucleic acid targets comprise RAP1A, BLCAP, UBE2G1, CALM3, GPX1, and NONO. In another embodiment, the subject may be suffering from one or more of abdominal pain, constipation, diarrhea, a change in bowel habits, vomiting, hematochezia, and weight change. In a further embodiment, the mRNA-derived nucleic acid sample is obtained from peripheral blood mononuclear cells or red blood cell-depleted whole blood. In a further embodiment, the method further comprises analyzing gene expression of the nucleic acid targets by applying a weight to the number of hybridization complexes formed for each nucleic acid target.

In a further preferred embodiment of the third aspect of the invention, at least 6 or 7 of the probe sets selectively hybridize under high stringency conditions to a nucleic acid selected from the group consisting of RAP1A, BLCAP, UBE2G1, CALM3, GPX1, HIST1H2BK, and PPP2R5A. As disclosed in more detail below, such probe sets can be used in preferred embodiments of the methods of the invention for distinguishing those subjects suffering from IBS from those subjects suffering from IBD. Examples of such preferred probe sets for use in the methods of the invention are provided in Table 19. In one preferred version, of this embodiment, a method for differentiating between inflammatory bowel disease (IBD) and irritable bowel syndrome (IBS) in a subject, comprises:

(a) contacting a mRNA-derived nucleic acid sample obtained from a subject suspected of having IBD under hybridizing conditions with at least 6 nucleotide probes, wherein a first nucleotide probe, a second nucleotide probe, a third nucleotide probe, a fourth nucleotide probe, a fifth nucleotide probe, and a sixth nucleotide probe each consist of 15 or more contiguous nucleotides of a nucleic acid target selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof; wherein each of the first, second, third, fourth, fifth, and sixth nucleotide probes consist of 15 or more contiguous nucleotides of a different nucleic acid target;

(b) detecting formation of hybridization complexes between the nucleotide probes and the nucleic acid targets in the nucleic acid sample, wherein a number of such hybridization complexes provides a measure of gene expression of the nucleic acid targets; and (c) diagnosing whether the subject is likely to have IBD or IBS based on the measure of gene expression of the nucleic acid targets. In a further preferred embodiment, the nucleic acid targets comprise RAP1A, UBE2G1, CALM3, GPX1, HIST1H2BK, PPP2R5A, and BLCAP. In another embodiment, the subject suffers from one or more of abdominal pain, constipation, diarrhea, a change in bowel habits, vomiting, hematochezia, and weight change. In a further embodiment, the mRNA-derived nucleic acid sample is obtained from peripheral blood mononuclear cells or red blood cell-depleted whole blood. In another embodiment, the method further comprises analyzing gene expression of the nucleic acid targets by applying a weight to the number of hybridization complexes formed for each nucleic acid target.

In one specific embodiment of this third aspect of the invention, the methods comprise use of a first probe set that selectively hybridizes under high stringency conditions to BLCAP, a second probe set that selectively hybridizes under high stringency conditions to TH1L, a third probe set that selectively hybridizes under high stringency conditions to CALM3, and a fourth probe set that selectively hybridizes under high stringency conditions to HIST1H2BK. As disclosed in more detail below, the inventors have discovered that such methods can be used to distinguish between normal and IBS patients.

In a second specific embodiment of this third aspect of the invention, the methods comprise use of a first probe set that selectively hybridizes under high stringency conditions to BLCAP, a second probe set that selectively hybridizes under high stringency conditions to TH1L, a third probe set that selectively hybridizes under high stringency conditions to UBE2G1, and a fourth probe set that selectively hybridizes under high stringency conditions to HIST1H2BK. As disclosed in more detail below, the inventors have discovered that such methods can be used to distinguish between normal and IBS patients.

In a third specific embodiment of this third aspect of the invention, the methods comprise use of a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to GPX1. As disclosed in more detail below, the inventors have discovered that such methods can be used as probes to distinguish between normal and IBD patients.

In a fourth specific embodiment of this third aspect of the invention, the methods comprise use of a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to CALM3, and a fifth probe set that selectively hybridizes under high stringency conditions to GPX1. As disclosed in more detail below, the inventors have discovered that such methods can distinguish between normal and IBD patients.

In a fifth specific embodiment of this third aspect of the invention, the methods comprise use of a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to CALM3, a fifth probe set that selectively hybridizes under high stringency conditions to GPX1, and a sixth probe set that selectively hybridizes under high stringency conditions to NONO. As disclosed in more detail below, the inventors have discovered that such methods can distinguish between normal and IBD patients.

In a sixth specific embodiment of this third aspect of the invention, the methods comprise use of a first probe set that selectively hybridizes under high stringency conditions to RAP1A, a second probe set that selectively hybridizes under high stringency conditions to BLCAP, a third probe set that selectively hybridizes under high stringency conditions to UBE2G1, a fourth probe set that selectively hybridizes under high stringency conditions to CALM3, a fifth probe set that selectively hybridizes under high stringency conditions to GPX1, a sixth probe set that selectively hybridizes under high stringency conditions to HIST1H2BK, and a seventh probe set that selectively hybridizes under high stringency conditions to PPP2RR5A. As disclosed in more detail below, the inventors have discovered that such methods can distinguish normal and IBS patients from IBD patients.

In a seventh specific embodiment of this third aspect of the invention, the methods comprise use of a first probe set that selectively hybridizes under high stringency conditions to RAP1A, a second probe set that selectively hybridizes under high stringency conditions to UBE2G1, a third probe set that selectively hybridizes under high stringency conditions to CALM3, a fourth probe set that selectively hybridizes under high stringency conditions to GPX1, a fifth probe set that selectively hybridizes under high stringency conditions to HIST1H2BK1, and a sixth probe set that selectively hybridizes under high stringency conditions to PPP2R5A. As disclosed in more detail below, the inventors have discovered that such methods can be used as probes to distinguish IBS patients from IBD patients.

In an eighth specific embodiment of this third aspect of the invention, the methods comprise use of a first probe set that selectively hybridizes under high stringency conditions to RAP1A, a second probe set that selectively hybridizes under high stringency conditions to UBE2G1, a third probe set that selectively hybridizes under high stringency conditions to CALM3, a fourth probe set that selectively hybridizes under high stringency conditions to GPX1, a fifth probe set that selectively hybridizes under high stringency conditions to HIST1H2BK, a sixth probe set that selectively hybridizes under high stringency conditions to PPP2R5A, and a seventh probe set that selectively hybridizes under high stringency conditions to BLCAP. As disclosed in more detail below, the inventors have discovered that such methods can be used as probes to distinguish IBS patients from IBD patients.

In a ninth specific embodiment of this third aspect of the invention, the methods comprise use of a first probe set that selectively hybridizes under high stringency conditions to BLCAP, a second probe set that selectively hybridizes under high stringency conditions to CALM3, a third probe set that selectively hybridizes under high stringency conditions to GPX1, a fourth probe set that selectively hybridizes under high stringency conditions to TH1L, a fifth probe set that selectively hybridizes under high stringency conditions to RAP1A, and a sixth probe set that selectively hybridizes under high stringency conditions to NONO. As disclosed in more detail below, the inventors have discovered that such methods can be used as probes to distinguish IBS and IBD patients from normal patients.

In a fourth aspect, the present invention provides methods method for diagnosing IBD and/or IBS comprising:

(a) contacting a mRNA-derived nucleic acid sample obtained from a subject suspected of having IBD or IBS under amplifying conditions with 2 or more primer pairs, wherein at least a first primer pair and a second primer pair are capable of selectively amplifying a detectable portion of a nucleic acid target selected from the group consisting of TH1L, HIST1H2AC, TFE3, HIST1H2BK, UBE2G1, NONO, PCBP1, RAP1A, PPP2R5A, PGRMC1, BLCAP, GPX1, HMGB1, and CALM3; wherein the first primer pair and the second primer pair do not selectively amplify the same nucleic acid;

(b) detecting amplification products generated by amplification of nucleic acid targets in the nucleic acid sample by the two or more primer pairs, wherein the amplification products provide a measure of gene expression of the nucleic acid targets; and (c) diagnosing whether the subject is likely to have IBD, IBS, or neither based on the amplification of the nucleic acid targets.

Definitions of primer pairs as used above apply to this aspect of the invention, as well as all other common terms. All embodiments disclosed above for the other aspects of the invention are also suitable for this fourth aspect.

In these methods, amplification of target nucleic acids using the primer pairs is used instead of hybridization to detect gene expression products. Any suitable amplification technique can be used, including but not limited to PCR, RT-PCT, qPCR, spPCR, etc. Suitable amplification conditions can be determined by those of skill in the art based on the particular primer pair design and other factors, based on the teachings herein. In various embodiments, the two or more primer pairs comprise at least 3-14 primer pairs, wherein none of the 3-14 primer pairs selectively amplify the same nucleic acid.

In one preferred embodiment of the fourth aspect of the invention, at least 3, 4, or 5 of the primer pairs selectively amplify a detectable portion of a nucleic acid selected from the group consisting of TH1L, HIST1H2BK, UBE2G1, BLCAP, and CALM3. As disclosed in more detail below, such primer pairs can be used in preferred embodiments of the methods of the invention for distinguishing normal subjects from those subjects suffering from IBS. Examples of such preferred primer pairs are those that amplify a detectable portion of the nucleic acids provided in Table 17. In one preferred version of this embodiment, a method for diagnosing irritable bowel syndrome (IBS) comprises:

(a) contacting a mRNA-derived nucleic acid sample obtained from a subject suspected of having IBS under amplifying conditions with at least three primer pairs, wherein a first primer pair, a second primer pair, and a third primer pair selectively amplify a different nucleic acid target selected from the group consisting of SEQ ID NO:4 (TH1L), SEQ ID NO:9 (HIST1H2BK), SEQ ID NO:5 (UBE2G1), SEQ ID NO:3 (BLCAP), and SEQ ID NO:6 (CALM3), or a full complement thereof, wherein each primer in each primer pair consists of at least 15 contiguous nucleotides of its respective nucleic acid target;

(b) detecting amplification products generated by amplification of nucleic acid targets in the nucleic acid sample by the at least three primer pairs, wherein a number of such amplification products provides a measure of gene expression of the nucleic acid targets; and (c) diagnosing whether the subject is likely to have IBS based on the measure of gene expression of the nucleic acid targets. In a further version of this embodiment, the nucleic acid targets comprise BLCAP, TH1L, UBE2G1, and HIST1H2BK. In another version, the subject suffers from one or more of abdominal pain, constipation, diarrhea, and a change in bowel habits. The mRNA-derived nucleic acid sample may be obtained from peripheral blood mononuclear cells red blood cell-depleted whole blood. The method may further comprise analyzing gene expression of the nucleic acid targets by applying a weight to the number of amplification products formed for each nucleic acid target.

In another preferred embodiment of the fourth aspect of the invention, at least 5 or 6 of the primer pairs selectively amplify a detectable portion of a nucleic acid selected from the group consisting of RAP1A, BLCAP, UBE2G1, GPX1, CALM3, and NONO. As disclosed in more detail below, such primer pairs can be used in preferred embodiments of the methods of the invention for distinguishing normal subjects from those subjects suffering from IBD. Examples of such preferred primer pairs are those that amplify a detectable portion of the nucleic acids provided in Table 18. In a preferred embodiment, the method for IBD diagnosis comprises (a) contacting a mRNA-derived nucleic acid sample obtained from a subject suspected of having IBD under amplifying conditions with at least five primer pairs, wherein a first primer pair, a second primer pair, a third primer, a fourth primer pair, and a fifth primer pair each selectively amplify a different nucleic acid target selected from the group consisting of SEQ ID NO:1 and/or 2 (RAP1A), SEQ ID NO:3 (BLCAP), SEQ ID NO:5 (UBE2G1), SEQ ID NO:6 (CALM3), SEQ ID NO:7 and/or 8 (GPX1), and SEQ ID NO:13 (NONO), or a full complement thereof, wherein each primer in each primer pair consists of at least 15 contiguous nucleotides of its respective nucleic acid target;

(b) detecting amplification products generated by amplification of nucleic acid targets in the nucleic acid sample by the at least five primer pairs, wherein a number of such amplification products provides a measure of gene expression of the nucleic acid targets; and (c) diagnosing whether the subject is likely to have IBD based on the measure of gene expression of the nucleic acid targets. In a further preferred embodiment, the nucleic acid targets comprise RAP1A, BLCAP, UBE2G1, CALM3, GPX1, and NONO. In another embodiment, the subject suffers from one or more of abdominal pain, constipation, diarrhea, a change in bowel habits, vomiting, hematochezia, and weight change. In a further embodiment, the mRNA-derived nucleic acid sample is obtained from peripheral blood mononuclear cells or red blood cell-depleted whole blood. In another embodiment, the method further comprises analyzing gene expression of the nucleic acid targets by applying a weight to the number of amplification products formed for each nucleic acid target.

In a further preferred embodiment of the fourth aspect of the invention, at least 6 or 7 of the primer pairs selectively amplify a detectable portion of a nucleic acid selected from the group consisting of RAP1A, BLCAP, UBE2G1, CALM3, GPX1, HIST1H2BK, and PPP2R5A. As disclosed in more detail below, such primer pairs can be used in preferred embodiments of the methods of the invention for distinguishing those subjects suffering from IBS from those subjects suffering from IBD. Examples of such preferred primer pairs are those that amplify a detectable portion of the nucleic acids provided in Table 19. In one preferred version, method for differentiating between inflammatory bowel disease (IBD) and irritable bowel syndrome (IBS) in a subject comprises:

(a) contacting a mRNA-derived nucleic acid sample obtained from a subject suspected of having IBD under amplifying conditions with at least six primer pairs, wherein a first primer pair, a second primer pair, a third primer, a fourth primer pair, a fifth primer pair, and a sixth primer pair each selectively amplify a different nucleic acid target selected from the group consisting of SEQ ID NO:1 and/or 2 (RAP1A), SEQ ID NO:5 (UBE2G1), SEQ ID NO:6 (CALM3), SEQ ID NO:7 and/or 8 (GPX1), SEQ ID NO:9 (HIST1H2BK), SEQ ID NO:10 (PPP2R5A), and SEQ ID NO:3 (BLCAP), or a full complement thereof, wherein each primer in each primer pair consists of at least 15 contiguous nucleotides of its respective nucleic acid target;

(b) detecting amplification products generated by amplification of nucleic acid targets in the nucleic acid sample by the at least six primer pairs, wherein a number of such amplification products provides a measure of gene expression of the nucleic acid targets; and (c) diagnosing whether the subject is likely to have IBD or IBS based on the measure of gene expression of the nucleic acid targets. In a preferred embodiment, the nucleic acid targets comprise RAP1A, UBE2G1, CALM3, GPX1, HIST1H2BK, PPP2R5A, and BLCAP. In a further embodiment, the subject suffers from one or more of abdominal pain, constipation, diarrhea, a change in bowel habits, vomiting, hematochezia, and weight change. In another embodiment, the mRNA-derived nucleic acid sample is obtained from peripheral blood mononuclear cells or red blood cell-depleted whole blood. In a further embodiment, the method further comprises analyzing gene expression of the nucleic acid targets by applying a weight to the number of amplification products formed for each nucleic acid target.

In one specific embodiment of this fourth aspect of the invention, the methods comprise use of a first primer pair that selectively amplifies a detectable portion of BLCAP, a second primer pair that selectively amplifies a detectable portion of TH1L, a third primer pair that selectively amplifies a detectable portion of CALM3, and a fourth primer pair that selectively amplifies a detectable portion of HIST1H2BK. As disclosed in more detail below, the inventors have discovered that such methods can distinguish between normal and IBS patients.

In a second specific embodiment of this fourth aspect of the invention, the methods comprise use of a first primer pair that selectively amplifies a detectable portion of BLCAP, a second primer pair that selectively amplifies a detectable portion of TH1L, a third primer pair that selectively amplifies a detectable portion of UBE2G1, and a fourth primer pair that selectively amplifies a detectable portion of HIST1H2BK. As disclosed in more detail below, the inventors have discovered that such methods can distinguish between normal and IBS patients.

In a third specific embodiment of this fourth aspect of the invention, the methods comprise use of a first primer pair that selectively amplifies a detectable portion of RAP1A, a second primer pair that selectively amplifies a detectable portion of BLCAP, a third primer pair that selectively amplifies a detectable portion of UBE2G1, and a fourth primer pair that selectively amplifies a detectable portion of GPX1. As disclosed in more detail below, the inventors have discovered that such methods can be used as probes to distinguish between normal and IBD patients.

In a fourth specific embodiment of this fourth aspect of the invention, the methods comprise use of a first primer pair that selectively amplifies a detectable portion of RAP1A, a second primer pair that selectively amplifies a detectable portion of BLCAP, a third primer pair that selectively amplifies a detectable portion of UBE2G1, a fourth primer pair that selectively amplifies a detectable portion of CALM3, and a fifth primer pair selectively amplifies a detectable portion of GPX1. As disclosed in more detail below, the inventors have discovered that such methods can distinguish between normal and IBD patients.

In a fifth specific embodiment of this fourth aspect of the invention, the methods comprise use of a first primer pair that selectively amplifies a detectable portion of RAP1A, a second primer pair that selectively amplifies a detectable portion of BLCAP, a third primer pair that selectively amplifies a detectable portion of UBE2G1, a fourth primer pair that selectively amplifies a detectable portion of CALM3, a fifth primer pair selectively amplifies a detectable portion of GPX1, and a sixth primer pair selectively amplifies a detectable portion of NONO. As disclosed in more detail below, the inventors have discovered that such methods can distinguish between normal and IBD patients.

In a sixth specific embodiment of this fourth aspect of the invention, the methods comprise use of a primer pair that selectively amplifies a detectable portion of RAP1A, a second primer pair that selectively amplifies a detectable portion of BLCAP, a third primer pair that selectively amplifies a detectable portion of UBE2G1, a fourth primer pair that selectively amplifies a detectable portion of CALM3, a fifth primer pair that selectively amplifies a detectable portion of GPX1, a sixth primer pair that selectively amplifies a detectable portion of HIST 1 H2BK; and a seventh primer pair selectively that amplifies a detectable portion of PPP2RR5A. As disclosed in more detail below, the inventors have discovered that such methods can distinguish normal and IBS patients from IBD patients.

In a seventh specific embodiment of this fourth aspect of the invention, the methods comprise use of a first primer pair that selectively amplifies a detectable portion of RAP1A, a second primer pair that selectively amplifies a detectable portion of UBE2G1, a third primer pair that selectively amplifies a detectable portion of CALM3, a fourth primer pair that selectively amplifies a detectable portion of GPX1, a fifth primer pair selectively amplifies a detectable portion of HIST1H2BK, and a sixth primer pair selectively amplifies a detectable portion of PPP2R5A. As disclosed in more detail below, the inventors have discovered that such methods can be used to distinguish between IBS patients and IBD patients In an eighth specific embodiment of this fourth aspect of the invention, the methods comprise use of a primer pair that selectively amplifies a detectable portion of RAP1A, a second primer pair that selectively amplifies a detectable portion of UBE2G1, a third primer pair that selectively amplifies a detectable portion of CALM3, a fourth primer pair that selectively amplifies a detectable portion of GPX1, a fifth primer pair that selectively amplifies a detectable portion of HIST 1H2BK, a sixth primer pair that selectively amplifies a detectable portion of PPP2R5A, and a seventh primer pair selectively that amplifies a detectable portion of BLCAP. As disclosed in more detail below, the inventors have discovered that such methods can be used as probes to distinguish IBS patients from IBD patients.

In a ninth specific embodiment of this fourth aspect of the invention, the methods comprise use of a first primer pair that selectively amplifies a detectable portion of BLCAP, a second primer pair that selectively amplifies a detectable portion of CALM3, a third primer pair that selectively amplifies a detectable portion of GPX1, a fourth primer pair that selectively amplifies a detectable portion of TH1L, a fifth primer pair selectively amplifies a detectable portion of RAP1A, and a sixth primer pair selectively amplifies a detectable portion of NONO. As disclosed in more detail below, the inventors have discovered that such methods can be used as probes to distinguish IBS and IBD patients from normal patients.

In various embodiments, the methods may further comprise comparing amplification products to a control.

In a further embodiment of all of the methods of the invention, the methods are automated, and appropriate software is used to conduct some or all stages of the method.

In a further aspect, the present invention provides kits for use in the methods of the invention, comprising the biomarkers and/or primer pair sets of the invention and instructions for their use. In a preferred embodiment, the polynucleotides are detectably labeled, most preferably where the detectable labels on each polynucleotide in a given probe set or primer pair are the same, and differ from the detectable labels on the polynucleotides in other probe sets or primer pairs, as disclosed above. In a further preferred embodiment, the probes/primer pairs are provided in solution, most preferably in a hybridization or amplification buffer to be used in the methods of the invention. In further embodiments, the kit also comprises wash solutions, pre-hybridization solutions, amplification reagents, software for automation of the methods, etc.

EXAMPLE 1

In an effort to identify gene expression profiles that could discriminate between whole blood samples collected from IBS, IBD, and normal patients, and thus provide the basis for a minimally invasive diagnostic test, we employed a proprietary data mining program to analyze publicly available data collected from Crohn's Disease (CD) and Ulcerative Colitis (UC) patients (Burczynski et al., Molecular Classification of Crohn's Disease and Ulcerative Colitis Patients Using Transcriptional Profiles in Peripheral Blood Mononuclear Cells, Journal of Molecular Diagnostics 8(1):51-61, February 2006), hereinafter referred to as the "Burczynski data."

The Burczynski data consisted of a set of individual expression level features, each feature being a quantitative fluorescent signal derived from a single microarray spot. As detailed in Burczynski et al (2006), the signals were generated by hybridizing fluorescently-labeled RNA from a single patient to all of the spots on a single DNA-based oligonucleotide microarray. From these data, we identified molecular signatures, comprised of sets of expression level features, that effectively differentiated between IBD patients and unaffected normal control subjects. Expression levels of the genes represented by those array features were then measured in a prospectively ascertained sample of patients (the 'pilot study', described below). The Burczynski discovery dataset consisted of 127 separate Affymetrix microarray hybridization experiments on RNA from 26 Ulcerative Colitis patients, 59 Crohn's Disease patients, and 42 normal controls.

We employed our proprietary data mining program to analyze the publicly available Burczynski data. We randomly divided the patients in the Burczynski dataset for purposes of our analysis into 2 approximately equal groups: a training set for biomarker set discovery and a separate non-overlapping test set for assessment of biomarkers discovered from the training set. The training set consisted of 30 CD patients, 13 UC patients, and 21 normal controls. The test set consisted of 29 CD patients, 13 UC patients, and 21 controls. The CD and UC patients were defined as 'affected', and normal controls were defined as 'unaffected'.

Our proprietary data mining program was then used to perform a genetic-algorithm search of expression level data for combinations across the affected and unaffected patient sets. The number of features constituting a marker set combination was fixed at 4. The Burczynski data set contained 22,283 expression level features; the number of 4-wise combinations of features in that data set are: (!22,283/(!4*!22,279)=10,269,905,646,716,170.

The proprietary data mining program was run 3 separate times on the Burczynski dataset using three specific sets of parameters. (1) One parameter set used the training and test sets defined above with additional settings that gave computational results weighted towards higher sensitivity (to minimize false negatives), (2) the second set was similarly weighted towards higher specificity (to minimize false positives), and (3) the third set used random cross-validation ('bootstrap') with no weighting towards either specificity or sensitivity. Each 4-feature combination analyzed was assigned a score that characterized its accuracy in discriminating between the affected and unaffected groups. The score for each combination of expression features ranges from 1.00 for completely accurate to 0.00 for completely inaccurate.

For the set weighted towards higher sensitivity (set 1), the top-scoring 4-feature sets were obtained such that a combination's score on the training set was greater than 0.995, or the combination's score on the test set was greater than 0.92. For the set weighted towards higher specificity (set 2), the top-scoring 4-feature sets were obtained such that a combination's score on the training set was greater than 0.9975, or the combination's score on the test set was greater than 0.92. For the bootstrap result set with equal weighting between sensitivity and specificity (set 3), the top-scoring 4-feature sets were obtained such that a combination's score on the training set was greater than 0.995 (ie: approximately 99.5% accuracy).

Significance of the marker sets was assessed empirically by random iterative relabeling. The affected and unaffected statuses of patients were randomly re-assigned, and the proprietary data mining program was then run to determine the top marker solutions for the randomly labeled set. This was repeated to obtain 100,000 marker sets. In the randomly relabeled sets, the training set scores reached a maximum of 0.927; 95% of solutions (the empirical p=0.05 level) scored at or below 0.882, and 99% of solutions the empirical p=0.01 level) scored at or below 0.893. The test set scores in relabeled solutions reached a maximum of 0.915; 95% of solutions (the empirical p=0.05 level) scored at or below 0.753, and 99% of solutions (the empirical p=0.01 level) scored at or below 0.809.

A total of sixteen sets, each comprised of 4 features (in the Burczynski microarray data, some genes are represented by more than 1 feature and some features hybridize to more than 1 gene), was obtained using a combination of thresholds: the score on the training set was greater than 0.9975 and/or the score on the test set was greater than 0.92.

Table 2 contains the combinations of genes that were identified from the gene expression profile of peripheral blood mononuclear cells that effectively differentiate between IBD patients and unaffected normal control subjects.

TABLE 2

Top 16 4-gene combinations

| Combination | Gene 1 | Gene 2 | Gene 3 | Gene 4 |
|---|---|---|---|---|
| 1 | HIST1H2BK | NONO | PPP2R5A | BLCAP |
| 2 | TH1L | PPP2R5A | PGRMC1 | BLCAP |
| 3 | TH1L | UBE2G1 | PPP2R5A | BLCAP |
| 4 | TH1L | PPP2R5A | BLCAP | HMGB1 |
| 5 | HIST1H2BK | RAP1A | PPP2R5A | BLCAP |
| 6 | NONO | PPP2R5A | BLCAP | GPX1 |
| 7 | HIST1H2AC | RAP1A | PPP2R5A | HMGB1 |
| 8 | TH1L | TFE3 | UBE2G1 | BLCAP |
| 9 | PCBP1 | RAP1A | PPP2R5A | PGRMC1 |
| 10 | NONO | UBE2G1 | PPP2R5A | BLCAP |
| 11 | TH1L | HIST1H2AC | PPP2R5A | BLCAP |
| 12 | UBE2G1 | PPP2R5A | BLCAP | GPX1 |
| 13 | HIST1H2AC | PPP2R5A | BLCAP | GPX1 |
| 14 | TH1L | PPP2R5A | BLCAP | CALM3 |
| 15 | TH1L | RAP1A | PPP2R5A | CALM3 |
| 16 | TH1L | HIST1H2BK | PPP2R5A | BLCAP |

Fourteen individual expression array features constitute those 16 sets. The feature sets and their memberships are indicated in Table 3 below. Each feature represents the expression level of a transcript from a single gene; the HUGO gene names for each feature are indicated. The average fold-difference in expression between the IBD and normal groups is also shown, computed by dividing the average expression level in IBD patients by the average expression level in Normal patients. A fold-difference greater than 1 indicates the gene has higher expression in IBD patients compared to normal patients, while a fold-difference less than 1 indicates the gene has lower expression in IBD patients compared to normal patients. The row labeled "freq" shows how many times that microarray feature occurs in the top 16 marker sets.

TABLE 3

Gene frequency in top 16 combinations

| | HGNC name | | | | | | |
|---|---|---|---|---|---|---|---|
| | PPP2R5A | BLCAP | TH1L | UBE2G1 | RAP1A | HIST1H2AC | HIST1H2BK |
| IBD/NML fold diff | 0.76 | 0.72 | 0.70 | 0.76 | 1.60 | 2.13 | 1.94 |
| Feature # | 20569 | 21724 | 2313 | 13649 | 20394 | 7839 | 12991 |
| freq | 15 | 13 | 8 | 4 | 4 | 3 | 3 |
| 14 genes in 16 sets | X | X | | | | | X |
| | X | X | X | | | | |
| | X | X | X | X | | | |
| | X | X | X | | | | |
| | X | X | | | X | | X |
| | X | X | | | | | |
| | X | | | | X | X | |
| | | X | X | X | | | |
| | X | | | | X | | |
| | X | X | | X | | | |
| | X | X | X | | | X | |
| | X | X | | X | | | |
| | X | X | | | | X | |
| | X | X | X | | | | |
| | X | | X | | X | | |
| | X | X | X | | | | X |

TABLE 3-continued

Gene frequency in top 16 combinations

| | HGNC name | | | | | | |
|---|---|---|---|---|---|---|---|
| | GPX1 | NONO | PGRMC1 | HMGB1 | CALM3 | TFE3 | PCBP1 |
| IBD/NML fold diff | 1.80 | 0.78 | 1.70 | 0.72 | 1.42 | 1.41 | 1.31 |
| Feature # | 22020 | 12337 | 21635 | 22076 | 22134 | 10442 | 14167 |
| freq | 3 | 3 | 2 | 2 | 2 | 1 | 1 |
| 14 genes in 16 sets | | X | | | | | |
| | | | X | | | | |
| | | | | X | | | |
| | X | X | | | | | |
| | | | | X | | | |
| | | | | | | X | |
| | | | | X | | | X |
| | | X | | | | | |
| | X | | | | | | |
| | X | | | | | | |
| | | | | | X | | |
| | | | | | X | | |

A gene list (Table 4) was derived from an analysis (Table 3) of the unique set of genes in these combinations.

TABLE 4

Gene List

| gene name | affy # | Hs.ID | gene description |
|---|---|---|---|
| TH1L | 220607_x_at | Hs.517148 | TH1-like (*Drosophila*) |
| HIST1H2AC | 215071_s_at | Hs.484950 | histone 1, H2ac |
| TFE3 | 212457_at | Hs.274184 | Transcription factor binding to IGHM enhancer 3 |
| NONO | 210470_x_at | Hs.533282 | Non-POU domain containing, octamer-binding |
| HIST1H2BK | 209806_at | Hs.437275 | Histone 1, H2bk |
| UBE2G1 | 209141_at | Hs.462035 | Ubiquitin-conjugating enzyme E2G 1 (UBC7 homolog, *C. elegans*) |
| PCBP1 | 208620_at | Hs.2853 | Poly(rC) binding protein 1 |
| RAP1A | 202362_at | Hs.190334 | RAP1A, member of RAS oncogene family |
| PPP2R5A | 202187_s_at | Hs.497684 | Protein phosphatase 2, regulatory subunit B (B56), alpha isoform |
| PGRMC1 | 201121_s_at | Hs.90061 | Progesterone receptor membrane component 1 |
| BLCAP | 201032_at | Hs.472651 | Bladder cancer associated protein |
| GPX1 | 200736_s_at | Hs.76686 | Glutathione peroxidase 1 |
| HMGB1 | 200680_x_at | Hs.434102 | High-mobility group box 1 |
| CALM3 | 200622_x_at | Hs.515487 | Calmodulin 3 (phosphorylase kinase, delta) |

An example of the diagnostic performance of the discovery biomarker sets on the analyzed dataset is shown in FIG. 1. A logistic regression was performed with the patient's affected/unaffected status against the quantitative levels of the four features from a discovery marker set. The training set patient data were used to perform the regression analysis. The resulting regression coefficients were then used to calculate a weighted sum of the expression levels of the four features in the test set patients. The resulting weighted-sum regression score for each training set patient was then plotted, with IBD patients having open symbols and Normal patients having filled symbols. In the example shown in the graph below, a regression-score cutoff of approximately 2.75 assigns an 'affected' test result to 40 patients with IBD and to 1 Normal patient. An 'unaffected' result is assigned to 2 patients with IBD and 20 Normal patients. Using standard calculations for medical diagnostics, this gives Sensitivity=40/42=0.952, Specificity=20/21=0.952, Positive Predictive Value=40/41=0.976, and Negative Predictive Value=20/22=0.909.

EXAMPLE 2

Eight of the genes listed in Table 4 that occurred frequently in the top sets shown in Table 3 were evaluated, along with Actin B as a control gene, in a subsequent study on a total of 482 RBC (red blood cell)-depleted whole blood samples from: 98 normal controls, 91 Ulcerative Colitis patients, 98 Crohn's Disease patients, 98 IBS patients and 97 patients with non-gastrointestinal inflammatory disease. Samples were obtained from 7 clinical sites at various geographic locations within the U.S.A. In the analysis there was no distinction made between Crohn's and UC.

The RNA expression levels of eight genes from among the 14 features in the top discovery marker sets were measured by quantitative real-time PCR in the RBC-depleted whole blood of a prospectively ascertained sample of affected patients and unaffected controls. An additional ninth gene was measured to serve as an internal reference standard across patients. Five cohorts of patients had RNA assayed:

98 Normal
    98 Crohn's Disease
    91 Ulcerative Colitis
    98 Irritable Bowel Syndrome
    97 Non-Gastrointestinal Inflammatory Disease The 9 genes (including 1 control) assayed for RNA expression levels in the 5 cohorts of patients were: (Human Genome Organization (HUGO) Gene Nomenclature Committee names are given)

RAP1A
    BLCAP
    PPP2R5A
    UBE2G1
    GPX1
    TH1-L
    CALM3
    HIST1H2BK
    ACTB (the internal reference gene)

Whole blood samples and clinical information were obtained from all patients. Each IBD patient was diagnosed by a board-certified gastroenterologist; IBD diagnoses were confirmed by endoscopy. Each IBS patient was diagnosed by a board-certified gastroenterologist using Rome I criteria. All protocols were IRB approved; informed consent was obtained and peripheral blood samples and clinical data were collected from all patients. RNA was isolated, cDNA was synthesized, and quantitative real-time PCR for each gene was performed on an Applied Biosystems 7300 Real-Time PCR System. Expression levels were output as Ct (cycle or crossing threshold). DeltaCts of each gene for each patient were computed to normalize gene expression levels of the 8 marker genes to the intra-subject reference gene (ACTB also referred to as β-Actin). DeltaCt=Ct[marker gene]−Ct[ACTB]. The DeltaCts were then used for analysis of diagnostic classification performance.

2A. IBD vs. Normal 5-Gene Combination

Figure 2:
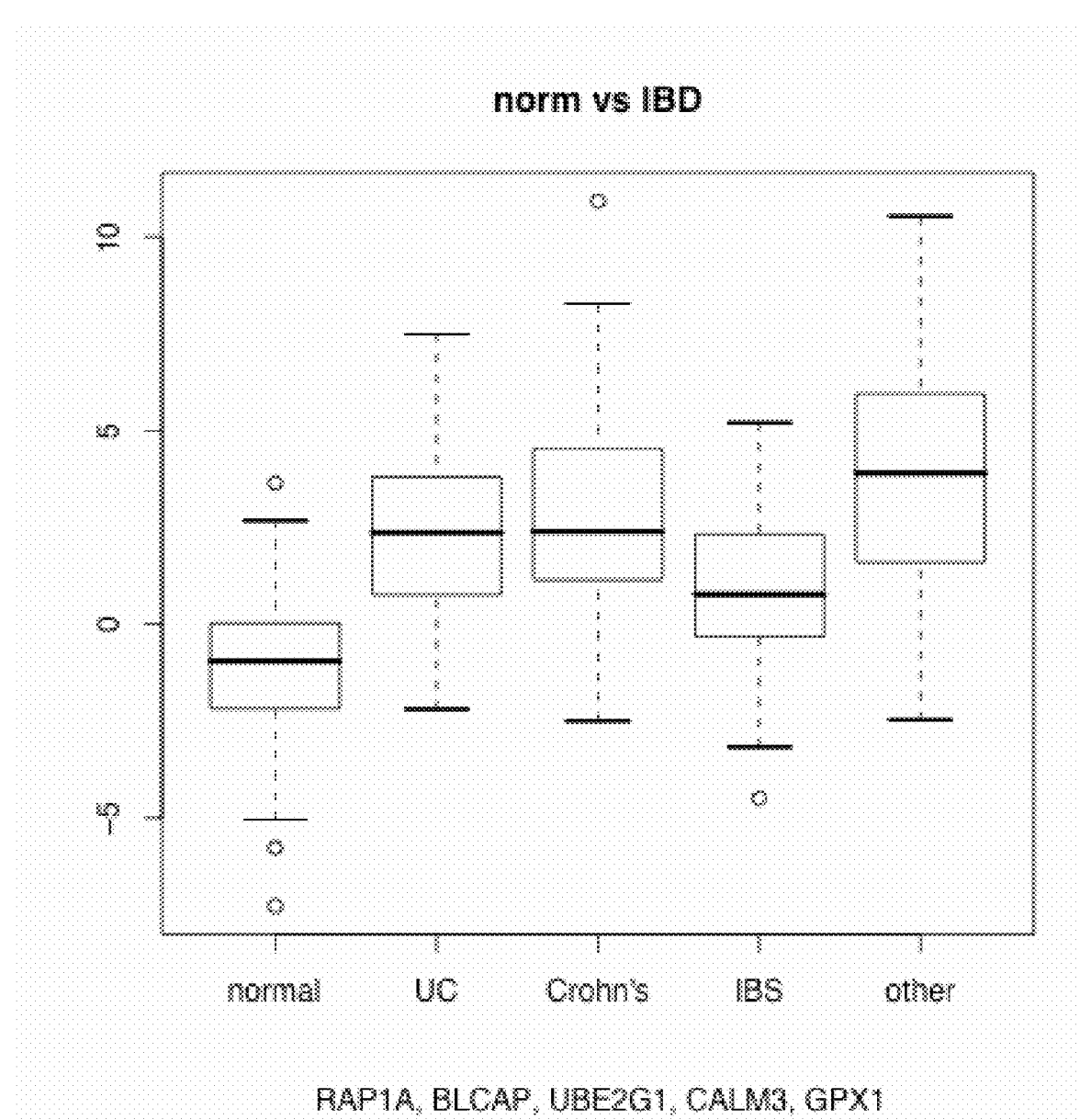
FIG. 2 shows the boxplots of the logistic regression scores based on expression levels of 5 of the 8 genes for the five patient cohorts. Note the separation of the normal and IBD patients (UC and Crohn's).

An example of biomarker performance is shown in FIG. 2, the boxplots of the logistic regression scores based on expression levels of 5 of the 8 genes whose combination differentiates between normal and IBD patients (RAP1A, BLCAP, UBE2G1, CALM3, and GPX1). The classification matrix and diagnostic accuracy estimates of the combination for IBD v Normal are shown below the graph (Tables 5a-b).

TABLE 5a

IBD vs Normal (5-gene) Classification Matrix

|  | IBD | Normal |
|---|---|---|
| test > 0 | 162 | 25 |
| test ≦ 0 | 22 | 71 |

Fisher exact OR = 20.57, $p < 2 \times 10^{-16}$

TABLE 5b

Performance Measures

|  | study prevalence |
|---|---|
| Accuracy | 83.2% |
| Sensitivity | 88.0% |
| Specificity | 74.0% |
| Positive Predictive Value (PPV) | 86.6% |
| Negative Predictive Value (NPV) | 76.3% |

2B. IBD vs. Normal 4-Gene Combination

An initial logistic regression model was built using data for all eight genes. The model was trimmed by eliminating genes not statistically significantly contributing to the model. The result of this analysis is a four-gene model incorporating: RAP1A, BLCAP, UBE2G1, and GPX1. The accuracy of this model in distinguishing IBD samples from normal samples is 80.4%, as shown in Table 6b, below, along with the other performance measures of this 4-gene combination.

TABLE 6a

IBD vs Normal (4-gene) Classification Matrix

|  | IBD | Normal |
|---|---|---|
| test > 0 | 159 | 30 |
| test ≦ 0 | 25 | 66 |

Fisher exact OR = 13.81, $p < 2 \times 10^{-16}$

TABLE 6b

Performance Measures

|  | study prevalence |
|---|---|
| Acc | 80.4% |
| Sens | 86.4% |
| Spec | 68.8% |
| PPV | 84.1% |
| NPV | 72.5% |

2C. Normal & IBS vs. IBD 7 Gene Combination

Figure 3:
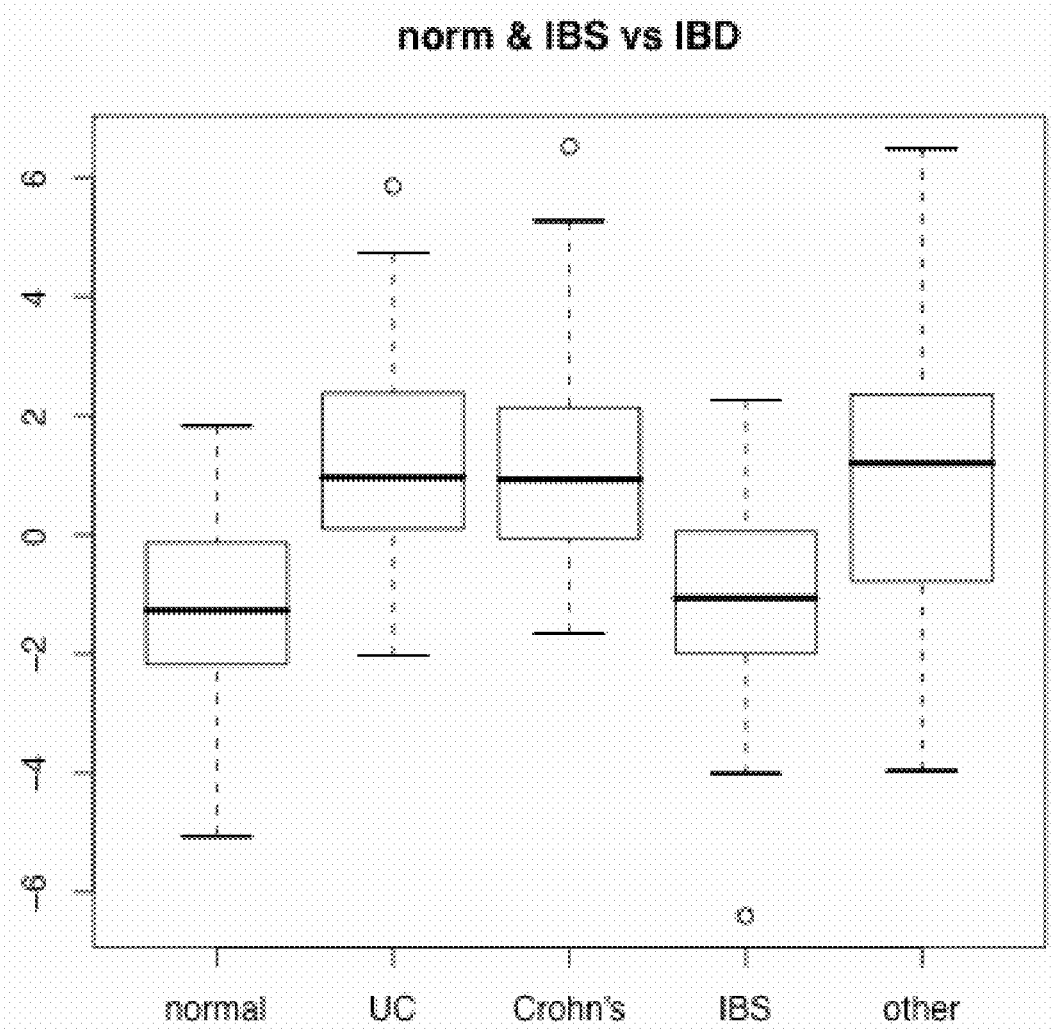
FIG. 3 shows the boxplots of the logistic regression scores based on expression levels of 7 of the 8 genes for the five patient cohorts. Note the separation of the normal and IBS from the IBD patients (UC and Crohn's).

An example of biomarker performance is shown in FIG. 3, boxplots of the logistic regression scores based on expression levels of 7 of the 8 genes whose combination differentiates between normal/IBS and IBD patients (RAP1A, BLCAP, UBE2G1, CALM3, GPX1, HIST1H2BK, AND PPP2R5A). The classification matrix and diagnostic accuracy estimates (Tables 7a-b) of the combination for IBD v Normal/IBS are shown below the graph.

TABLE 7a

IBS&Normal vs IBD (7-gene) Classification Matrix

|  | IBD | IBS + Normal |
|---|---|---|
| test > 0 | 141 | 44 |
| test ≦ 0 | 43 | 150 |

Fisher exact OR = 11.09, $p < 2 \times 10^{-16}$

TABLE 7b

Performance measures

|  | study prevalence |
|---|---|
| Acc | 77.0% |
| Sens | 76.6% |
| Spec | 77.3% |
| PPV | 76.2% |
| NPV | 77.7% |

2D. IBS vs. Normal 4-Gene Combination

An initial logistic regression model was built using data for all eight genes. The model was trimmed by eliminating genes not statistically significantly contributing to the model. The result of this analysis is a four-gene model incorporating: BLCAP, TH1L, CALM3, and HIST1H2BK. The accuracy of this model in distinguishing IBS samples from normal samples is 84.7%.

Figure 4:
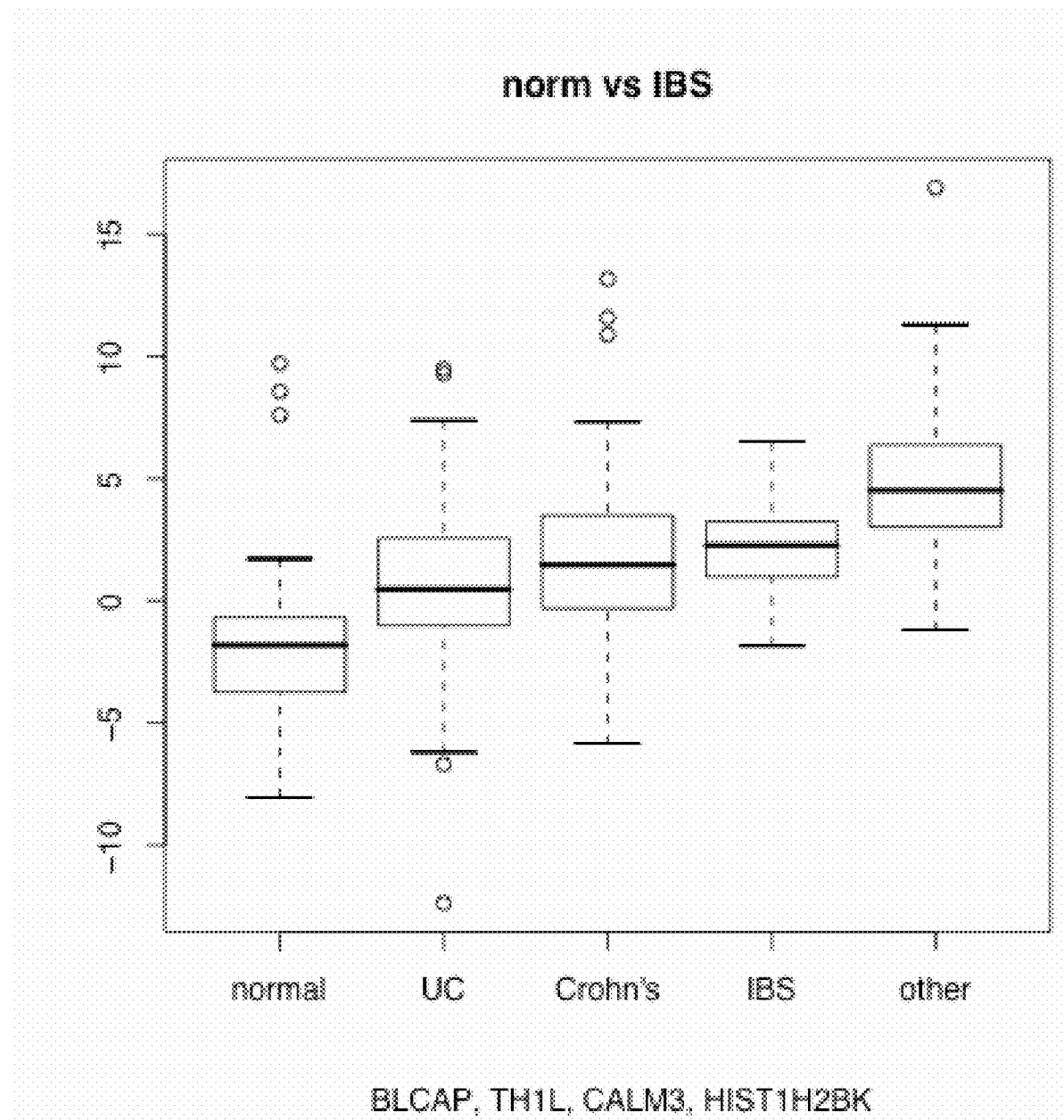
FIG. 4 shows the boxplots of the logistic regression scores based on expression levels of 4 of the 8 genes for the five patient cohorts. Note the separation of the Normal and IBS patients.

The biomarker performance is in FIG. 4, boxplots of the logistic regression scores based on expression levels of 4 of the 8 genes whose combination differentiates between Normal and IBS patients. The classification matrix and diagnostic accuracy estimates of the combination for Normal versus IBS are shown in Tables 8a-b, below the graph.

TABLE 8a

IBS vs Normal (4-gene) Classification Matrix

|  | IBS | Normal |
|---|---|---|
| test > 0 | 83 | 16 |
| test ≤ 0 | 15 | 82 |

Fisher exact OR = 27.62, p < 2 × 10$^{-16}$

TABLE 8b

Performance measures

| | study prevalence |
|---|---|
| Acc | 84.2% |
| Sens | 84.7% |
| Spec | 83.7% |
| PPV | 83.8% |
| NPV | 84.5% |

2E. IBD vs. IBS 6-Gene Combination

As above, an initial logistic regression model was built using data for all eight genes. The model was trimmed by eliminating genes not statistically significantly contributing to the model. The result of this analysis is a six-gene model incorporating: RAP1A, UBE2G1, CALM3, GPX1, HISTH2BK, and PPP2R5A. The accuracy of this model in distinguishing IBS samples from IBD samples is 83.0%.

TABLE 9a

IBD vs IBS differentiation

|  | IBD | IBS |
|---|---|---|
| test > 0 | 163 | 27 |
| test ≤ 0 | 21 | 71 |

Fisher exact OR = 20.09, p < 2 × 10$^{-16}$

TABLE 9b

Performance measures

| | study prevalence |
|---|---|
| Acc | 83.0% |
| Sens | 88.6% |
| Spec | 72.4% |
| PPV | 85.8% |
| NPV | 77.2% |

Summary: The ability of the expression levels of these genes, as measured by RT-PCR and normalized by Actin B expression, to individually distinguish between IBD and normal controls; IBD from IBS; IBD from Normal & IBS; and IBS from Normal are shown in Table 10, (below). The p values for significant differences in expression levels for each gene, between each pair of cohorts are shown. To the right of each p-value, the experimental values (the ΔCt) are shown as "+" (or "−") to indicate a higher (or lower) ΔCt for one member of the subject pair relative to the other (see legend to Table 10). The ΔCt is inversely proportional to the expression level.

TABLE 10

Significantly different expression levels of individual genes p values (Wilcoxon rank sum test)

| Probe | IBD vs normal | | IBD vs IBS | | IBD vs norm&IBS | | IBS vs normal | |
|---|---|---|---|---|---|---|---|---|
| RAP1A | 4.22 × 10$^{-16}$ | + | 5.24 × 10$^{-5}$ | + | 1.62 × 10$^{-13}$ | + | 6.25 × 10$^{-7}$ | + |
| BLCAP | 3.62 × 10$^{-15}$ | + | 0.78 | na | 3.59 × 10$^{-6}$ | + | 9.45 × 10$^{-16}$ | + |
| TH1L | 6.78 × 10$^{-7}$ | + | 0.69 | na | 1.0 × 10$^{-3}$ | + | 7.86 × 10$^{-6}$ | + |
| UBE2G1 | 8.34 × 10$^{-12}$ | + | 0.003 | − | 0.018 | + | <2.2 × 10$^{-16}$ | + |
| CALM3 | 3.57 × 10$^{-10}$ | + | 0.24 | na | 5.53 × 10$^{-6}$ | + | 9.79 × 10$^{-7}$ | + |
| GPX1 | 0.099 | na | 0.007 | − | 7.59 × 10$^{-3}$ | − | 0.34 | na |
| HIST1H2BK | 0.069 | na | 1.02 × 10$^{-6}$ | − | 0.061 | na | 3.85 × 10$^{-9}$ | + |
| PPP2R5A | 5.13 × 10$^{-6}$ | + | 7.73 × 10$^{-3}$ | − | 0.25 | na | 7.25 × 10$^{-12}$ | + |

Legend:

IBD vs normal: + = higher ΔCt in IBD relative to normal; − = lower ΔCt in IBD relative to normal IBD vs IBS: + = higher ΔCt in IBD relative to IBS; − = lower ΔCt in IBD IBD vs normal&IBS: + = higher ΔCt in IBD relative to normal&IBS; − = lower ΔCt in IBD IBS vs normal: + = higher ΔCt in IBS relative to normal; − = lower ΔCt in IBS All: na = not applicable because p-value is not significant In all cases, the ΔCt is inversely proportional to expression level. Therefore a lower ΔCt represents a higher level of gene expression and a higher ΔCt represents a lower level of gene expression.

While all eight genes were found to be statistically significantly associated with IBD or IBS, the individual genes are not highly accurate in discriminating the various subgroups. We investigated if combinations of genes selected from the eight might enable clinically useful marker accuracies.

For each of the data subsets: IBD vs. normal control, IBS vs. normal control, IBS and Normal vs. IBD, and IBD vs. IBS, we evaluated the accuracy of gene combinations using logistic regression. One skilled in the art will understand that given a set of measurements, such as the gene expression values for a particular set of genes, and given these measurements across a particular set of samples, such as a group of IBD samples and a group of 'normal' samples, there are many techniques for deriving from that data a 'set of rules' for classifying a sample as, e.g., IBD or normal. Those skilled in the art will understand that an algorithm, including a weighting for each gene expression level, will follow from the logistic regression analysis, according to one method of the body of knowledge known as 'supervised learning', which is a sub-field of 'machine learning', which itself can be considered sub-field of 'data mining'. Supervised learning encompasses techniques for deriving algorithms, or rules, from data. One skilled in the art will understand that there are no clear boundaries between a standard statistical approach, and a 'supervised learning' approach, and that the classification formulas presented below could be considered as being derived from a supervised learning approach, but could also be termed a standard statistical approach.

The boxplots in the examples above are a visual display of the distribution of the individual scores within each cohort for the weightings that were optimized for a given comparison. The threshold for the classification score is zero in all cases. For IBD v Normal, IBD is greater than zero and Normal is less than zero; the IBS and Other categories are included as informational, but they were not used in determining the gene expression weightings. Similarly for IBD v Normal & IBS, IBD is greater than zero and Normal & IBS are less than zero, and the Other category was not used in deriving the weightings. And the same for IBS v Normal: IBS is greater than zero and Normal is less than zero, and the IBD and Other categories weren't used to derive expression weightings. Thus, the specific ups and downs of the expression levels of individual genes in the marker set do matter in the classifier, but not in a direct always-up or always-down manner. What matters is whether the sum of the weighted expression values is greater than or less than zero. A specific gene may have increased expression in one correctly classified patient, and that same gene may have a decreased expression in another correctly classified patient if the score is "compensated" by appropriately weighted changes in the expression of other genes in the marker set.

By way of non-limiting example, in one specific measurement, the following gene weightings were applied:

| IBS vs Normal |
| --- |
| 4 gene BLCAP, TH1L, CALM3, HIST1H2BK<br>If(−16.6856 + 11.2898(BLCAP) − 4.9722(TH1L) − 3.7663(CALM3) + 2.5060(HIST1H2BK)) > 0<br>Then IBS<br>Else Normal |

For IBS versus Normal and given the gene weightings above and a threshold of zero with IBS greater than zero and Normal less than or equal to zero, a hypothetical patient with expression levels of BLCAP=2.0, TH1L=1.0, CALM3=1.0, and HIST1H2BK=2.0 would have a weighted score of (−16.6856+11.2898(2.0)−4.9722(1.0)−3.7663(1.0)+2.5060 (2.0)=2.1675, resulting in a classification of IBS.

Other non-limiting examples of such weightings are as follows:

| IBS & Normal vs IBD |
| --- |
| 7-gene RAP1A, BLCAP, UBE2G1, CALM3, GPX1, HIST1H2BK, PPP2R5A:<br>If (−.1602 + 4.487(RAP1A) + 2.5746(BLCAP) − 2.8938(UBE2G1) + 3.8415(CALM3) − 2.3682(GPX1) − 1.5623(HIST1H2BK) − 1.4927(PPP2RR5A)) > 0<br>Then IBD<br>Else IBS or Normal |

| IBD vs Normal |
| --- |
| 4-gene RAP1A, BLCAP, UBE2G1, GPX1<br>If(−10.8729 + 3.3467(RAP1A) + 5.1866(BLCAP) − 3.4559(UBE2G1) + 3.237(CALM3) − 3.225(GPX1)) > 0<br>Then IBD<br>Else Normal |

| IBD vs Normal |
| --- |
| 5-gene RAP1A, BLCAP, UBE2G1, CALM3, GPX1:<br>Formula: (−10.7716 + $\Delta Ct_{RAP1A}$ * 3.2485 + $\Delta Ct_{BLCAP}$ * 5.4360 − $\Delta Ct_{UBE2G1}$ * 3.4723 + $\Delta Ct_{CALM3}$ * 3.3511 − $\Delta Ct_{GPX1}$ * 3.4642)<br>If(−10.7716 + $\Delta Ct_{RAP1A}$ * 3.2485 + $\Delta Ct_{BLCAP}$ * 5.4360 − $\Delta Ct_{UBE2G1}$ * 3.4723 + $\Delta Ct_{CALM3}$ * 3.3511 − $\Delta Ct_{GPX1}$ * 3.4642) > 0<br>Then IBD<br>Else Normal |

| IBS vs IBD |
| --- |
| 6-gene RAP1A, UBE2G1, CALM3, GPX1, HIST1H2BK, PPP2R5A:<br>Formula: (16.6895 + $\Delta Ct_{RAP1A}$ * 5.1550 − $\Delta Ct_{UBE2G1}$ * 2.5462 + $\Delta Ct_{CALM3}$ * 4.8674 − $\Delta Ct_{GPX1}$ * 2.3979 − $\Delta Ct_{HIST1H2BK}$ * 2.8183 − $\Delta Ct_{PPP2R5A}$ * 2.9778)<br>If 16.6895 + $\Delta Ct_{RAP1A}$ * 5.1550 − $\Delta Ct_{UBE2G1}$ * 2.5462 + $\Delta Ct_{CALM3}$ * 4.8674 − $\Delta Ct_{GPX1}$ * 2.3979 − $\Delta Ct_{HIST1H2BK}$ * 2.8183 − $\Delta Ct_{PPP2R5A}$ * 2.9778 > 0.0<br>Then IBD<br>ELSE NORMAL |

One exemplary classification rule derived from logistic regression analysis of the Burczynski et al (2006) data for classifying IBD vs. Normal using the 5-gene IBD vs Normal biomarker would be:

```
IF
−1.1704 − .2815 * RAP1A + 0.7027 * BLCAP + 0.3143 * UBE2G1 +
0.1089 * CALM3 − 0.4782 * GPX1 is less than 0
THEN IBD
ELSE NORMAL
```

|  | actual | |
| --- | --- | --- |
| predicted | IBD | Normal |
| IBD | 82 | 1 |
| Normal | 3 | 41 |
| Accuracy | 96.9% | |
| Sensitivity | 96.5% | |
| Specificity | 97.6% | |
| PPV | 98.8% | |
| NPV | 93.2% | |

Figure 5:
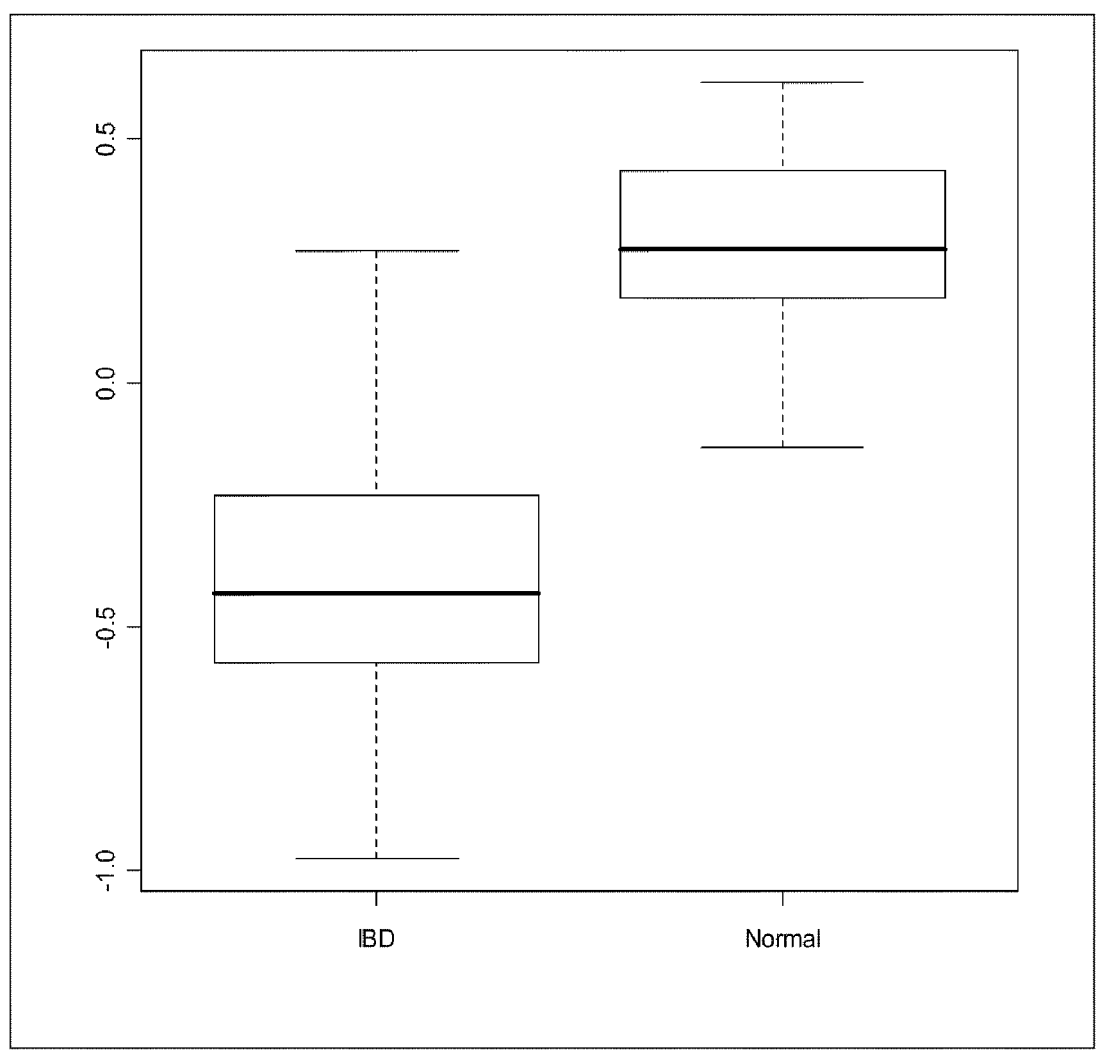
FIG. 5 is a boxplot of the logistic regression scores based on expression levels of 5 genes whose combination differentiates IBD vs. Normal.

FIG. 5 shows the box plots of the regression scores based on expression levels of 5 genes whose combination differentiates IBD from normal (RAP1A, BLCAP, UBE2G1, CALM3, and GPX1).

The weightings disclosed above are optimal examples; as will be clear to those of skill in the art, the weightings can vary widely based on, for example, the use of a different classifier to generate the weightings, or the use of modified weightings that may provide lower accuracy but improved specificity (or some other change to the assay of interest to a user).

EXAMPLE 3

In a separate study, ten of the genes listed in Table 4 that occurred most frequently in the top sets shown in Table 3 were evaluated, along with Actin B as a control gene, in a subsequent study on a total of 482 RBC-depleted whole blood samples from: 98 normal controls, 91 Ulcerative Colitis patients, 98 Crohn's Disease patients, 98 IBS patients and 97 patients with non-gastrointestinal inflammatory disease. Samples were obtained from 7 clinical sites at various geographic locations within the U.S.A.; in the analysis there was no distinction made between Crohn's and UC.

The RNA expression levels of ten genes from among the 15 features in the top discovery marker sets were measured by quantitative real-time PCR in the RBC-depleted whole blood of a prospectively ascertained sample of affected patients and unaffected controls. An additional eleventh gene was measured to serve as an internal reference standard across patients. Five cohorts of patients had RNA assayed:

98 Normal
98 Crohn's Disease
91 Ulcerative Colitis
98 Irritable Bowel Syndrome
97 Non-Gastrointestinal Inflammatory Disease The 11 genes (including 1 control) assayed for RNA expression levels in the 5 cohorts of patients were: (Human Genome Organization (HUGO) Gene Nomenclature Committee names are given)

RAP1A
BLCAP
PPP2R5A
UBE2G1
GPX1
TH1-L
CALM3
HIST1H2BK
NONO
HMGB1
ACTB (the internal reference gene)

Whole blood samples and clinical information were obtained from all patients. Each IBD patient was diagnosed by a board-certified gastroenterologist; IBD diagnoses were confirmed by endoscopy. Each IBS patient was diagnosed by a board-certified gastroenterologist using Rome I criteria. All protocols were IRB approved; informed consent was obtained and peripheral blood samples and clinical data were collected from all patients. Expression data were obtained from peripheral whole blood samples (with no mononuclear enrichment) by isolating total mRNAs, synthesizing cDNAs, and performing real-time quantitative PCR on an Applied Biosystems 7300 Real-Time PCR System. Expression levels were output as Ct (cycle or crossing threshold). DeltaCts of each gene for each patient were computed to normalize gene expression levels of the 10 marker genes to the intra-subject reference gene (ACTB also referred to as β-Actin). DeltaCt=Ct[marker gene]–Ct[ACTB]. The DeltaCts were then used for analysis of diagnostic classification performance.

3A IBD vs Normal (6-Gene)

An optimal scoring algorithm for classification of patients as IBD or normal was derived based on 6 of the 10 tested genes (RAP1A, BLCAP, UBE2G1, CALM3, GPX1, NONO). The classification matrix and diagnostic performance measures for this biomarker are given in Table 11a and 11b, respectively.

TABLE 11a

IBD vs Normal (6-gene) Classification Matrix

|  |  | Clinical Diagnosis | |
|---|---|---|---|
|  |  | IBD | Normal |
| Biomarker Classification | IBD | 168 | 25 |
|  | Normal | 21 | 73 |

Fisher's exact Odds Ratio (2-sided) = 23.0, p < 2 × 10−16

TABLE 11b

Diagnostic Performance Measures

| accuracy* | 84% |
|---|---|
| sensitivity | 89% |
| specificity | 75% |
| positive predictive value* | 87% |
| negative predictive value* | 78% |
| AUC-ROC | 0.91 |

*result based on study prevalences.

The NPV for an adjusted 25% prior probability of IBD (a rule-out scenario) is 95%. The PPV for an adjusted 75% prior probability of IBD (a rule-in scenario) is 91%.

3B. IBS vs Normal (4-Gene)

An optimal scoring algorithm for classification of patients as IBS or normal was derived based on 4 of the 10 tested genes (BLCAP, UBE2G1, TH1L, HIST1H2BK). The classification of patients by clinical diagnosis and test result is given in Table 12a. The diagnostic performance of the classification is summarized in Table 12b.

TABLE 12a

IBS vs Normal (4-gene) Classification Matrix

|  |  | Clinical Diagnosis | |
|---|---|---|---|
|  |  | IBS | Normal |
| Biomarker Classification | IBS | 87 | 21 |
|  | Normal | 11 | 77 |

Fisher's exact Odds Ratio (2-sided) = 28.3, p < 2 × 10−16

TABLE 12b

Diagnostic Performance Measures

| accuracy* | 84% |
|---|---|
| sensitivity | 89% |
| specificity | 79% |
| positive predictive value* | 81% |
| negative predictive value* | 88% |
| AUC-ROC | 0.92 |

*result based on study prevalences

The NPV for an adjusted 25% prior probability of IBS (a rule-out scenario) is 96%. The PPV for an adjusted 75% prior probability of IBS (a rule-in scenario) is 93%.

3C. IBS vs IBD (7 Gene)

An optimal scoring algorithm for classification of patients as IBS or IBD was derived based on 7 of the 10 tested genes (RAP1A, UBE2G1, CALM3, GPX1, HIST1H2BK, PPP2R5A, BLCAP). The classification of patients by clinical diagnosis and test result is given in Table 13a. The diagnostic performance of the classification is summarized in Table 13b.

TABLE 13a

IBS vs IBD (7-gene) Classification Matrix

|  | IBD | IBS |
|---|---|---|
| test > 0 | 163 | 26 |
| test ≤ 0 | 21 | 72 |

Fisher's exact OR = 21.14, $p < 2 \times 10^{-16}$

TABLE 13b

Clinical Performance Measures

|  | study prevalence |
|---|---|
| Acc | 83.3% |
| Sens | 88.6% |
| Spec | 73.5% |
| PPV | 86.2% |
| NPV | 77.4% |

The PPV for an adjusted 75% prior probability of IBD (a rule-in IBD scenario) is 90.9%. The NPV for an adjusted 25% prior probability of IBD (a rule-out IBD scenario) is 95.1%.

3D (IBX vs Normal)

An optimal scoring algorithm for classification of patients as either IBS or IBD vs normal was derived based on 6 of the 10 tested genes (6-gene BLCAP, CALM3, GPX1, TH1L, RAP1A, NONO IBX vs Normal). The classification of patients by clinical diagnosis and test result is given in Table 14a. The diagnostic performance of the classification is summarized in Table 14b.

TABLE 14a

IBX vs Normal (6-gene) Classification Matrix

|  | IBX | norm |
|---|---|---|
| test > 0 | 269 | 45 |
| test ≤ 0 | 18 | 53 |

Fisher's exact OR = 17.4, $p < 2 \times 10^{-16}$

TABLE 14b

Clinical Performance Measures

|  | at study prevalence |
|---|---|
| Acc | 83.6% |
| Sens | 93.7% |

TABLE 14b-continued

Clinical Performance Measures

|  | at study prevalence |
|---|---|
| Spec | 54.1% |
| PPV | 85.7% |
| NPV | 74.6% |

3E Shared Biology of Genes in Biomarkers

Expression levels of the 10 candidate biomarker genes in Example 3 were assayed on each patient specimen and normalized to a within-patient reference gene. Optimal scoring algorithms for classification of patients as IBD versus normal and IBS versus normal were derived separately using the expression levels of the 10 genes assayed in these pilot study patients. The optimal gene set for each test and each set's performance is indicated in Table 15. The classification results had odds ratios of 23.0 and 28.3, respectively, with both p-values$<2 \times 10^{-16}$. Two genes were common to both diagnostic marker sets. The genes identified as diagnostic for the comparisons reveal an overlap between IBD and IBS patients. This overlap of highly statistically significant biomarkers suggests a shared biology between the two disease states. The commonality of the two genes could indicate that genes have a causative role or that they are part of a common response mechanism.

TABLE 15

Highly significant expression biomarker sets in IBD and IBS*

| Cohort sub set odds ratio and p-value genes in marker sets | IBD vs Normal OR = 23.0, $p = 2 \times 10^{-16}$ (Fisher's 2-sided exact) Expression level* | IBS vs Normal OR = 28.3, $p = 2 \times 10^{-16}$ (Fisher's 2-sided exact) Expression level* |
|---|---|---|
| BLCAP | + | + |
| UBE2G1 | + | + |
| TH1L |  | + |
| CALM3 | + |  |
| HIST1H2BK |  | + |
| GPX1 | n.a. |  |
| NONO | + |  |
| RAP1A | + |  |

*univariate ΔCt (inversely proportional to expression level) difference relative to Normal: "+" increased; "−" decreased; "+/−" no difference; n.a. = not significantly different Summary: The ability of the expression levels of these 10 genes, as measured by RT-PCR and normalized by Actin B expression, to individually distinguish between IBD and normal controls; IBD from IBS; IBS from Normal; and IBS&IBD from normal are shown in Table 16 (below). The p values for significant differences in expression levels for each gene, between each pair of subjects are shown. To the right of each p-value, the experimental values (the ΔCt) are shown as "+" (or "−") to indicate a higher (or lower) ΔCt for one member of the subject pair relative to the other (see legend to Table 16). The ΔCt is inversely proportional to the expression level.

TABLE 16

Significantly different expression levels of individual genes

| Probe | IBD vs normal |  | IBD vs IBS |  | IBS vs normal |  | IBS&IBD vs normal |  |
|---|---|---|---|---|---|---|---|---|
| RAP1A | $4.22 \times 10^{-16}$ | + | $5.24 \times 10^{-5}$ | + | $6.25 \times 10^{-7}$ | + | $8.24 \times 10^{-15}$ | + |
| BLCAP | $3.62 \times 10^{-15}$ | + | 0.78 | na | $9.45 \times 10^{-16}$ | + | $<2.2 \times 10^{-16}$ | + |
| TH1L | $6.78 \times 10^{-7}$ | + | 0.69 | na | $7.86 \times 10^{-6}$ | + | $8.89 \times 10^{-8}$ | + |

TABLE 16-continued

Significantly different expression levels of individual genes

| Probe | IBD vs normal | | IBD vs IBS | | IBS vs normal | | IBS&IBD vs normal | |
|---|---|---|---|---|---|---|---|---|
| UBE2G1 | $8.34 \times 10^{-12}$ | + | 0.003 | − | $<2.2 \times 10^{-16}$ | + | $<2.2 \times 10^{-16}$ | + |
| CALM3 | $3.57 \times 10^{-10}$ | + | 0.24 | na | $9.79 \times 10^{-7}$ | + | $1.19 \times 10^{-10}$ | + |
| GPX1 | 0.099 | na | 0.007 | − | 0.34 | na | 0.45 | na |
| HIST1H2BK | 0.069 | na | $1.02 \times 10^{-6}$ | − | $3.85 \times 10^{-9}$ | + | $1.89 \times 10^{-4}$ | + |
| PPP2R5A | $5.13 \times 10^{-6}$ | + | $7.73 \times 10^{-3}$ | − | $7.25 \times 10^{-12}$ | + | $1.38 \times 10^{-9}$ | + |
| NONO | $6.70 \times 10^{-5}$ | + | 0.053 | na | 0.08 | na | $4.50 \times 10^{-4}$ | + |
| HMGB1 | $4.61 \times 10^{-10}$ | + | 0.47 | na | 0.16 | na | $4.24 \times 10^{-10}$ | + |

Legend:
IBD vs normal: + = higher ΔCt in IBD relative to normal; − = lower ΔCt in IBD relative to normal
IBD vs IBS: + = higher ΔCt in IBD relative to IBS; − = lower ΔCt in IBD
IBS vs normal: + = higher ΔCt in IBS relative to normal; − = lower ΔCt in IBS
IBS&IBD vs normal: + = higher ΔCt in IBS&IBD relative to normal; − = lower ΔCt in IBS&IBD
All: na = not applicable because p-value is not significant
In all cases, the ΔCt is inversely proportional to expression level. Therefore a lower ΔCt represents a higher level of gene expression and a higher ΔCt represents a lower level of gene expression.

While all ten genes were found to be statistically significantly associated with IBD or IBS, the individual genes are not highly accurate in discriminating the various subgroups. We investigated whether combinations of genes selected from the ten might enable clinically useful marker accuracies. For each of the data subsets: IBD vs. normal control, IBS vs. normal control, IBS vs. IBD, and IBD& IBS vs. normal, we evaluated the accuracy of gene combinations using logistic regression. One skilled in the art will understand that given a set of measurements, such as the gene expression values for a particular set of genes, and given these measurements across a particular set of samples, such as a group of IBD samples and a group of 'normal' samples, there are many techniques for deriving from that data a 'set of rules' for classifying a sample as eg IBD or normal. Those skilled in the art will understand that an algorithm, including a weighting for each gene expression level, will follow from the logistic regression analysis, according to one method of the body of knowledge known as 'supervised learning', which is a sub-field of 'machine learning', which itself can be considered a sub-field of 'data mining'. Supervised learning encompasses techniques for deriving algorithms, or rules, from data. One skilled in the art will understand that there are no clear boundaries between a standard statistical approach, and a 'supervised learning' approach, and that the classification formulas presented below could be considered as being derived from a supervised learning approach, but could also be termed a standard statistical approach.

The threshold for the classification score is zero in all cases. For IBD v Normal, IBD is greater than zero and Normal is less than zero; the IBS and Other were not used in determining the gene expression weightings. Similarly for IBS vs. Normal, IBS is greater than zero and Normal is less than zero, and the Other categories were not used in deriving the weightings. In the case of IBD vs. IBS, IBD is greater than zero and IBS is less than zero and the Normal and Other categories were not used to derive expression weightings. Finally, in the case of IBD and IBS vs. normal, a score greater than zero indicates either IBD or IBS; a score less than zero indicates Normal, and the Other category was not used to derive the weightings. Thus, the specific ups and downs of the expression levels of individual genes in the marker set do matter in the classifier, but not in a direct always-up or always-down manner with respect to the disease or non-disease status patient. Of more importance is whether the sum of the weighted expression values is greater than or less than zero. A specific gene may have increased expression in one correctly classified patient, and that same gene may have a decreased expression in another correctly classified patient if the score is "compensated" by appropriately weighted changes in the expression of other genes in the marker set.

The following exemplary gene weightings were applied:

---

IBD vs Normal 6-gene RAP1A, BLCAP, UBE2G1, CALM3, GPX1, NONO:
IBD Diagnostic Index: = (−16.5312 + 4.7721[dCt$_{BLCAP}$] − 3.3249[dCt$_{GPX1}$]$_+$ 3.6521[dCt$_{RAP1A}$] − 3.0221[dCt$_{UBE2G1}$] + 3.0669[dCt$_{CALM3}$] + 0.8405[dCt$_{NONO}$])
If (−16.5312 + 4.7721[dCt$_{BLCAP}$] − 3.3249[dCt$_{GPX1}$]$_+$ 3.6521[dCt$_{RAP1A}$] − 3.0221[dCt$_{UBE2G1}$] + 3.0669[dCt$_{CALM3}$] + 0.8405[dCt$_{NONO}$]) > 0
Then   IBD
Else   Normal IBS vs Normal 4-gene BLCAP, TH1L, UBE2G1, HIST1H2BK:
Formula: = −22.1323 + 5.4337 [dCt$_{BLCAP}$] + 3.3187[dCt$_{UBE2G1}$] − 4.1747 [dCt$_{TH1L}$] + 1.6902[dCt$_{HIST1H2BK}$]
If [−22.1323 + 5.4337 [dCt$_{BLCAP}$] + 3.3187[dCt$_{UBE2G1}$] − 4.1747 [dCt$_{TH1L}$] + 1.6902[dCt$_{HIST1H2BK}$] > 0
Then   IBS
Else   Normal IBD vs IBS 7-gene RAP1A, UBE2G1, CALM3, GPX1, HIST1H2BK, PPP2R5A, BLCAP:
Formula: (17.6564 + ΔCt$_{RAP1A}$ * 5.7988 − ΔCt$_{UBE2G1}$ * 5.6479 + ΔCt$_{CALM3}$ * 3.4257 − ΔCt$_{GPX1}$ * 2.5535 − ΔCt$_{HIST1H2BK}$ * 2.1366 − ΔCt$_{PPP2R5A}$ * 2.4503 + ΔCT$_{BLCAP}$ * 3.0325)
IF (17.6564 + ΔCt$_{RAP1A}$ * 5.7988 − ΔCt$_{UBE2G1}$ * 5.6479 + ΔCt$_{CALM3}$ * 3.4257 − ΔCt$_{GPX1}$ * 2.5535 − ΔCt$_{HIST1H2BK}$ * 2.1366 − ΔCt$_{PPP2R5A}$ * 2.4503 + ΔCt$_{BLCAP}$ * 3.0325) > 0
Then   IBD
Else   IBS IBX vs Normal 6-gene BLCAP, CALM3, GPX1, TH1L, RAP1A, NONO:
Formula: (−13.5528 + ΔCt$_{BLCAP}$ * 4.9346 + ΔCt$_{CALM3}$ * 2.8244 − ΔCt$_{GPX1}$ * 1.8043 − ΔCt$_{TH1L}$ * 2.8452 + ΔCt$_{RAP1A}$ * 1.2203 + ΔCt$_{NONO}$ * 1.04)
IF (−13.5528 + ΔCt$_{BLCAP}$ * 4.9346 + ΔCt$_{CALM3}$ * 2.8244 − ΔCt$_{GPX1}$ * 1.8043 − ΔCt$_{TH1L}$ * 2.8452 + ΔCt$_{RAP1A}$ * 1.2203 + ΔCt$_{NONO}$ * 1.04) > 0
Then   IBD or IBS
Else   Normal We subsequently analyzed the biomarker performance based on expression levels of combinations of 3 of the 5 genes tested above (Examples 2D and 3B), whose combination differentiates between normal and IBS patients (BLCAP, TH1L, CALM3, HIST1H2BK, and UBE2G1). The classification matrix and diagnostic accuracy estimates of the combination for IBS v Normal, as well as exemplary gene weightings, are shown in Table 17.

TABLE 17

| combination | | 2 × 2 table | | | accuracy | sensitivity | specificity | PPV | NPV |
|---|---|---|---|---|---|---|---|---|---|
| | | IBS | Normal | fisher's | | | | | |
| BLCAP | test > 0 | 81 | 19 | OR = 19.39 | 81.6% | 82.7% | 80.6% | 81.0% | 82.3% |
| TH1L | test ? 0 | 17 | 79 | $p < 2 \times 10^{-16}$ | | | | | |
| CALM3 | | | | | | | | | |
| equation: $-10.0504 + 8.4473 * \Delta Ct_{BLCAP} - 5.4222 * \Delta Ct_{TH1L} + 2.4570 * \Delta Ct_{CALM3}$ | | | | | | | | | |
| BLCAP | test > 0 | 88 | 20 | OR = 33.38 | 84.7% | 89.8% | 79.6% | 81.5% | 88.6% |
| TH1L | test ? 0 | 10 | 78 | $p < 2 \times 10^{-16}$ | | | | | |
| UBE2G1 | | | | | | | | | |
| equation: $-16.4275 + 5.0435 * \Delta Ct_{BLCAP} - 4.4467 * \Delta Ct_{TH1L} + 4.1683 * \Delta Ct_{UBE2G1}$ | | | | | | | | | |
| BLCAP | test > 0 | 82 | 16 | OR = 27.62 | 84.2% | 84.5% | 83.8% | 83.7% | 84.7% |
| TH1L | test ? 0 | 15 | 83 | $p < 2 \times 10^{-16}$ | | | | | |
| HIST1H2BK | | | | | | | | | |
| equation: $-17.5471 + 8.2126 * \Delta Ct_{BLCAP} - 4.2986 * \Delta Ct_{TH1L} + 2.1835 * \Delta Ct_{HIST1H2BK}$ | | | | | | | | | |
| BLCAP | test > 0 | 83 | 23 | OR = 17.68 | 80.6% | 84.7% | 76.5% | 78.3% | 83.3% |
| CALM3 | test ? 0 | 15 | 75 | $p < 2 \times 10^{-16}$ | | | | | |
| UBE2G1 | | | | | | | | | |
| equation: $-21.741 + 0.6081 * \Delta Ct_{BLCAP} - 0.5865 * \Delta Ct_{CALM3} + 3.933 * \Delta Ct_{UBE2G1}$ | | | | | | | | | |
| BLCAP | test > 0 | 83 | 25 | OR = 15.86 | 79.6% | 84.7% | 74.5% | 76.9% | 83.0% |
| CALM3 | test ? 0 | 15 | 73 | $p < 2 \times 10^{-16}$ | | | | | |
| HIST1H2BK | | | | | | | | | |
| equation: $-24.6537 + 4.4848 * \Delta Ct_{BLCAP} - 2.1685 * \Delta Ct_{CALM3} + 2.9207 * \Delta Ct_{HIST1H2BK}$ | | | | | | | | | |
| BLCAP | test > 0 | 83 | 27 | OR = 14.30 | 78.6% | 84.7% | 72.4% | 75.5% | 82.6% |
| UBE2G1 | test ? 0 | 15 | 71 | $p < 3.0 \times 10^{-16}$ | | | | | |
| HIST1H2BK | | | | | | | | | |
| equation: $-27.6040 + 1.2774 * \Delta Ct_{BLCAP} + 2.8181 * \Delta Ct_{UBE2G1} + 1.7602 * \Delta Ct_{HIST1H2BK}$ | | | | | | | | | |
| TH1L | test > 0 | 81 | 24 | OR = 14.43 | 79.1% | 82.7% | 75.5% | 77.1% | 81.3% |
| CALM3 | test ? 0 | 17 | 74 | $p < 2 \times 10^{-16}$ | | | | | |
| UBE2G1 | | | | | | | | | |
| equation: $-19.4675 - 2.5799 * \Delta Ct_{TH1L} + 0.9379 * \Delta Ct_{CALM3} + 6.1263 * \Delta Ct_{UBE2G1}$ | | | | | | | | | |
| TH1L | test > 0 | 72 | 35 | OR = 4.94 | 68.9% | 73.5% | 64.3% | 67.3% | 70.8% |
| CALM3 | test ? 0 | 26 | 63 | $p = 1.7 \times 10^{-7}$ | | | | | |
| HIST1H2BK | | | | | | | | | |
| equation: $-17.0992 - 1.3345 * \Delta Ct_{TH1L} - 0.1432 * \Delta Ct_{CALM3} + 2.3132 * \Delta Ct_{HIST1H2BK}$ | | | | | | | | | |
| TH1L | test > 0 | 84 | 24 | OR = 18.13 | 80.6% | 85.7% | 75.5% | 77.8% | 84.1% |
| UBE2G1 | test ? 0 | 14 | 74 | $p < 2 \times 10^{-16}$ | | | | | |
| HIST1H2BK | | | | | | | | | |
| equation: $-23.9436 - 2.0622 * \Delta Ct_{TH1L} + 5.8134 * \Delta Ct_{UBE2G1} + 1.4056 * \Delta Ct_{HIST1H2BK}$ | | | | | | | | | |
| CALM3 | test > 0 | 82 | 25 | OR = 14.70 | 79.1% | 83.7% | 74.5% | 76.6% | 82.0% |
| UBE2G1 | test ? 0 | 16 | 73 | $p < 2 \times 10^{-16}$ | | | | | |
| HIST1H2BK | | | | | | | | | |
| equation: $-26.9573 - 1.7284 * \Delta Ct_{CALM3} + 4.4926 \Delta Ct_{UBE2G1} + 2.016 * \Delta Ct_{HIST1H2BK}$ | | | | | | | | | |

We subsequently analyzed the biomarker performance based on expression levels of combinations of 5 of the 6 genes tested above (Examples 2A, 2B, and 3A), whose combination differentiates between normal and IBD patients (RAP1A, BLCAP, UBE2G1, CALM3, GPX1, and NONO). The classification matrix and diagnostic accuracy estimates of the combination for IBD v Normal, as well as exemplary gene weightings, are shown in Table 18. The equation and weightings for the 5-gene IBD vs Normal combination taught above (RAP1A, BLCAP, UBE2G1, CALM3, and GPX1, Example 2A) are identical to the first combination listed in Table 18. The performance measures in Tables 5a and 5b for set RAP1A, BLCAP, UBE2G1, CALM3, and GPX1) are slightly different because additional patients were included in the Table 18 data: Table 5a summarizes results from 280 patients, and Table 18 summarizes results from 287 patients.

TABLE 18

| combination | | 2 × 2 table | | | accuracy | sensitivity | specificity | PPV | NPV |
|---|---|---|---|---|---|---|---|---|---|
| | | IBD | Normal | fisher's | | | | | |
| RAP1A | test > 0 | 162 | 25 | OR = 17.27 | 81.9% | 85.7% | 74.5% | 86.6% | 73.0% |
| BLCAP | test ? 0 | 27 | 73 | $p < 2 \times 10^{-16}$ | | | | | |
| UBE2G1 | | | | | | | | | |

TABLE 18-continued

GPX1
CALM3
equation: $-10.7716 + 3.2485 * \Delta Ct_{RAP1A} + 5.4360 * \Delta Ct_{BLCAP} - 3.4723 * \Delta Ct_{UBE2G1} - 3.4642 *$
$\Delta Ct_{GPX1} + 3.3511 * \Delta Ct_{CALM3}$

| | | | | | | | | |
|---|---|---|---|---|---|---|---|---|
| RAP1A | test > 0 | 163 | 32 | OR = 12.78 | 79.8% | 86.2% | 67.3% | 83.6% | 71.7% |
| UBE2G1 | test ? 0 | 26 | 66 | $p < 2 \times 10^{-16}$ | | | | | |
| GPX1 | | | | | | | | | |
| CALM3 | | | | | | | | | |
| NONO | | | | | | | | | | equation: $-24.3638 + 3.2362 * \Delta Ct_{RAP1A} + 0.4716 * \Delta Ct_{UBE2G1} - 2.2953 * \Delta Ct_{GPX1} + 2.3207 *$
$\Delta Ct_{CALM3} + 2.3578 * \Delta Ct_{NONO}$

| | | | | | | | | |
|---|---|---|---|---|---|---|---|---|
| RAP1A | test > 0 | 163 | 30 | OR = 14.03 | 80.5% | 86.2% | 69.4% | 84.5% | 72.3% |
| BLCAP | test ? 0 | 26 | 68 | $p < 2 \times 10^{-16}$ | | | | | |
| GPX1 | | | | | | | | | |
| CALM3 | | | | | | | | | |
| NONO | | | | | | | | | | equation: $-22.0546 + 2.9300 * \Delta Ct_{RAP1A} + 1.8471 * \Delta Ct_{BLCAP} - 2.5939 * \Delta Ct_{GPX1} + 2.0732 *$
$\Delta Ct_{CALM3} + 1.5925 * \Delta Ct_{NONO}$

| | | | | | | | | |
|---|---|---|---|---|---|---|---|---|
| RAP1A | test > 0 | 160 | 36 | OR = 9.40 | 77.4% | 84.7% | 63.3% | 81.6% | 68.1% |
| BLCAP | test ? 0 | 29 | 62 | $p = 4.3 \times 10^{-16}$ | | | | | |
| UBE2G1 | | | | | | | | | |
| CALM3 | | | | | | | | | |
| NONO | | | | | | | | | | equation: $-26.4580 + 4.3570 * \Delta Ct_{RAP1A} + 2.2414 * \Delta Ct_{BLCAP} - 1.0652 * \Delta Ct_{UBE2G1} + 0.2504 *$
$\Delta Ct_{CALM3} + 1.2175 * \Delta Ct_{NONO}$

| | | | | | | | | |
|---|---|---|---|---|---|---|---|---|
| RAP1A | test > 0 | 159 | 25 | OR = 15.28 | 80.8% | 84.1% | 74.5% | 86.4% | 70.9% |
| BLCAP | test ? 0 | 30 | 73 | $p < 2 \times 10^{-16}$ | | | | | |
| UBE2G1 | | | | | | | | | |
| GPX1 | | | | | | | | | |
| NONO | | | | | | | | | | equation: $-21.1203 + 4.7113 * \Delta Ct_{RAP1A} + 3.8401 * \Delta Ct_{BLCAP} - 1.7575 * \Delta Ct_{UBE2G1} - 2.2260 *$
$\Delta Ct_{GPX1} + 1.2861 * \Delta Ct_{NONO}$

| | | | | | | | | |
|---|---|---|---|---|---|---|---|---|
| BLCAP | test > 0 | 165 | 31 | OR = 14.67 | 80.8% | 87.3% | 68.4% | 84.2% | 73.6% |
| UBE2G1 | test ? 0 | 24 | 67 | $p < 2 \times 10^{-16}$ | | | | | |
| GPX1 | | | | | | | | | |
| CALM3 | | | | | | | | | |
| NONO | | | | | | | | | | equation: $-9.0048 + 3.6181 * \Delta Ct_{BLCAP} - 1.6280 * \Delta Ct_{UBE2G1} - 3.6336 * \Delta Ct_{GPX1} + 4.4814 *$
$\Delta Ct_{CALM3} + 0.8072 * \Delta Ct_{NONO}$ We subsequently analyzed the biomarker performance based on expression levels of combinations of 6 of the 7 genes tested above (Examples 2E and 3C), whose combination differentiates between IBS and IBD patients (RAP1A, UBE2G1, CALM3, GPX1, HIST1H2BK1, PPP2R5A, and BLCAP). The classification matrix and diagnostic accuracy estimates of the combination for IBS v IBD, as well as exemplary gene weightings, are shown in Table 19.

TABLE 19

| | | 2 x 2 table | | | | | | | |
|---|---|---|---|---|---|---|---|---|---|
| combination | | IBD | IBS | fisher's | | accuracy | sensitivity | specificity | PPV | NPV |
| RAP1A | test > 0 | 168 | 27 | OR = 16.26 | | 81.5% | 86.2% | 72.4% | 85.8% | 73.2% |
| UBE2G1 | test ? 0 | 21 | 71 | $p < 2 \times 10^{-16}$ | | | | | | |
| CALM3 | | | | | | | | | | |
| GPX1 | | | | | | | | | | |
| HIST1H2BK | | | | | | | | | | |
| PPP2R5A | | | | | | | | | | | equation: $16.6895 + 5.155 * \Delta Ct_{RAP1A} - 2.5462 * \Delta Ct_{UBE2G1} + 4.8674 * \Delta Ct_{CALM3} - 2.3979 *$
$\Delta Ct_{GPX1} - 2.8183 * \Delta Ct_{HIST1H2BK} - 2.9778 * \Delta Ct_{PPP2R5A}$

| | | | | | | | | | |
|---|---|---|---|---|---|---|---|---|---|
| RAP1A | test > 0 | 167 | 29 | OR = 17.80 | | 82.2% | 88.4% | 70.4% | 85.2% | 75.8% |
| CALM3 | test ? 0 | 22 | 69 | $p < 2 \times 10^{-16}$ | | | | | | |
| GPX1 | | | | | | | | | | |
| HIST1H2BK | | | | | | | | | | |
| PPP2R5A | | | | | | | | | | |
| BLCAP | | | | | | | | | | | equation: $13.2115 + 4.4136 * \Delta Ct_{RAP1A} + 4.8119 * \Delta Ct_{CALM3} - 2.1923 * \Delta Ct_{GPX1} - 3.0788 *$
$\Delta Ct_{HIST1H2BK} - 3.2874 * \Delta Ct_{PPP2R5A} - 1.3537 * \Delta Ct_{BLCAP}$

| | | | | | | | | | |
|---|---|---|---|---|---|---|---|---|---|
| RAP1A | test > 0 | 168 | 29 | OR = 18.75 | | 82.6% | 88.9% | 70.4% | 85.3% | 76.7% |
| UBE2G1 | test ? 0 | 21 | 69 | $p < 2 \times 10^{-16}$ | | | | | | |
| GPX1 | | | | | | | | | | |
| HIST1H2BK | | | | | | | | | | |
| PPP2R5A | | | | | | | | | | |
| BLCAP | | | | | | | | | | | equation: $14.9114 + 6.8342 * \Delta Ct_{RAP1A} - 6.6508 * \Delta Ct_{UBE2G1} - 1.5818 * \Delta Ct_{GPX1} - 1.3437 *$
$\Delta Ct_{HIST1H2BK} - 2.0964 * \Delta Ct_{PPP2R5A} + 4.3897 * \Delta Ct_{BLCAP}$ TABLE 19-continued

| | | | | | | | | | |
|---|---|---|---|---|---|---|---|---|---|
| RAP1A | test > 0 | 171 | 31 | OR = 20.22 | 82.9% | 90.5% | 68.4% | 84.7% | 78.8% |
| UBE2G1 | test ? 0 | 18 | 67 | $p < 2 \times 10^{-16}$ | | | | | |
| CALM3 | | | | | | | | | |
| HIST1H2BK | | | | | | | | | |
| PPP2R5A | | | | | | | | | |
| BLCAP | | | | | | | | | | equation: $6.224 + 7.0296 * \Delta Ct_{RAP1A} - 5.2346 * \Delta Ct_{UBE2G1} + 1.0171 * \Delta Ct_{CALM3} - 1.8810 * \Delta Ct_{HIST1H2BK} - 2.1413 * \Delta Ct_{PPP2R5A} + 2.7922 * \Delta Ct_{BLCAP}$

| | | | | | | | | | |
|---|---|---|---|---|---|---|---|---|---|
| RAP1A | test > 0 | 166 | 29 | OR = 16.93 | 81.9% | 87.8% | 70.4% | 85.1% | 75.0% |
| UBE2G1 | test ? 0 | 23 | 69 | $p < 2 \times 10^{-16}$ | | | | | |
| CALM3 | | | | | | | | | |
| GPX1 | | | | | | | | | |
| PPP2R5A | | | | | | | | | |
| BLCAP | | | | | | | | | | equation: $14.1274 + 5.8613 * \Delta Ct_{RAP1A} - 7.1962 * \Delta Ct_{UBE2G1} + 1.1262 * \Delta Ct_{CALM3} - 2.1478 * \Delta Ct_{GPX1} - 2.2727 * \Delta Ct_{PPP2R5A} + 4.7122 * \Delta Ct_{BLCAP}$

| | | | | | | | | | |
|---|---|---|---|---|---|---|---|---|---|
| UBE2G1 | test > 0 | 165 | 39 | OR = 10.29 | 78.0% | 87.3% | 60.2% | 80.9% | 71.1% |
| CALM3 | test ? 0 | 24 | 59 | $p < 2 \times 10^{-16}$ | | | | | |
| GPX1 | | | | | | | | | |
| HIST1H2BK | | | | | | | | | |
| PPP2R5A | | | | | | | | | |
| BLCAP | | | | | | | | | | equation: $21.6433 - 3.1122 * \Delta Ct_{UBE2G1} + 5.9519 * \Delta Ct_{CALM3} - 3.2758 * \Delta Ct_{GPX1} - 2.2307 * \Delta Ct_{HIST1H2BK} - 1.2969 * \Delta Ct_{PPP2R5A} + 1.5055 * \Delta Ct_{BLCAP}$

| | | | | | | | | | |
|---|---|---|---|---|---|---|---|---|---|
| RAP1A | test > 0 | 164 | 29 | OR = 15.40 | 81.2% | 86.8% | 70.4% | 85.0% | 73.4% |
| UBE2G1 | test ? 0 | 25 | 69 | $p < 2 \times 10^{-16}$ | | | | | |
| CALM3 | | | | | | | | | |
| GPX1 | | | | | | | | | |
| HIST1H2BK | | | | | | | | | |
| BLCAP | | | | | | | | | | equation: $12.5376 + 4.5779 * \Delta Ct_{RAP1A} - 6.7553 * \Delta Ct_{UBE2G1} + 2.5618 * \Delta Ct_{CALM3} - 2.1679 * \Delta Ct_{GPX1} - 1.9711 * \Delta Ct$

We claim:

1. A method for diagnosing whether a human subject is likely to have inflammatory bowel disease (IBD), comprising:

(a) contacting a mRNA-derived nucleic acid sample obtained from a human subject suspected of having IBD under hybridizing conditions with at least six 5 nucleotide probes, wherein a first nucleotide probe consists of 15 or more contiguous nucleotides of SEQ ID NO:3

(BLCAP) or a full complement thereof, a second nucleotide probe consists of 15 or more contiguous nucleotides of SEQ ID NO:5 (UBE2G1) or a full complement thereof, a third nucleotide probe consists of 15 or more contiguous nucleotides of SEQ ID NO:6 (CALM3) or a full complement thereof, a fourth nucleotide probe consists of 15 or more contiguous nucleotides of SEQ ID NO:13 (NONO) or a full complement thereof, and a fifth nucleotide probe and a sixth nucleotide probe consist of 15 or more contiguous nucleotides of a nucleic acid selected from the group consisting of:
  (i) SEQ ID NO:1 (RAP1A) and SEQ ID NO:7 (GPX1) or full complements thereof;
  (ii) SEQ ID NO:2 (RAP1A) and SEQ ID NO:7 (GPX1) or full complements thereof;
  (iii) SEQ ID NO:1 (RAP1A) and SEQ ID NO:8 (GPX1) or full complements thereof; and
  (iv) SEQ ID NO:2 (RAP1A) and SEQ ID NO:8 (GPX1) or full complements thereof;
(b) detecting formation of hybridization complexes between the nucleotide probes and the nucleic acid targets in the nucleic acid sample, wherein the hybridization complexes provide a measure of gene expression of the nucleic acid targets; and
(c) diagnosing whether the human subject is likely to have IBD based on the measure of gene expression of the nucleic acid targets, wherein gene expression levels of the nucleic acid targets differentiate between IBD and normal.

2. The method of claim 1, wherein the human subject suffers from one or more of abdominal pain, constipation, diarrhea, a change in bowel habits, vomiting, hematochezia, and weight change.

3. The method of claim 1, wherein the mRNA-derived nucleic acid sample is obtained from peripheral blood mononuclear cells or red blood cell-depleted whole blood.

4. The method of claim 1, further comprising analyzing gene expression of the nucleic acid targets by applying a weight to the number of hybridization complexes formed for each nucleic acid target.

5. A method for diagnosing whether a human subject is likely to have inflammatory bowel disease (IBD), comprising:
  (a) contacting a mRNA-derived nucleic acid sample obtained from a human subject suspected of having IBD under amplifying conditions with at least six primer pairs, wherein a first primer pair selectively amplifies a detectable portion of SEQ ID NO:3 (BLCAP) or a full complement thereof, a second primer pair selectively amplifies a detectable portion of SEQ ID NO:5 (UBE2G1) or a full complement thereof, a third primer pair selectively amplifies a detectable portion of SEQ ID NO:6 (CALM3) or a full complement thereof, a fourth primer pair selectively amplifies a detectable portion of SEQ ID NO:13 (NONO) or a full complement thereof, and a fifth primer pair and a sixth primer pair selectively amplify a detectable portion of a nucleic acid selected from the group consisting of:
  (i) SEQ ID NO:1 (RAP1A) and SEQ ID NO:7 (GPX1) or full complements thereof;
  (ii) SEQ ID NO:2 (RAP1A) and SEQ ID NO:7 (GPX1) or full complements thereof;
  (iii) SEQ ID NO:1 (RAP1A) and SEQ ID NO:8 (GPX1) or full complements thereof; and
  (iv) SEQ ID NO:2 (RAP1A) and SEQ ID NO:8 (GPX1) or full complements thereof; wherein each primer in each primer pair consists of at least 15 contiguous nucleotides of its respective nucleic acid target;
(b) detecting amplification products generated by amplification of nucleic acid targets in the nucleic acid sample by the at least six primer pairs, wherein the amplification products provide a measure of gene expression of the nucleic acid targets; and
(c) diagnosing whether the human subject is likely to have IBD based on the measure of gene expression of the nucleic acid targets, wherein gene expression levels of the nucleic acid targets differentiate between IBD and normal.

6. The method of claim 5, wherein the human subject suffers from one or more of abdominal pain, constipation, diarrhea, a change in bowel habits, vomiting, hematochezia, and weight change.

7. The method of claim 5, wherein the mRNA-derived nucleic acid sample is obtained from peripheral blood mononuclear cells or red blood cell-depleted whole blood.

8. The method of claim 5, further comprising analyzing gene expression of the nucleic acid targets by applying a weight to the number of amplification products formed for each nucleic acid target.

* * * * *

SEQUENCE LISTING

```
<160> NUMBER OF SEQ ID NOS: 16

<210> SEQ ID NO 1
<211> LENGTH: 1906
<212> TYPE: DNA
<213> ORGANISM: Homo sapiens

<400> SEQUENCE: 1
ggcgccgccg ccgctcccga ggcccctgcc gccgccgctc ccgctgctgt cgccgcgcag      60
agccggagca ggagccacgg ccgagaggag ggaggaggag gaggaggagg tggaggaggt     120
ggaggaggtg gaggaggcgc cggaccgggg gggatagatt cccagaagtg ggataactgg     180
atcagagggt gattaccctg tgtataagag tatgtgtctc actgcacctt caatggcatt     240
gagtagatcg tcagtattta aacagatcac atcatgcgtg agtacaagct agtggtcctt     300
ggttcaggag gcgttgggaa gtctgctctg acagttcagt tgttcaggg aatttttgtt      360 gaaaaatatg acccaacgat agaagattcc tacagaaagc aagttgaagt cgattgccaa     420
cagtgtatgc tcgaaatcct ggatactgca gggacagagc aatttacagc aatgagggat     480
ttgtatatga agaacggcca aggttttgca ctagtatatt ctattacagc tcagtccacg     540
tttaacgact tacaggacct gagggaacag attttacggg ttaaggacac ggaagatgtt     600
ccaatgattt tggttggcaa taaatgtgac ctggaagatg agcgagtagt tggcaaagag     660
cagggccaga atttagcaag acagtggtgt aactgtgcct ttttagaatc ttctgcaaag     720
tcaaagatca atgttaatga gatatttat gacctggtca gacagataaa taggaaaaca     780
ccagtggaaa agaagaagcc taaaaagaaa tcatgtctgc tgctctaggc ccatagtcag     840
cagcagctct gagccagatt acaggaatga agaactgttg cctaattgga aagtgccagc     900
```

-continued

```
attccagact tcaaaaataa aaaatctgaa gaggcttctc ctgttttata tattatgtga      960
agaatttaga tcttatattg gtttgcacaa gttccctgga gaaaaaaatt gctctgtgta     1020
tatctcttgg aaaataagac aatagtattt ctcctttgca atagcagtta taacagatgt     1080
gaaaatatac ttgactctaa tatgattata caaaagagca tggatgcatt tcaaatgtta     1140
gatattgcta ctataatcaa atgatttcat attgatcttt ttatcatgat cctccctatc     1200
aagcactaaa aagttgaacc attatacttt atatctgtaa tgatactgat tatgaaatgt     1260
cccctcaaac tcattgcagc agataacttt tttgagtcat tgacttcatt ttatatttaa     1320
aaaattatgg aatatcatct gtcattatat tctaattaaa attgtgcata atgctttgga     1380
aaaatgggtc ttttatagga aaaaaactgg gataactgat ttctatggct ttcaaagcta     1440
aaatatataa tatactaaac caactctaat attgcttctt gtgttttact gtcagattaa     1500
attacagctt ttatggatga ttaaatttta gtacatttc atttggtttg tgtgtttttg      1560
ttattgttta tagattaaag cgtttatttt ataatgacca cattgtttta aatgcgacag     1620
tagctccttt ctgcctagta tctgcagaac actggcttta aactatacta agtaactggt     1680
gatttctcta ggaacagacc tcgcactttc tgttctaaat atatttattc ctactataca     1740
gtaaaataca tcagacaaca tagaatagtt ttgtatattc tctcttgatc ttaaagattg     1800
tatcttattg aatatcccac tgtatattat ttttatatgt aaaaagataa gtttaatact     1860
gtatcagggt ttaacttta ctatttcaga tcttccacag cttgta                     1906

<210> SEQ ID NO 2
<211> LENGTH: 1812
<212> TYPE: DNA
<213> ORGANISM: Homo sapiens

<400> SEQUENCE: 2
ggcgccgccg ccgctcccga ggcccctgcc gccgccgctc ccgctgctgt cgccgcgcag       60
agccggagca ggagccacgg ccgagaggag ggaggaggag gaggaggagg tggaggaggt      120
ggaggaggtg gaggaggcgc cggaccgggg ggatcgtcag tatttaaaca gatcacatca      180
tgcgtgagta caagctagtg gtccttggtt caggaggcgt tgggaagtct gctctgacag      240
ttcagtttgt tcagggaatt tttgttgaaa aatatgaccc aacgatagaa gattcctaca     300
gaaagcaagt tgaagtcgat tgccaacagt gtatgctcga atcctggat actgcaggga      360
cagagcaatt tacagcaatg agggatttgt atatgaagaa cggccaaggt tttgcactag      420
tatattctat tacagctcag tccacgttta acgacttaca ggacctgagg gaacagattt      480
tacgggttaa ggacacggaa gatgttccaa tgattttggt tggcaataaa tgtgaccctg     540
aagatgagcg agtagttggc aaagagcagg gccagaattt agcaagacag tggtgtaact      600
gtgcctttt agaatcttct gcaaagtcaa agatcaatgt taatgagata ttttatgacc       660
tggtcagaca gataaatagg aaaacaccag tggaaaagaa gaagcctaaa aagaaatcat      720
gtctgctgct ctaggcccat agtcagcagc agctctgagc cagattacag gaatgaagaa      780
ctgttgccta attggaaagt gccagcattc cagacttcaa aaataaaaaa tctgaagagg      840
cttctcctgt tttatatatt atgtgaagaa tttagatctt atattggttt gcacaagttc      900
cctggagaaa aaaattgctc tgtgtatatc tcttggaaaa taagacaata gtatttctcc      960
tttgcaatag cagttataac agatgtgaaa atatacttga ctctaatatg attatacaaa     1020
agagcatgga tgcatttcaa atgttagata ttgctactat aatcaaatga tttcatattg     1080
```

```
atcttttat catgatcctc cctatcaagc actaaaaagt tgaaccatta tactttatat      1140
ctgtaatgat actgattatg aaatgtcccc tcaaactcat tgcagcagat aactttttg      1200 agtcattgac ttcattttat atttaaaaaa ttatggaata tcatctgtca ttatattcta     1260
attaaaattg tgcataatgc tttggaaaaa tgggtctttt ataggaaaaa aactgggata    1320
actgatttct atggctttca aagctaaaat atataatata ctaaaccaac tctaatattg    1380
cttcttgtgt tttactgtca gattaaatta cagcttttat ggatgattaa attttagtac   1440
attttcattt ggtttgtgtg ttttgttat tgtttataga ttaaagcgtt tattttataa    1500
tgaccacatt gttttaaatg cgacagtagc tcctttctgc ctagtatctg cagaacactg   1560
gctttaaact atactaagta actggtgatt tctctaggaa cagacctcgc actttctgtt   1620
ctaaatatat ttattcctac tatacagtaa aatacatcag acaacataga atagttttgt   1680
atattctctc ttgatcttaa agattgtatc ttattgaata tcccactgta tattatttt    1740 atatgtaaaa agataagttt aatactgtat cagggtttaa ctttactat ttcagatctt    1800 ccacagcttg ta                                                       1812

<210> SEQ ID NO 3
<211> LENGTH: 2057
<212> TYPE: DNA
<213> ORGANISM: Homo sapiens

<400> SEQUENCE: 3
gactaagggg gcgtctcccc ggcttcctgc ggcgtcggtg gcgagctgag gtggaggcag      60
gctgcggcag acggcgacag tggcggcggc gccatggcag ggcttgcagg atccctgctg     120
ccttggtgat cccgggctga cagccagaga gcacagcggc tcagctcctg gagagtgagg    180
gttgaagaaa gcggagggca gccgcctgcg cccgctggct cccattaggt cggttcctgc    240
agcggtgccc ggcagccttg gtgaaggccc tgcccggcag agatcatgta ttgcctccag    300
tggctgctgc ccgtcctcct catccccaag cccctcaacc ccgccctgtg gttcagccac    360
tccatgttca tgggcttcta cctgctcagc ttcctcctgg aacggaagcc ttgcacaatt    420
tgtgccttgg ttttcctggc agccctgttc cttatctgct atagctgctg gggaaactgt    480
ttcctgtacc actgctccga ttccccgctt ccagaatcgg cgcatgatcc cggcgttgtg    540
ggcacctaac ggcctgccct gttagctttc caaggaagca gaagacggga ggggaggcat    600
tgacataggt cataaagcat tggagtttca aatcccgcag cctcgcgggt gtcacattcc    660
tgacggcgcc ttttggcct gtgatgtttt atccttacaa tgtgaataat ggcactgacc     720
ggtgctttta ttgtaaagtc ctatagtcgt gggtggtctt gtggttgtgt gtgttctgtc   780
cccatctagg tcctggctgg ccgcatgacc accctctcg cctcattact gtgaggagtc    840
tgggtccatc ctggtcagct gccccaatgt gacctggggc agataaaatg ccagtctcat    900
tgtcacctct gtgaccctc cttgtcaggg tctccttcct tcccagaatg ttactgactc    960
ctcagtccct cttctggttt cccttattt ctcttctacc cttttccttt ttggggagt    1020 acctgtccaa gacagggctc attttgcac ttatctcgaa tttgaagaga ttgctgacgc    1080
ccgagagcct cgcttttca tccttctttc cttgttcagc aggctagaca gaaacatgtc    1140
ttgactgtta gttgtccaca atcttcagt attttctcca cttcattttt aagaaaggaa    1200
gcaacagata gatgttgctc tttcacctgg gtgtctgggc tcaagctttc ccgcccagcc    1260
tcacttcctt tgcccttcct cctgcctttc tcaactgtcc caaggagggg gcctcattgt   1320
gtctcccgtg catgctctgc agcattgaag tatggtgtgt tcacgtagtt ctagcagtcc   1380
```

```
ccagctgagt gagtgggaga gtacctgtgt gtttcgtaac ggccttgatc cccttgatag    1440
atgtttggat attttttggt gtgccctgtg tgtgtgtgtg tacaaataca tgtgtatatt    1500
ccttttaaag aagctttatc gaacgtggtc tgattttgag gtttagcaat agctagctat    1560
atatggtagg tgccgctaca gttttatttt agcatgggga ttgcagagtg accagcacac    1620
tggactccga ggtggttcag acaagacaga ggggagcagt ggccatcatc ctcccgccag    1680
gagcttcttc gttcctgcgc atatagactg tacattatga agaataccca ggaagacttt    1740
gtgactgtca cttgctgctt tttctgcgct tcagtaacaa gtgttggcaa acgagacttt    1800
ctcctggccc ctgcctgctg agatcagca tgcctgtcct ttcagtctga tccatccatc     1860
tctctcttgc ctgaggggaa agagagatgg gccaggcaga aacagaact ggaggcagtc     1920 catctaggga atgggactgt gaggccatac ttgtgaaacg tctggactgc tattctagag    1980
cttttatttg gtgtgttcgt tgcacagctg tttgaaatgt ttaataaagc tttataaact    2040
ttaaaaaaaa aaaaaaa                                                    2057

<210> SEQ ID NO 4
<211> LENGTH: 2263
<212> TYPE: DNA
<213> ORGANISM: Homo sapiens

<400> SEQUENCE: 4
atgcgccgcg ctcgctcgcg ggagggcatg gcggggccg tgccgggcgc catcatggac       60
gaggactact acgggagcgc ggccgagtgg ggcgacgagg ctgacggcgg ccagcaggag     120
gatgattctg gagaaggaga ggatgatgcg gaggttcagc aagaatgcct gcataaattt     180
tccacccggg attatatcat ggaaccctcc atcttcaaca ctctgaagag gtattttcag     240
gcaggagggt ctccagagaa tgttatccag ctcttatctg aaaactacac cgctgtggcc     300
cagactgtga acctgctggc cgagtggctc attcagacag tgttgagcc agtgcaggtt     360 caggaaactg tggaaaatca cttgaagagt ttgctgatca acatttttga cccccgcaaa    420
gcagattcta ttttactga agaaggagag accccagcgt ggctggaaca gatgattgca     480
cataccacgt ggcgggacct tttttataaa ctggctgaag cccatccaga ctgtttgatg    540
ctgaacttca ccgttaagct tatttctgac gcagggtacc agggggagat caccagtgtg    600
tccacagcat gccagcagct agaagtgttc tcgagagtgc tccggacctc tctagctaca    660
attttagatg gaggagaaga aaaccttgaa aaaaatctcc ctgagtttgc caagatggtg    720
tgccacgggg agcacacgta cctgtttgcc caggccatga tgtccgtgct ggcccaggag    780
gagcaggggg gctccgctgt gcgcaggatc gcccaggaag tgcagcgctt tgcccaggag    840
aaaggtcatg acgccagtca gatcacacta gccttgggca cagctgcctc ctaccccagg    900
gcctgccagg ctctcgggc catgctgtcc aaaggagccc tgaaccctgc tgacatcacc    960
gtcctgttca agatgttcac aagcatggac cctcctccgg ttgaacttat ccgcgttcca    1020
gccttcctgg acctgttcat gcagtcactc tttaaaccag gggctcggat caaccaggac    1080
cacaagcaca atacatcca catcttggcg tacgcagcaa gcgtggttga acctggaag     1140 aagaacaagc gagtgagcat caataaagat gagctgaagt caacgtcaaa agctgtcgaa    1200
accgttcaca atttgtgttg caacgagaac aaagggggcct ctgaactagt ggcagaattg   1260
agcacacttt atcagtgtat taggttttcca gtggtagcaa tgggtgtgct gaagtgggtg   1320
gattggactg tatcagaacc aaggtacttt cagctgcaga ctgaccatac ccctgtccac   1380
```

-continued

```
ctggcgttgc tggatgagat cagcacctgc caccagctcc tgcaccccca ggtcctgcag    1440
ctgcttgtta agcttttga gactgagcac tcccagctgg acgtgatgga gcagcttgag     1500
ttgaagaaga cactgctgga caggatggtt cacctgctga gtcgaggtta tgtacttcct    1560
gttgtcagtt acatccgaaa gtgtctggag aagctggaca ctgacatttc actcattcgc    1620
tattttgtca ctgaggtgct ggacgtcatt gctcctcctt atacctctga cttcgtgcaa    1680
cttttcctcc ccatcctgga gaatgacagc atcgcaggta ccatcaaaac ggaaggcgag    1740
catgaccctg tgacggagtt tatagctcac tgcaaatcta acttcatcat ggtgaactaa    1800
tttagagcat cctccagagc tgaagcagaa cattccagaa cccgttgtgg aaaaacccctt   1860 tcaagaagct gttttaagag gctcgggcag cgtcttgaaa atgggcaccg ctgggaggag    1920
gtggatgact tctttacaaa ggaaaatggt agcagcttca gtgagaaact gcccttacaa    1980
acagtccctt ctctgctgtc aatccaatac tgctcccaaa tcctgttttc agtgttcatt    2040
tccctcaagg caggcgctgg gctcccacga cccctcagga cagatctggc cgtcagccgc    2100
gggccgctgg gaactccact cggggaactc cttttccaagc tgacctcagt tttctcacaa   2160
gaacccagtt agctgatgtt ttattgtaat tgtcttaatt tgctaagaac aagtaataag    2220
taaattttta aaaagccttt ctgctgggtt ggattaaaaa aaa                      2263

<210> SEQ ID NO 5
<211> LENGTH: 4208
<212> TYPE: DNA
<213> ORGANISM: Homo sapiens

<400> SEQUENCE: 5
gtctcagcgc gcctgcgccg agcggccctg cgcgcagtga ggcagtggcg ggggaaggca      60
ccggtggggc cgacgggcgg gttgaaggag ggaagcgggc gagcgaagtc ccagtgcgcg     120
ccgcggcagc ccgggcaccc tccccttccg ggcgtgagtc gctgtgaaaa gagctgaagc     180
gagcggactc gcaccggcag cgaggcgccg ctcccgccgc ctcagcccgg ccttcctcgg     240
ctccggcgct ccggtcgcgg ggcccggggtt cctcggcaca ccccgctcca gccgcccccca   300 gagcctgtcc ccagcccttc ggaagccccg cgccagccc gggccctcgg cagggaggat     360
gacggagctg cagtcggcac tgctactgcg aagacagctg gcagaactca acaaaaatcc    420
agtggaaggc ttttctgcag gtttaataga tgacaatgat ctctaccgat gggaagtcct    480
tattattggc cctccagata cactttatga aggtggtgtt tttaaggctc atcttacttt    540
cccaaaagat tatcccctcc gacctcctaa aatgaaattc attacagaaa tctggcaccc    600
aaatgttgat aaaaatggtg atgtgtgcat ttctattctt catgagcctg gggaagataa    660
gtatggttat gaaaagccag aggaacgctg gctcccctatc cacactgtgg aaaccatcat    720
gattagtgtc atttctatgc tggcagaccc taatggagac tcacctgcta atgttgatgc    780
tgcgaaagaa tggagggaag atagaaatgg agaatttaaa agaaagttg cccgctgtgt    840 aagaaaaagc caagagactg cttttgagtg acatttattt agcagctagt aacttcactt    900
atttcagggt ctccaattga gaaacatggc actgtttttc ctgcactcta cccacctatt    960
gctggacttc tgttgtacaa gttggcaaac actggctgga actgggctgc aataaaacat   1020
gccagttatc aatgctgaca agagcctaac aagtgccaac ttacagatga ttacgcattt   1080
tgaattctaa tgaactgttt taaccttcag gaagaattgt aaagacctgt acatagcaca   1140
acatgatccg gataatatat atactgttca gtgtacatcca caaatacacc ttgtaccaaa   1200
taatgctttc ttgtagtaga ataagaatcg tgtaaattct aagagatttt agcaggtttt    1260
```

```
ctttcctatt cattgtttct tatcagttta aaaggattcc tttaagcatg tcagatgaaa    1320
agcaattagg attaaaagtt tccatttaat ttcccttaaa cccttgaggc ttcattaaac    1380
tcttttcact tactaaactt ttgtatcttc tttgttttga cactccccc tttgctttta    1440 tctcttacct gccagaatgt tctcaaatga tttagttcaa atactgaaat acttaatgag    1500
caattacttg atttttaatg atgacttcga aggagtcatc actaggtgct ttgtcctttt    1560
tgtattctag ttgcacccac ctcttggatt ggatatagca ataacattta ttggccgttg    1620
tgagctcttg atcccagtca ttacccctga aactaaaaa tagatggttc ttaattcaac    1680
ttactgaaaa tttccccaaa caatagcaaa tctgactttt ccctcttcag ttgcctggta    1740
ttaaggttgg ataaatgaag catgcacagc tacaggcttt ctacttaact tctgggtttg    1800
ctattacaaa tcctatttac tctcataccc ttctccttag tccttcatat ttctctgcct    1860
ctattcttct atactgcaga ttttttctcac ctattgtaca aagaaattgc gatgtatatt    1920
ttcatgtaat ttgattttgg aattctgtca ccttatgtag tgagttcttc caaaatataa    1980
ttttttttca ataattgtca agttgttggc ttttattgta ttgaatgaag ctataaatac    2040
tgagtgccag agaagtggtt taggaaaatc tcaggttgat tccttatgca aatgaacttt    2100
taatacttga aaatcacatg gccatggcag tatatgtatt tggttctatc tagattcttc    2160
tgtgaatcta aaagcattac aggggtaaat gctttgctat ttgacgtata gatcccgtca    2220
ctaacaatag tacacttgga tgtgattaat gtttgagctt caatatattt catatcatac    2280
agttttctaa aacaacttca gcaaatggta aaatgaacat gtgcagtgtt aaaggcaggc    2340
cttaggctcc ttcatgtttg ttgtgaggtt gtgtgtggga agtagtcttt ggcttataag    2400
ggatagaact tgagacagta gcagatggga catggtgttt gattgtgaga atcagtgaga    2460
attcgtgcat ctctgctctg tggggtttgg agaaatgctt tggcagaaga gtgaaagaac    2520
tcctgccaag agcccagacc tctacaaacg ttgtatgtcc tttttaagc agaaataaaa    2580 tggttgagga tgtagtcaca gtagagagtg attttttttct aagtccctgt cctctactct    2640
gaagcgttat aaaaacctgt aaacattata caaacccaca aaccttatag aaactcgtaa    2700
gtgtgttgtg actggaaatt gattcattag aacccagttt tctttaagaa ctttgtgact    2760 tggtttttt tttcctttc caaagactgt aaaaatagtt gccccaaaat gtcagcactg    2820
cacaccctcc agggacttgg aatacaatcc tttttacttt tttttttttt ttttttaagaa    2880 actgggtctc tctgtcaccc aggctggagt gcagtggcaa cgatcatagc taactgcagc    2940
tttgacctcc tgggctcaag tgatcctcct gcctcagcct cctgagtagc taggactaca    3000
ggtgtatgcc accatgcctg gctaatacaa aaaaattctt ttaagagatg ggatccctcc    3060
cttttaaaat cagaacttgt tcacatggtg gttgcttgtg gcaaaacgga gttcaaattt    3120
tgctctccta ttgctataat tctgctagca atctgttgag gtgaaacttg ggatctgact    3180
cttcagcaag cagcaaatga cctagtaact cagggacaac tatttttgaa ctttaagtgc    3240
cactttaatg cagttagttt gataaaacca tgtgggtttt tttttaggg ctagctctac    3300 gggagtggaa gtgagagcca ggcatgagtg cgtctccaca tgcttttcca cctgccctga    3360
gtgtgttaca tactgaaaca ggcctacata gatgttacaa cttcccttcc tctgtcggag    3420
atgtcatctg tgcctttctc agtgttcatc tgataatgta aatttaaatg cctctacatt    3480
tgatacgaaa cccacattca ggtgacactg aacgaggtgg cttttgtccc accagtgcct    3540
catcagtgtg aggcgattcc tctctgcttt aggaaaatga ttttcccccc taaacttgtg    3600
```

-continued

| | |
|---|---|
| ccaaccatca acaacatctc catagatctt atggattgta gaactgttgg ctgtttccta | 3660 |
| aatttattcc aagttctcgt agaggcatat agatttcagt ctgtgcttgt atgggataga | 3720 |
| tgatctgagt ggcttctgg cctctttttt gagtttaaaa tccatatgag gttgacgtgt | 3780 |
| catactaagg taacatgttt gtgaggttat tccactagta ctgtgatcac gtgggtgtca | 3840 |
| gtatctttaa cggccttcat tcttggttgt gagattttat ttgatatgcc cactcaccct | 3900 |
| cgacgaatct gcccgctttg ggctgtggtg cctgtgtatc tttgcccgtc tggtctccag | 3960 |
| ttggtggaat tacctttttt gtactgccac ttctcagcat cttgaaatt tgacataatg | 4020 |
| ttgcttcatt tcagttttt tagttctgta atttgttgat tgtatttaac tatgtgagtt | 4080 |
| ctgttgtgat gtttactgta ttgtaaagca cctcattcat gtgatgagtg ctctataaat | 4140 |
| caataaatga tgacttagag gctgtatcac gagctatttt ggttttagga tgcaggtctc | 4200 |
| aaaagcaa | 4208 |

<210> SEQ ID NO 6
<211> LENGTH: 2277
<212> TYPE: DNA
<213> ORGANISM: Homo sapiens

<400> SEQUENCE: 6

| | |
|---|---|
| ggcggggcgc gcgcggcggc cgttgaggga ccgttggggc gggaggcggc ggcggcggcg | 60 |
| gcgcgcgctg cgggcagtga gtgtggaggc gcggacgcgc ggcggagctg gaactgctgc | 120 |
| agctgctgcc gccgccggag gaaccttgat ccccgtgctc cggacacccc gggcctcgcc | 180 |
| atggctgacc agctgactga ggagcagatt gcagagttca aggaggcctt ctccctctt | 240 |
| gacaaggatg gagatggcac tatcaccacc aaggagttgg ggacagtgat gagatccctg | 300 |
| ggacagaacc ccactgaagc agagctgcag gatatgatca atgaggtgga tgcagatggg | 360 |
| aacgggacca ttgacttccc ggagttcctg accatgatgg ccagaaagat gaaggacaca | 420 |
| gacagtgagg aggagatccg agaggcgttc cgtgtctttg acaaggatgg gaatggctac | 480 |
| atcagcgccg cagagctgcg tcacgtaatg acgaacctgg gggagaagct gaccgatgag | 540 |
| gaggtggatg agatgatcag ggaggctgac atcgatggag atggccaggt caattatgaa | 600 |
| gagtttgtac agatgatgac tgcaaagtga aggcccccg ggcagctggc gatgcccgtt | 660 |
| ctcttgatct ctctcttctc gcgcgcgcac tctctcttca acactcccct gcgtaccccg | 720 |
| gttctagcaa acaccaattg attgactgag aatctgataa agcaacaaaa gatttgtccc | 780 |
| aagctgcatg attgctcttt ctccttcttc cctgagtctc tctccatgcc cctcatctct | 840 |
| tccttttgcc ctcgcctctt ccatccatgt cttccaaggc ctgatgcatt cataagttga | 900 |
| agccctcccc agatcccctt ggggagcctc tgccctcctc cagcccggat ggctctcctc | 960 |
| cattttggtt tgtttcctct tgtttgtcat cttattttgg gtgctggggt ggctgccagc | 1020 |
| cctgtcccgg gacctgctgg gagggacaag aggccctccc ccaggcagaa gagcatgccc | 1080 |
| tttgccgttg catgcaacca gccctgtgat tccacgtgca gatcccagca gcctgttggg | 1140 |
| gcaggggtgc caagagaggc attccagaag gactgagggg gcgttgagga attgtggcgt | 1200 |
| tgactggatg tggcccagga gggggtcgag ggggccaact cacagaaggg gactgacagt | 1260 |
| gggcaacact cacatcccac tggctgctgt tctgaaacca tctgattggc tttctgaggt | 1320 |
| ttggctgggt ggggactgct catttggcca ctctgcaaat tggacttgcc cgcgttcctg | 1380 |
| aagcgctctc gagctgttct gtaaatacct ggtgctaaca tcccatgccg ctccctcctc | 1440 |
| acgatgcacc caccgccctg agggcccgtc ctaggaatgg atgtggggat ggtcgctttg | 1500 |

| | |
|---|---|
| taatgtgctg gttctctttt tttttctttc ccctctatgg cccttaagac tttcattttg | 1560 |
| ttcagaacca tgctgggcta gctaaagggt ggggagaggg aagatgggcc ccaccacgct | 1620 |
| ctcaagagaa cgcacctgca ataaaacagt cttgtcggcc agctgcccag gggacggcag | 1680 |
| ctacagcagc ctctgcgtcc tggtccgcca gcacctcccg cttctccgtg gtgacttggc | 1740 |
| gccgcttcct cacatctgtg ctccgtgccc tcttccctgc ctcttccctc gcccacctgc | 1800 |
| ctgcccccat actcccccag cggagagcat gatccgtgcc cttgcttctg actttcgcct | 1860 |
| ctgggacaag taagtcaatg tgggcagttc agtcgtctgg gttttttccc cttttctgtt | 1920 |
| catttcatct ggctcccccc accacctccc caccccaccc cccaccccct gcttcccctc | 1980 |
| actgcccagg tcgatcaagt ggcttttcct gggacctgcc cagctttgag aatctcttct | 2040 |
| catccaccct ctggcaccca gcctctgagg gaaggaggga tggggcatag tgggagaccc | 2100 |
| agccaagagc tgagggtaag ggcaggtagg cgtgaggctg tggacatttt cggaatgttt | 2160 |
| tggttttgtt tttttttaaac cgggcaatat tgtgttcagt tcaagctgtg aagaaaaata | 2220 |
| tatatcaatg ttttccaata aaatacagtg actacctgaa aaaaaaaaaa aaaaaaa | 2277 |

<210> SEQ ID NO 7
<211> LENGTH: 921
<212> TYPE: DNA
<213> ORGANISM: Homo sapiens

<400> SEQUENCE: 7

| | |
|---|---|
| cagttaaaag gaggcgcctg ctggcctccc cttacagtgc ttgttcgggg cgctccgctg | 60 |
| gcttcttgga caattgcgcc atgtgtgctg ctcggctagc ggcggcggcg gcggcggccc | 120 |
| agtcggtgta tgccttctcg gcgcgcccgc tggccggcgg ggagcctgtg agcctgggct | 180 |
| ccctgcgggg caaggtacta cttatcgaga atgtggcgtc cctctgaggc accacggtcc | 240 |
| gggactacac ccagatgaac gagctgcagc ggcgcctcgg accccggggc ctggtggtgc | 300 |
| tcggcttccc gtgcaaccag tttgggcatc aggagaacgc caagaacgaa gagattctga | 360 |
| attccctcaa gtacgtccgg cctggtggtg ggttcgagcc caacttcatg ctcttcgaga | 420 |
| agtgcgaggt gaacggtgcg ggggcgcacc ctctcttcgc cttcctgcgg gaggccctgc | 480 |
| cagctcccag cgacgacgcc accgcgctta tgaccgaccc caagctcatc acctggtctc | 540 |
| cggtgtgtcg caacgatgtt gcctggaact ttgagaagtt cctggtgggc cctgacggtg | 600 |
| tgccccctacg caggtacagc cgccgcttcc agaccattga catcgagcct gacatcgaag | 660 |
| ccctgctgtc tcaagggccc agctgtgcct agggcgcccc tcctacccc gctgcttggc | 720 |
| agttgcagtg ctgctgtctc ggggggggttt tcatctatga gggtgtttcc tctaaaccta | 780 |
| cgagggagga acacctgatc ttacagaaaa taccacctcg agatgggtgc tggtcctgtt | 840 |
| gatcccagtc tctgccagac caaggcgagt ttccccacta ataaagtgcc gggtgtcagc | 900 |
| agaaaaaaaa aaaaaaaaaa a | 921 |

<210> SEQ ID NO 8
<211> LENGTH: 1200
<212> TYPE: DNA
<213> ORGANISM: Homo sapiens

<400> SEQUENCE: 8

| | |
|---|---|
| cagttaaaag gaggcgcctg ctggcctccc cttacagtgc ttgttcgggg cgctccgctg | 60 |
| gcttcttgga caattgcgcc atgtgtgctg ctcggctagc ggcggcggcg gcggcggccc | 120 |

-continued

| | |
|---|---|
| agtcggtgta tgccttctcg gcgcgcccgc tggccggcgg ggagcctgtg agcctgggct | 180 |
| ccctgcgggg caaggtacta cttatcgaga atgtggcgtc cctctgaggc accacggtcc | 240 |
| gggactacac ccagatgaac gagctgcagc ggcgcctcgg accccggggc ctggtggtgc | 300 |
| tcggcttccc gtgcaaccag tttgggcatc aggtgcgccg gcggagcgg ggcggggcgg | 360 |
| gggcggacgt gcagtagtgg ctgggggcgc cggcggtgtg ctggtgggtg ccgtcggctc | 420 |
| catgcgcgga gagtctggct actctctcgt ttcctttctg ttgctcgtag ctgctgaaat | 480 |
| tcctctccgc ccttgggatt gcgcatggag ggcaaaatcc cggtgactca tagaaaatct | 540 |
| cccttgtttg tggttagaac gtttctctcc tcctcttgac cccgggttct agctgccctt | 600 |
| ctctcctgta ggagaacgcc aagaacgaag agattctgaa ttccctcaag tacgtccggc | 660 |
| ctggtggtgg gttcgagccc aacttcatgc tcttcgagaa gtgcgaggtg aacggtgcgg | 720 |
| gggcgcaccc tctcttcgcc ttcctgcggg aggccctgcc agctcccagc gacgacgcca | 780 |
| ccgcgcttat gaccgacccc aagctcatca cctggtctcc ggtgtgtcgc aacgatgttg | 840 |
| cctggaactt tgagaagttc ctggtgggcc ctgacggtgt gccctacgc aggtacagcc | 900 |
| gccgcttcca gaccattgac atcgagcctg acatcgaagc cctgctgtct caagggccca | 960 |
| gctgtgccta gggcgcccct cctaccccgg ctgcttggca gttgcagtgc tgctgtctcg | 1020 |
| ggggggtttt catctatgag ggtgtttcct ctaaacctac gagggaggaa cacctgatct | 1080 |
| tacagaaaat accacctcga gatgggtgct ggtcctgttg atcccagtct ctgccagacc | 1140 |
| aaggcgagtt tccccactaa taaagtgccg ggtgtcagca gaaaaaaaaa aaaaaaaaa | 1200 |

<210> SEQ ID NO 9
<211> LENGTH: 820
<212> TYPE: DNA
<213> ORGANISM: Homo sapiens

<400> SEQUENCE: 9

| | |
|---|---|
| ctcgatctgc tgctcgtctc aggctcgtag ttcgccttca acatgccgga accagcgaag | 60 |
| tccgctcccg cgcccaagaa gggctcgaag aaagccgtga ctaaggcgca gaagaaggac | 120 |
| ggcaagaagc gcaagcgcag ccgcaaggag agctactccg tatacgtgta caaggtgctg | 180 |
| aagcaggtcc accccgacac cggcatctcc tctaaggcca tgggaatcat gaactccttc | 240 |
| gtcaacgaca tcttcgaacg catcgcgggt gaggcttccc gcctggcgca ttacaacaag | 300 |
| cgctcgacca tcacctccag ggagatccag acggccgtgc gcctgctgct gcccggggag | 360 |
| ttggccaagc acgccgtgtc cgagggcacc aaggccgtca ccaagtacac cagcgctaag | 420 |
| taaacttgcc aaggagggac tttctctgga atttcctgat atgaccaaga aagcttctta | 480 |
| tcaaaagaag cacaattgcc ttcggttacc tcattatcta ctgcagaaaa gaagacgaga | 540 |
| atgcaaccat acctagatgg actttttccac aagctaaagc tggcctcttg atctcattca | 600 |
| gattccaaag agaatcattt acaagttaat ttctgtctcc ttggtccatt ccttctctct | 660 |
| aataatcatt tactgttcct caaagaattg tctacattac ccatctcctc ttttgcctct | 720 |
| gagaaagagt atataagctt ctgtaccca ctgggggtt ggggtaatat tctgtggtcc | 780 |
| tcagccctgt accttaataa atttgtatgc cttttctctt | 820 |

<210> SEQ ID NO 10
<211> LENGTH: 3145
<212> TYPE: DNA
<213> ORGANISM: Homo sapiens

<400> SEQUENCE: 10

-continued

| | |
|---|---|
| cgcagagggc cggggctacg ggcagcgcc ccgggcgatg aggggccggc gttgaccggg | 60 |
| aagagcgggc accgcggcag tggctccgag gggacccgcg atggcagcgc cctgagagga | 120 |
| ggctccaggc agggcgggct gcgctggcag cggccgctga ggtgctggcc ggccggctgg | 180 |
| ctggcgacgg gggcagaagc gacgagaggc gcgctcggca cccgcacccc cgtgcccccg | 240 |
| cctcagttgt ctaaacttcg ggctctcttc cacccgctct gcgcgcccag agtcaacaac | 300 |
| ttcttcaccc ccctccgccc ccgcccttcc ctccgtcagc cccgggagct cgccgcgcgc | 360 |
| cggggaccag gaacctccag cgctgagatg tggccgtgag gcgttggcgg gcggcgagga | 420 |
| gaagctcggc ggcgtccgg ggccggaggg ccgtggggcc ggggcgcagg ggcgcgagca | 480 |
| ccccgcgcct ctccccgcc tcctcctgcc gtctccgccg ctgcccgtgc cttgcaagca | 540 |
| gcagccggag ctgccaagcg tcagggccgc ggagatgtcg tcgtcgtcgc cgccggcggg | 600 |
| ggctgccagc gccgccatct cggctcgga gaaagtggac ggcttcaccc ggaaatcggt | 660 |
| ccgcaaggcg cagaggcaga agcgctccca gggctcgtcg cagtttcgca gccagggcag | 720 |
| ccaggcagag ctgcacccgc tgccccagct caaagatgcc acttcaaatg aacaacaaga | 780 |
| gcttttctgt cagaagttgc agcagtgttg tatactgttt gatttcatgg actctgtttc | 840 |
| agacttgaag agcaaagaaa ttaaaagagc aacactgaat gaactggttg agtatgtttc | 900 |
| aactaatcgt ggtgtaattg ttgaatcagc gtattctgat atagtaaaaa tgatcagtgc | 960 |
| taacatcttc cgtacacttc ctccaagtga taatccagat tttgatccag aagaggatga | 1020 |
| acccacgctt gaggcctctt ggcctcacat acagttggta tatgaattct tcttgagatt | 1080 |
| tttggagagc cctgatttcc agcctagcat tgcaaaacga tacattgatc agaaattcgt | 1140 |
| acaacagctc ctggagcttt ttgatagtga agatcccaga gaacgtgact tcctgaagac | 1200 |
| tgttctgcac cgaatttatg ggaaatttct tggattaaga gcattcatca gaaaacaaat | 1260 |
| taacaacatt ttcctcaggt ttatatatga aacagaacat tcaatggtg ttgctgaact | 1320 |
| tcttgaaaata ttaggaagta ttatcaatgg ctttgcattg ccactgaaag cagaacataa | 1380 |
| acaatttcta atgaaggttc ttattcctat gcatactgca aaaggattag ctttgtttca | 1440 |
| tgctcagcta gcatattgtg ttgtacagtt cctggagaaa gatacaacac taacagagcc | 1500 |
| agtgatcaga ggactgctga aattttggcc aaaaacctgc agtcagaaag aggtgatgtt | 1560 |
| tttaggagaa attgaagaaa tcttagatgt cattgaacca acacagttca aaaaaattga | 1620 |
| agagccactt ttcaagcaga tatccaagtg tgtatccagt tctcatttc aggttgcaga | 1680 |
| aagggcattg tacttctgga ataacgaata tattcttagt ttgattgagg agaacattga | 1740 |
| taaaattctg ccaattatgt ttgccagttt gtacaaaatt tccaaagaac actggaatcc | 1800 |
| gaccattgta gcactggtat acaatgtgct gaaaacccta atggaaatga atggcaagct | 1860 |
| tttcgatgac cttactagct catacaaagc tgaaagacag agagagaaaa agaaggaatt | 1920 |
| ggaacgtgaa gaattatgga aaaaattaga ggagctaaag ctaaagaaag ctctagaaaa | 1980 |
| acagaatagt gcttacaaca tgcacagtat tctcagcaat acaagtgccg aataaaaaaa | 2040 |
| aagcctccca cctctgccgg ataggcagag ttttgtatgc ttttttgaaa tatgtaaaaa | 2100 |
| ttacaaaaca aacctcatca gtataatata attaaaaggc caattttttc tggcaactgt | 2160 |
| aaatggaaaa atatatggac taaacgtagc cctgtgctgt atcatggcca tagtatattg | 2220 |
| taacctttgt ctaatcattg gatttattgt gtcacttctg aagtttcaca gaatgaatg | 2280 |
| aattttatca tctatgatat gagtgagata attatgggag tggtaagaat tatgacttga | 2340 |

```
attcttcttt gattgtgttg cacatagata tggtagtctg ctctgtatat ttttcccttt    2400
tataatgtgc ttttcacact gctgcaaacc ttagttacat cctaggaaaa aatacttcct    2460
aaaataaaac taaggtatca tccttaccct tctctttgtc tcacccagaa atatgatggg    2520
gggaattacc tgccctaacc cctccctcaa taaatacatt actgtactct ggaatttagg    2580
caaaacctta aatctccagg cttttaaag cacaaaatat aaataaaagc tgggaaagta    2640
aaccaaaatt cttcagattg ttcctcatga atatccccct tcctctgcaa ttctccagag    2700
tggtaacaga tgggtagagg cagctccagt gaattaccca gcttgcctct caattcattc    2760
ctcctcttcc tctcaaaggc tgaaggcagg gcctttccag tcctcacaac ctgtccttca    2820
cctagtccct cctgacccag ggatggaggc tttgagtccc acagtgtggt gatacagagc    2880
actagttgtc actgcctggc tttatttaaa ggaactgcag taggcttcct ctgtagagct    2940
ctgaaaaggt tgactatata gaggtcttgt atgttttac ttggtcaagt atttctcaca    3000
tcttttgtta tcagagtacc attccaatct cttaacttgc agttgtgtgg aaaactgttt    3060
tgtaatgaaa gatcttcatt gggggattga gcagcattta ataaagtcta tgtttgtatt    3120
ttgccttaaa aaaaaaaaaa aaaaa                                         3145

<210> SEQ ID NO 11
<211> LENGTH: 546
<212> TYPE: DNA
<213> ORGANISM: Homo sapiens

<400> SEQUENCE: 11
aaagcggcca tgttttacat atttcttgat tttgtttgtt ttctcgtgag cttaggccgc      60
tggttttggt gattttgtc tgattgcaat gtctggacgt ggtaagcaag gaggcaaagc     120
tcgcgccaaa gcgaaatccc gctcttctcg cgctggtctc cagttcccgg tgggccgagt     180
gcaccgcctg ctccgtaaag caactacgc agagcgggtt ggggcaggcg cgccggtgta     240
cctggcggcg gtgttagagt acctgaccgc cgagatcctg gagctggccg gcaacgcggc     300
tcgcgacaac aagaagactc gcatcatccc gcgccacttg cagctggcca tccgcaacga     360
cgaggagctc aacaaactgc taggccgggt gaccattgct cagggcggcg tccttcctaa     420
catccaggcc gtgcttctgc ctaagaagac cgagagtcac cacaaggcca agggcaagtg     480
atttgacagg tatctgagct cccggaaacg ctatcaaacc caaaggctct tttcagagcc     540
ccccta                                                              546

<210> SEQ ID NO 12
<211> LENGTH: 3431
<212> TYPE: DNA
<213> ORGANISM: Homo sapiens

<400> SEQUENCE: 12
gggggaggag ggcggtcgtc cggggttagg ttgagggggg gcgtcggtcc gttctgggcg      60
ggggatgact cacagcccat cccatctccc cgacgccgcc cgcccgcgca gtgctagctc     120
catggcttag cggaggaggc ggcagtgcg agctgggggg agggggggact cttatttgt     180 taggggacc gggccgaggc ccgaccggcc tggcagggct cgcccggggc gggcgtcat      240 gtctcatgcg gccgaaccag ctcgggatgg cgtagaggcc agcgcggagg gcctcgagcc     300
cgtgttcgtg ctgttggagg agcgcaggcc ggccgactcg gctcagctgc tcagcctgaa     360
ctctttgctt ccggaatccg ggattgttgc tgacatagaa ttagaaaacg tccttgatcc     420
tgacagcttc tacgagctca aaagccaacc cttacccctt cgctcaagcc tcccaatatc     480
```

-continued

```
actgcaggcc acaccagcca ccccagctac actctctgca tcgtcttctg caggggctc     540 caggacccct gccatgtcgt catcttcttc atcgagggtc ttgctgcggc agcagctaat    600
gcgggcccag gcgcaggagc aggagaggcg tgagcgtcgg gaacaggccg ccgcggctcc    660
cttccccagt cctgcacctg cctctcctgc catctctgtg gttggcgtct ctgctggggg    720
ccacacattg agccgtccac cccctgctca ggtgccagg gaggtgctca aggtgcagac     780
ccatctggag aacccaacgc gctaccacct gcagcaggcg cgccggcagc aggtgaaaca    840
gtacctgtcc accacactcg ggcccaagct ggcttcccag gccctcaccc caccgccggg    900
gcccgcaagt gcccagccac tgcctgcccc tgaggctgcc cacactaccg ccccacagg     960 cagtgcgccc aacagcccca tggcgctgct caccatcggg tccagctcag agaaggagat   1020
tgatgatgtc attgatgaga tcatcagcct ggagtccagt acaatgatg aaatgctcag    1080 ctatctgccc ggaggcacca caggactgca gctccccagc acgctgcctg tgtcagggaa   1140
tctgcttgat gtgtacagta gtcaaggcgt ggccacacca gccatcactg tcagcaactc   1200
ctgcccagct gagctgccca acatcaaacg ggagatctct gagaccgagg caaaggccct   1260
tttgaaggaa cggcagaaga agacaatca caacctaatt gagcgtcgca ggcgattcaa    1320
cattaacgac aggatcaagg aactgggcac tctcatccct aagtccagtg acccggagat   1380
gcgctggaac aagggcacca tcctgaaggc ctctgtggat tatatccgca agctgcagaa   1440
ggagcagcag cgctccaaag acctggagag ccggcagcga tccctggagc aggccaaccg   1500
cagcctgcag ctccgaattc aggaactaga actgcaggcc cagatccatg gcctgccagt   1560
gcctcccact ccagggctgc tttccttggc cacgacttcg gcttctgaca gcctcaagcc   1620
agagcagctg gacattgagg aggagggcag gccaggcgca gcaacgttcc atgtaggggg   1680
gggacctgcc cagaatgctc cccatcagca gcccctgca ccgccctcag atgcccttct    1740
ggacctgcac tttcccagcg accacctggg ggacctggga cccccttcc acctggggct    1800 ggaggacatt ctgatggagg aggaggaggg ggtggtggga ggactgtcgg ggggtgccct   1860
gtccccactg cgggctgcct ccgatcccct gctctcttca gtgtcccctg ctgtctccaa   1920
ggccagcagc cgccgcagca gcttcagcat ggaagaggag tcctgatcag gcctcacccc   1980
tcccctggga cttccccacc caggaaagga ggaccagtca ggatgaggcc ccgcctttc    2040 ccccacccct ccatgagact gccctgccca ggtatcctgg gggaagagga gatgtgatca   2100 ggcccccaccc ctgtaatcag gcaaggagga ggagtcagat gaggccctgc accttcccca   2160
aaggaaccgc ccagtgcagg tatttcagaa ggagaaggct ggagaaggac atgagatcag   2220
ggcctgcccc ctggggatca cagcctcacc cctgccctg tgggactcat ccttgcccag    2280
gtgagggaag gagacaggat gaggtctcga ccctgtcccc tagggactgt cctagccagg   2340
tctcctggga aagggagatg tcaggatgtt gctccatcct ttgtcttgga accaccagtc   2400
tagtccgtcc tggcacagaa gaggagtcaa gtaatggagg tccagccct ggggtttaa     2460 gctctgcccc ttccccatga accctgccct gctctgccca ggcaaggaac agaagtgagg   2520
atgagaccca gccccttccc ctgggaactc tcctggcctt ctaggaatgg aggagccagg   2580
ccccacccct tccctatagg aacagcccag cacaggtatt tcaggtgtga agaatcagt    2640 aggaccaggc caccgctagt gcttgtggag atcacagccc cacccttgtc cctcagcaac   2700
atcccatcta agcattccac actgcaggga ggagtggtac ttaagctccc ctgccttaac   2760
ctgggaccaa cctgacctaa cctaggaggg ctctgagcca accttgctct tggggaaggg   2820
```

```
gacagattat gaaatttcat ggatgaattt tccagaccta tatctggagt gagaggcccc    2880 caccettggg cagagtcctg ccttcttcct tgaggggcag tttgggaagg tgatgggtat    2940
tagtggggga ctgagttcag gttaccagaa ccagtacctc agtattcttt ttcaacatgt    3000
agggcaagag gatgaaggaa ggggctatcc tgggacctcc ccagcccagg aaaaactgga    3060
agccttcccc cagcaaggca gaagcttgga ggagggttgt aaaagcatat tgtaccccct    3120
catttgttta tctgattttt ttattgctcc gcatactgag aatctaggcc accccaacct    3180
ctgttcccca cccagttctt catttggagg aatcaccca tttcagagtt atcaagagac    3240 actccccct ccattcccac ccctcatacc tacacccaag gttgtcagct ttggattgct    3300
ggggccaggc cccatggagg gtatactgag gggtctatag gtttgtgatt aaaataataa    3360
aagctaggcg tgtttgatgc gcttttaact ttgaaaaaaa aaaaaaaaaa aaaaaaaaaa    3420
aaaaaaaaaa a                                                        3431

<210> SEQ ID NO 13
<211> LENGTH: 2705
<212> TYPE: DNA
<213> ORGANISM: Homo sapiens

<400> SEQUENCE: 13
accgagctcc gtcgtctcgt ttccggcggt cgcgcgctct tttctcggga cgggagaggc      60
cgtgtagcgt cgccgttact ccgaggagat accagtcggt agaggagaag tcgaggttag     120
agggaactgg gaggcacttt gctgtctgca atcgaagttg agggtgcaaa aatgcagagt     180
aataaaactt ttaacttgga gaagcaaaac catactccaa gaaagcatca tcaacatcac     240
caccagcagc agcaccacca gcagcaacag cagcagccgc caccaccgcc aatacctgca     300
aatgggcaac aggccagcag ccaaaatgaa ggcttgacta ttgacctgaa gaattttaga     360
aaaccaggag agaagacctt cacccaacga agccgtcttt tgtgggaaaa tcttcctccc     420
gacatcactg aggaagaaat gaggaaacta tttgagaaat atggaaaggc aggcgaagtc     480
ttcattcata aggataaagg atttggcttt atccgcttgg aaacccgaac cctagcggag     540
attgccaaag tggagctgga caatatgcca ctccgtggaa agcagctgcg tgtgcgcttt     600
gcctgccata gtgcatccct tacagttcga aaccttcctc agtatgtgtc caacgaactg     660
ctggaagaag ccttttctgt gtttggccag gtagagaggg ctgtagtcat tgtggatgat     720
cgaggaaggc cctcaggaaa aggcattgtt gagttctcag ggaagccagc tgctcggaaa     780
gctctggaca gatgcagtga aggctccttc ctgctaacca catttcctcg tcctgtgact     840
gtggagccca tggaccagtt agatgatgaa gagggacttc cagagaagct ggttataaaa     900
aaccagcaat tcacaaggga acgagagcag ccacccagat ttgcacagcc tggctccttt     960
gagtatgaat atgccatgcg ctggaaggca ctcattgaga tggagaagca gcagcaggac    1020
caagtggacc gcaacatcaa ggaggctcgt gagaagctgg agatggagat ggaagctgca    1080
cgccatgagc accaggtcat gctaatgaga caggatttga tgaggcgcca agaagaactt    1140
cggaggatgg aagagctgca caaccaagag gtgcaaaaac gaaagcaact ggagctcagg    1200
caggaggaag agcgcaggcg ccgtgaagaa gagatgcggc ggcagcaaga gaaatgatg     1260 cggcgacagc aggaaggatt caagggaacc ttccctgatg cgagagagca ggagattcgg    1320
atgggtcaga tggctatggg aggtgctatg ggcataaaca acagaggtgc catgcccct     1380 gctcctgtgc cagctggtac cccagctcct ccaggacctg ccactatgat gccggatgga    1440
actttgggat tgaccccacc aacaactgaa cgctttggtc aggctgctac aatggaagga    1500
```

```
attggggcaa ttggtggaac tcctcctgca ttcaaccgtg cagctcctgg agctgaattt    1560
gccccaaaca aacgtcgccg atactaataa gttgcagtgt ctagtttctc aaaaccctta    1620
aaagaaggac ccttttttgga ctagccagaa ttctaccctg aaaagtgtt agggattcct     1680 tccaatagtt agatctaccc tgcctgtact actctaggga gtatgctgga ggcagagggc    1740
aagggagggg tggtattaaa caagtcaatt ctgtgtggta tattgtttaa tcagttctgt    1800
gtggtgcatt cctgaagtct ctaatgtgac tgttgagggc ctggggaaac catggcaaag    1860
tggatccagt tagagcccat taatcttgat cattccggtt ttttttttttt ttgtccatct    1920 tgtttcattt gcttgccccg cccccgagac ggagtcttac tctgtcgccc aggctggagt    1980
gtagtggcat gatctcggct cactgcaatc tctgcctccc gggttcaagc ttgtccaggt    2040
tgatcttgaa ctcctgacct cgtgatctac ccacctcggc ctcccaaaat gctgggatta    2100
caggggtgag ccaccgtgcc caacctcact tgcttcttat ccttacactc ccccagcccc    2160
agagaaactg ccacatacac cacaaaaacc aaacatcccc caatgacctt agccccattg    2220
ctccattcac tcccaggtga gaattcaggc aaacgtccac aaaggtcaca ggcagcgtac    2280
atacggttct gttataccccc atatattacc ccttcatgtc ctaaagaaga catttctct    2340 tagagatttt cattttagtg tatctttaaa aaaaaatctt gtgttaactt gcctccatct    2400
ttttcttggg tgaggacacc caggaatgac ccttttgtgt ctatgatgtt gctgttcaca    2460
gcttttcttg ataggcctag tacaatcttg gaacagggt tactgtatac tgaaggtctg     2520
acagtagctc ttagactcgc ctatcttagg tagtcatgct gtgcatttttt tttttcattg    2580 gtgtactgtg tttgatttgt ctcatatatt tggagttttt ctgaaaaatg gagcagtaat    2640
gcagcatcaa cctattaaaa tacattttaa gccttttaaa aaaaaaaaa aaaaaaaaaa    2700 aaaaa                                                                2705

<210> SEQ ID NO 14
<211> LENGTH: 1772
<212> TYPE: DNA
<213> ORGANISM: Homo sapiens

<400> SEQUENCE: 14
gaaagcgggc ttcccgcccc gcccagaccg ccgaggctgc cgccggagtc gccaccgccg      60
cgccctcgcc caccgcccg cccgccgctc ccggccccgc tcgcccccte cgccgccgcc     120 gcccgccccct gcgactacgc tgcggcctcc cgcccgctcc cgctcgctcc cgcggccctc    180
gctcgcctcg cgccggcagt tttgggccta cacctcccct cccccgcca gccgccaaag    240 acttgaccac gtaacgagcc caactccccc gaacgccgcc cgccgctcgc catggatgcc    300
ggtgtgactg aaagtggact aaatgtgact ctcaccattc ggcttcttat gcacggaaag    360
gaagtaggaa gcatcattgg gaagaaaggg gagtcggtta agaggatccg cgaggagagt    420
ggcgcgcgga tcaacatctc ggagggggaat tgtccggaga gatcatcac tctgaccggc    480 cccaccaatg ccatctttaa ggctttcgct atgatcatcg acaagctgga ggaagatatc    540
aacagctcca tgaccaacag taccgcggcc agcaggcccc cggtcaccct gaggctggtg    600
gtgccggcca cccagtgcgg ctccctgatt gggaaaggcg ggtgtaagat caaagagatc    660
cgcgagagta cggggggcgca ggtccaggtg gcggggggata tgctgcccaa ctccaccgag    720
cgggccatca ccatcgctgg cgtgccgcag tctgtcaccg agtgtgtcaa gcagatttgc    780
ctggtcatgc tggagacgct ctcccagtct ccgcaaggga gagtcatgac cattccgtac    840
```

| | |
|---|---|
| cagcccatgc cggccagctc cccagtcatc tgcgcgggcg gccaagatcg gtgcagcgac | 900 |
| gctgcgggct accccccatgc cacccatgac ctggagggac cacctctaga tgcctactcg | 960 |
| attcaaggac aacacaccat ttctccgctc gatctggcca agctgaacca ggtggcaaga | 1020 |
| caacagtctc actttgccat gatgcacggc gggaccggat tcgccggaat tgactccagc | 1080 |
| tctccagagg tgaaaggcta tgggcaagt ttggatgcat ctactcaaac cacccatgaa | 1140 |
| ctcaccattc caaataactt aattggctgc ataatcgggc gccaaggcgc caacattaat | 1200 |
| gagatccgcc agatgtccgg ggcccagatc aaaattgcca acccagtgga aggctcctct | 1260 |
| ggtaggcagg ttactatcac tggctctgct gccagtatta gtctggccca gtatctaatc | 1320 |
| aatgccaggc tttcctctga agggcatg gggtgcagct agaacagtgt aggttccctc | 1380 |
| aataacccct ttctgctgtt ctcccatgat ccaactgtga aatttctggt cagtgattcc | 1440 |
| aggttttaaa taatttgtaa gtgttcagtt tctacacaac tttatcatcc gctaagaatt | 1500 |
| taaaaatcac attctctgtt cagctgttaa tgctgggatc catatttagt tttataagct | 1560 |
| tttccctgtt tttagttttg ttttgggttt tttggctcat gaatttatt tctgtttgtc | 1620 |
| gataagaaat gtaagagtgg aatgttaata aatttcagtt tagttctgta atgtcaagaa | 1680 |
| tttaagaatt aaaaaacgga ttggttaaaa aatgcttcat atttgaaaaa gctgggaatt | 1740 |
| gctgtcttaa aaaaaaaaaa aaaaaaaaaa aa | 1772 |

<210> SEQ ID NO 15
<211> LENGTH: 1928
<212> TYPE: DNA
<213> ORGANISM: Homo sapiens

<400> SEQUENCE: 15

| | |
|---|---|
| ccggctagtc tttggccgcc gccgaacccc gcgcgccact cgctcgctca gagggaggag | 60 |
| aaagtggcga gttccggatc cctgcctagc gcggcccaac ctttactcca gagatcatgg | 120 |
| ctgccgagga tgtggtggcg actggcgccg acccaagcga tctggagagc ggcgggctgc | 180 |
| tgcatgagat tttcacgtcg ccgctcaacc tgctgctgct tggcctctgc atcttcctgc | 240 |
| tctacaagat cgtgcgcggg gaccagccgg cggccagcgg cgacagcgac gacgacgagc | 300 |
| cgccccctct gccccgcctc aagcggcgcg acttcacccc cgccgagctg cggcgcttcg | 360 |
| acggcgtcca ggacccgcgc atactcatgg ccatcaacgg caaggtgttc gatgtgacca | 420 |
| aaggccgcaa attctacggg cccgaggggc cgtatgggt cttttgctgga agagatgcat | 480 |
| ccaggggcct tgccacattt tgcctggata aggaagcact gaaggatgag tacgatgacc | 540 |
| tttctgacct cactgctgcc cagcaggaga ctctgagtga ctgggagtct cagttcactt | 600 |
| tcaagtatca tcacgtgggc aaactgctga aggagggga ggagcccact gtgtactcag | 660 |
| atgaggaaga accaaagat gagagtgccc ggaaaaatga ttaaagcatt cagtggaagt | 720 |
| atatctatt ttgtatttttg caaatcatt tgtaacagtc cactctgtct ttaaaacata | 780 |
| gtgattacaa tatttagaaa gttttgagca cttgctataa gttttttaat taacatcact | 840 |
| agtgacacta ataaaattaa cttcttagaa tgcatgatgt gtttgtgtgt cacaaatcca | 900 |
| gaaagtgaac tgcagtgctg taatacacat gttaatactg ttttttcttct atctgtagtt | 960 |
| agtacaggat gaatttaaat gtgttttttcc tgagagacaa ggaagacttg ggtatttccc | 1020 |
| aaaacaggta aaaatcttaa atgtgcacca agagcaaagg atcaactttt agtcatgatg | 1080 |
| ttctgtaaag acaacaaatc ccttttttttt tctcaattga cttaactgca tgatttctgt | 1140 |
| tttatctacc tctaaagcaa atctgcagtg ttccaaagac tttggtatgg attaagcgct | 1200 |

```
gtccagtaac aaaatgaaat ctcaaaacag agctcagctg caaaaaagca tattttctgt    1260
gtttctggac tgcactgttg tccttgccct cacatagaca ctcagacacc ctcacaaaca    1320
cagtagtcta tagttaggat taaaatagga tctgaacatt caaagaaag  ctttggaaaa    1380 aaagagctgg ctggcctaaa aacctaaata tatgatgaag attgtaggac tgtcttccca    1440
agccccatgt tcatggtggg gcaatggtta tttggttatt ttactcaatt ggttactctc    1500
atttgaaatg agggagggac atacagaata ggaacaggtg tttgctctcc taagagcctt    1560
catgcacacc cctgaaccac gaggaaacag tacagtcgct agtcaagtgg tttttaaagt    1620
aaagtatatt cataaggtaa cagttattct gttgttataa aactatacccc actgcaaaag    1680 tagtagtcaa gtgtctaggt ctttgatatt gctcttttgg ttaacactaa gcttaagtag    1740
actatacagt tgtatgaatt tgtaaaagta tatgaacacc tagtgagatt tcaaacttgt    1800
aattgtggtt aaatagtcat tgtattttct tgtgaactgt gttttatgat tttacctcaa    1860
atcagaaaac aaaatgatgt gctttggtca gttaataaaa atggttttac ccactaaaaa    1920
aaaaaaaa                                                             1928

<210> SEQ ID NO 16
<211> LENGTH: 3428
<212> TYPE: DNA
<213> ORGANISM: Homo sapiens

<400> SEQUENCE: 16
tggagagtaa tgttacagag cggagagagt gaggaggctg cgtctggctc ccgctctcac      60
agccattgca gtacattgag ctccatagag acagcgccgg ggcaagtgag agccggacgg     120
gcactgggcg actctgtgcc tcgctgagga aaaataacta acatgggca  aaggagatcc     180 taagaagccg agaggcaaaa tgtcatcata tgcattttttt gtgcaaactt gtcgggagga    240
gcataagaag aagcacccag atgcttcagt caacttctca gagttttcta agaagtgctc     300
agagaggtgg aagaccatgt ctgctaaaga gaaaggaaaa tttgaagata tggcaaaagc    360
ggacaaggcc cgttatgaaa gagaaatgaa aacctatatc cctcccaaag gggagacaaa    420
aaagaagttc aaggatccca atgcacccaa gaggcctcct tcggccttct tcctcttctg    480
ctctgagtat cgcccaaaaa tcaaggaga  acatcctggc ctgtccattg gtgatgttgc    540
gaagaaactg ggagagatgt ggaataacac tgctgcagat gacaagcagc cttatgaaaa    600
gaaggctgcg aagctgaagg aaaaatacga aaaggatatt gctgcatatc gagctaaagg    660
aaagcctgat gcagcaaaaa agggagttgt caaggctgaa aaaagcaaga aaagaagga    720 agaggaggaa gatgaggaag atgaagagga tgaggaggag gaggagatg  aagaagatga    780 agatgaagaa gaagatgatg atgatgaata agttggttct agcgcagttt ttttttttctt    840 gtctataaag catttaaccc ccctgtacac aactcactcc ttttaaagaa aaaaattgaa    900
atgtaaggct gtgtaagatt tgtttttaaa ctgtacagtg tcttttttg  tatagttaac    960 acactaccga atgtgtcttt agatagccct gtcctggtgg tattttcaat agccactaac    1020
cttgcctggt acagtatggg ggttgtaaat tggcatggaa atttaaagca ggttcttgtt    1080
ggtgcacagc acaaattagt tatatatggg gatggtagtt ttttcatctt cagttgtctc    1140
tgatgcagct tatacgaaat aattgttgtt ctgttaactg aataccactc tgtaattgca    1200
aaaaaaaaaa aaaagttgca gctgttttgt tgacattctg aatgcttcta agtaaataca    1260
atttttttta ttagtattgt tgtccttttc ataggtctga aatttttctt cttgaggga     1320
```

```
agctagtctt ttgcttttgc ccattttgaa tcacatgaat tattacagtg tttatccttt    1380
catatagtta gctaataaaa agcttttgtc tacacaccct gcatatcata atggggtaa     1440 agttaagttg agatagtttt catccataac tgaacatcca aaatcttgat cagttaagaa    1500
atttcacata gcccacttac atttacaaac tgaagagtaa tcaatctact caaagcatgg    1560
gattattaga atcaaacatt ttgaaagtct gtccttgaag gactaataga aaagtatgtt    1620
ctaaccttta catgaggact ctattcttta actcccatta ccatgtaatg gcagttatat    1680
tttgcagttc ccacattaaa gaagacctga gaatgtatcc ccaaaagcgt gagcttaaaa    1740
tacaagactg ccatattaaa ttttttgttg acattagtct cagtgaagac tatgaaaatg    1800
ctggctatag atgtcttttc ccatttatct aaatatggac tgctcaggaa acgagacttt    1860
ccattacaag tatttttaat taattgggcc agcttttcaa acaaagatgc cacattcaaa    1920
atagggtata ttttcctata ttacggtttg cccctttata aatccaagta gataggaaga    1980
aagaagacaa actttgcatc tcagtatgaa ttattcaatt tatttgaatg attttctttt    2040
acaaaacaaa ctcattcatt agtcatgttt atctgcttag gagtttaggg aacaatttgg    2100
caattttgtg gttttcgaga ttatcgtttt cttaaagtgc cagtatttta aaatagcgtt    2160
cttgtaattt tacacgcttt tgtgatggag tgctgttttg ttatataatt tagacttgga    2220
ttctttccat ttgcatttgt ttatgtaatt tcaggaggaa tactgaacat ctgagtcctg    2280
gatgatacta ataaactaat aattgcagag gttttaaata ctagttaaat ggctttcact    2340
taagaactta agattttgtt acatatttt aaatcttgtt tctaataata cctcttagca     2400
gtacctttta aataagtata agggatggca aagttttcc ctttaaaaat actcacttta     2460
tgcttataaa taggttaatg ggctgataaa aggttttgtc aaacattgca agtattcggt    2520
gctatatata aaggaggaaa aactagtttt actttcagaa tgatttaaac aagatttta     2580 aaaacaagat acatgcaagc gaacagcagg gttagtgata ggctgcaatt gtgtcgaaca    2640
tcagattttt tgttaagagg agcaaatgac tcaatctgat ttagatggaa gtttctactg    2700
tatagaaatc accattaatc accaacatta ataattctga tccatttaaa atgaattctg    2760
gctcaaggag aatttgtaac tttagtaggt acgtcatgac aactaccatt ttttaagat    2820 gttgagaatg ggaacagttt ttttagggtt tattcttgac cacagatctt aagaaaatgg    2880
acaaaacccc tcttcaatct gaagattagt atggtttggt gttctaacag tatccctag    2940 aagttggatg tctaaaactc aagtaaatgg aagtgggagg caatttagat aagtgtaaag    3000
ccttgtaact gaagatgatt ttttttagaa agtgtataga aactatttta atgccaagat    3060
agttacagtg ctgtggggtt taaagacttt gttgacatca agaaaagact aaatctataa    3120
ttaattgggc caacttttaa aatgaagatg cttttaaaa ctaatgaact aagatgtata    3180
aatcttagtt tttttgtatt ttaaagatag gcatatggca tattgattaa cgagtcaaat    3240
ttcctaactt tgctgtgcaa aggttgagag ctattgctga ttagttacca cagttctgat    3300
gatcgtccca tcacagtgtt gttaatgttt gctgtattta ttaattttct taaagtgaaa    3360
tctgaaaaat gaaatttgtg tgtcctgtgt acccgagggg taatgattaa atgataaaga    3420
taagaaaa                                                             3428
```